US012638144B2

(12) United States Patent
Yaghi et al.

(10) Patent No.: US 12,638,144 B2
(45) Date of Patent: May 26, 2026

(54) COVALENT ORGANIC FRAMEWORKS

(71) Applicant: The Regents of the University of California, Oakland, CA (US)

(72) Inventors: Omar M. Yaghi, Berkeley, CA (US); Ha L. Nguyen, Berkeley, CA (US); Steven J. Lyle, Berkeley, CA (US); Nikita Hanikel, Berkeley, CA (US); Hao Lyu, Berkeley, CA (US); Wentao Xu, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 767 days.

(21) Appl. No.: 17/849,680

(22) Filed: Jun. 26, 2022

(65) Prior Publication Data

US 2022/0370981 A1 Nov. 24, 2022
US 2025/0003558 A9 Jan. 2, 2025

Related U.S. Application Data

(63) Continuation of application No. PCT/US2021/013010, filed on Jan. 11, 2021.

(Continued)

(51) Int. Cl.

*F21L 4/04* (2006.01)
*B01D 53/04* (2006.01)

(Continued)

(52) U.S. Cl.

CPC ................ *F21L 4/04* (2013.01); *B01D 53/04* (2013.01); *B01D 53/261* (2013.01); *B01D 53/62* (2013.01); *B01D 53/81* (2013.01); *B01J 20/226* (2013.01); *B01J 20/28016* (2013.01); *B01J 20/28033* (2013.01); *C07D 251/24* (2013.01);

(Continued)

(58) Field of Classification Search

CPC ........ B01D 2253/202; B01D 2257/504; B01D 2257/80; B01D 2258/06; B01D 53/04; B01D 53/261; B01D 53/62; B01D 53/81; B01J 20/226; B01J 20/28016; B01J 20/28033; C07D 251/24; C07D 471/04; C07D 493/22; C08G 12/00; C08G 73/0644; C08G 73/0688; F21L 4/04; F21L 4/045; F21V 14/065; F21V 14/085; F21V 21/0832; F21V 21/088; F21V 21/0885; F21V 23/002; F21V 23/0414; F21V 23/0428;

(Continued)

(56) References Cited

U.S. PATENT DOCUMENTS

2015/0291870 A1 10/2015 Van Horn et al.

FOREIGN PATENT DOCUMENTS

EP 2832767 A1 * 2/2015 ......... G03G 5/14769
JP 2018192397 A * 12/2018

OTHER PUBLICATIONS

Nakamura et al. JP2018192397A English Machine Translation (Year: 2018).*

(Continued)

*Primary Examiner* — Anthony J Zimmer
*Assistant Examiner* — Jordan W Taylor
(74) *Attorney, Agent, or Firm* — Todd W. Esker; Bozicevic, Field & Francis LLP

(57) ABSTRACT

Chemically and thermally stable covalent organic framework (COF) materials are configured and operative as solid adsorbents for capturing gases and water.

6 Claims, 23 Drawing Sheets

Related U.S. Application Data

(60) Provisional application No. 63/028,523, filed on May 21, 2020, provisional application No. 63/023,107, filed on May 11, 2020, provisional application No. 62/959,972, filed on Jan. 11, 2020.

(51) Int. Cl.

| | |
|---|---|
| ***B01D 53/26*** | (2006.01) |
| ***B01D 53/62*** | (2006.01) |
| ***B01D 53/81*** | (2006.01) |
| ***B01J 20/22*** | (2006.01) |
| ***B01J 20/28*** | (2006.01) |
| ***C07D 251/24*** | (2006.01) |
| ***C07D 471/04*** | (2006.01) |
| ***C07D 493/22*** | (2006.01) |
| ***F21V 9/08*** | (2018.01) |
| ***F21V 14/06*** | (2006.01) |
| ***F21V 21/08*** | (2006.01) |
| ***F21V 21/088*** | (2006.01) |
| ***F21V 23/04*** | (2006.01) |

(52) U.S. Cl.

CPC ......... *C07D 471/04* (2013.01); *C07D 493/22* (2013.01); *F21V 9/083* (2013.01); *F21V 14/065* (2013.01); *F21V 21/0832* (2013.01); *F21V 21/0885* (2013.01); *F21V 23/0414* (2013.01); *F21V 23/0492* (2013.01); *B01D 2253/202* (2013.01); *B01D 2257/504* (2013.01); *B01D 2257/80* (2013.01); *B01D 2258/06* (2013.01)

(58) Field of Classification Search

CPC .. F21V 23/0492; F21V 9/083; F21Y 2115/10; Y02C 20/40

See application file for complete search history.

(56) References Cited

OTHER PUBLICATIONS

Pang et al. Chem. Sci.,2017,8, 3866 (Year: 2017).*

Sick et al. J. Am. Chem. Soc. 2018, 140, 2085-2092 (Year: 2018).*

Waller et al. J. Am. Chem. Soc. 2016, 138, 15519-15522 (Year: 2016).*

Zhou et al. J. Am. Chem. Soc. 2014, 136, 15885-15888 (Year: 2014).*

Lyle et al. Dissertation, 2019 (Year: 2019).*

Steven James Lyle, Synthesis, Characterization, and Multistep Postsynthetic Modification of Covalent Organic Frameworks, UC Berkeley Electronic Theses and Dissertations, Dec. 31, 2019.

Lijuan Zhu et al., Crystallization of covalent organic frameworks for gas storage applications, Molecules 2017, 22, 1149.

Extended European Search Report for related EP 21738013.8, 13 pages (Aug. 25, 2023).

Ma Tianqiong et al: "Single-crystal x-ray diffraction structures of covalent organic frameworks", Science, [Online] vol. 361, No. 6397, Jul. 6, 2018, pp. 48-52, US.

Lyu Hao et al: "Porous Crystalline Olefin-Linked Covalent Organic Frameworks". Journal of the American Chemical Society, [Online] vol. 141, No. 17, Apr. 19, 2019, pp. 6848-6852.

International Search Report, Written Opinion, in priority application PCT/US21/13010, 10 pages (May 7, 2021).

Examination Search Report issued by Canadian Intellectual Property Office for related CA3,167,046, 5 pages, Sep. 12, 2023.

Zhou Tian-You et al. "One-Step Construction of Two Different Kinds of Pores in a 2D Covalent Organic Framework", J. Am. Chem. Soc., vol. 136, No. 45, pp. 15885-15888.

* cited by examiner 4-c sql

(3,4,4)-c mtf

ETTA

TFB

Ditopic building units

Tritopic building units

Tetratopic building units

Hexatopic building units

Octatopic building units n = 8-16

Dodecatopic building units n = 12-24

$R^4$ = n = 5,6,7, ...

(M: metal ion, metal complex, or metal clusters)

$R^5$ =  n = 6,7,8, ...

(M: metal ion, metal complex, or metal clusters)

⋮ ⋮

$R^m$ =  m = 6,7,8, ...
n = m+1,m+2,m+3, ...

(M: metal ion, metal complex, or metal clusters)

2 points of extension

$L_m$—$L_m$ (from C-C coupling, Zinke reaction)

3 points of extension

Fig. 37
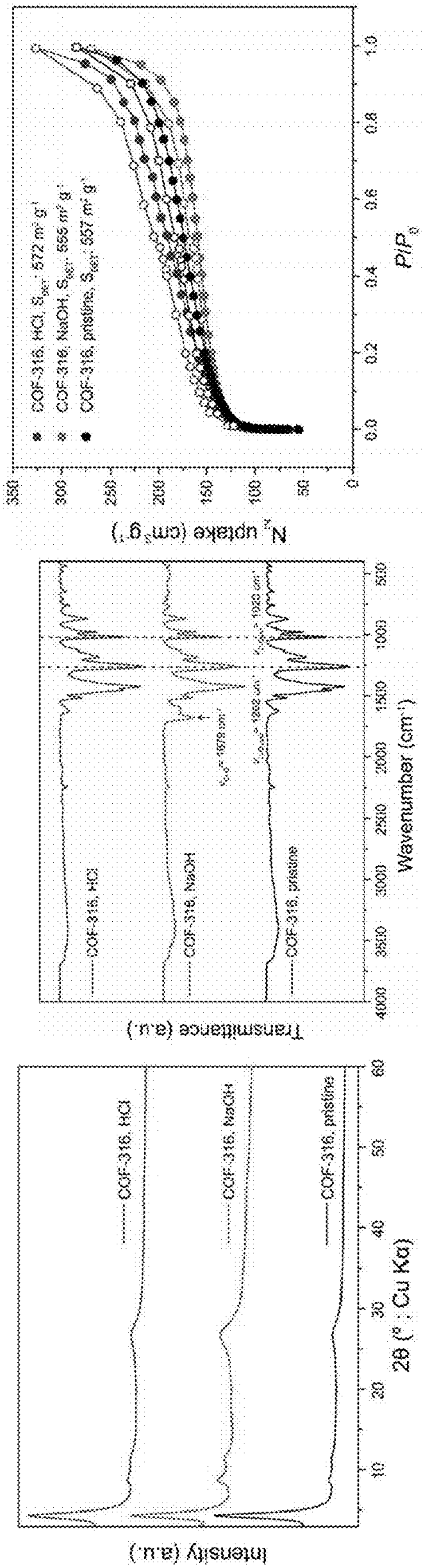
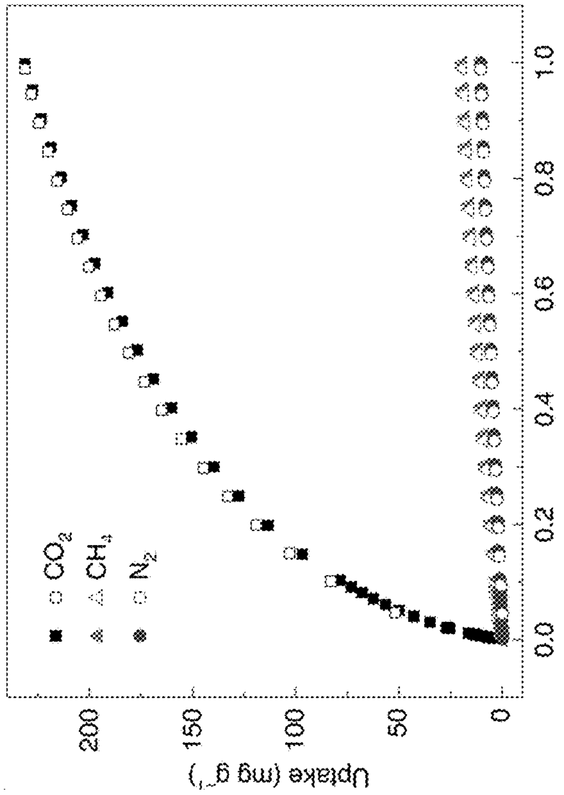
Fig. 38
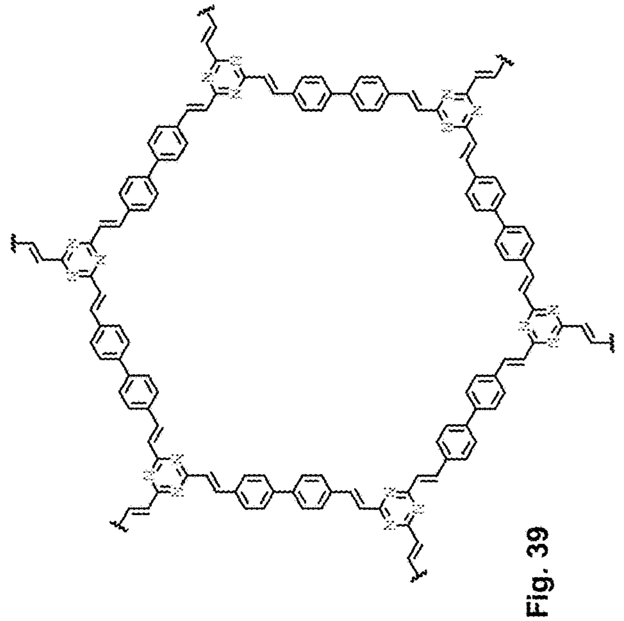
Fig. 39

COVALENT ORGANIC FRAMEWORKS

INTRODUCTION

Covalent organic frameworks (COFs) are a class of porous, crystalline organic solid materials that are composed of organic building units connected with covalent bonds in two- or three-dimensional space. COFs can be used as gas and water sorbents. We disclose chemically and thermally stable covalent organic framework (COF) materials configured and operative as solid adsorbents for capturing gases and water.

SUMMARY OF THE INVENTION

The invention provides chemically and thermally stable covalent organic framework (COF) materials configured and operative as solid adsorbents for capturing gases and water.

Aspect 1. Porous Covalent Organic Frameworks for Atmospheric Water Harvesting.

We disclose a diverse panel of porous covalent organic frameworks for configured and suitable for atmospheric water harvesting. In an example, we disclose a covalent organic framework COF-432 with exceptional water sorption properties resulting from its unique structure. COF-432 is a porous, crystalline two-dimensional imine-linked COF with a voided square grid topology, and highly crystalline, which is reflected in no to minimal hysteretic behavior for the water sorption process. Unlike other reported COFs, COF-432 meets the requirements desired for water harvesting from air in that it exhibits an 'S'-shaped water sorption isotherm with a steep pore-filling step at low relative humidity and without hysteretic behavior—properties essential for energy efficient uptake and release of water. Further, it can be regenerated at ultra-low temperatures with exceptional hydrolytic stability, as demonstrated by the retention of its working capacity after 300 water adsorption-desorption cycles. The resulting water sorption working capacity between 20 and 40% RH is 0.23 g $g_{COF}^{-1}$. Furthermore, the framework exhibits an exceptional hydrolysis resistance (at least 20 d in water at room temperature) and no loss of its working capacity after at least 300 consecutive water sorption cycles. Its low isosteric heat of adsorption (~48 kJ mol−1) allows for energy-efficient regeneration at low temperatures. Thus, with the above-mentioned factors considered, COF-432 is among the best materials for water sorption applications, such as to deliver water which can be used for human consumption or irrigation of crops. Additionally, the COF can be used in heat pumps, dehumidifiers, adsorption refrigerators and solar cooling systems.

In an aspect the invention provides composition comprising a porous covalent organic framework (COF) with two- or three-dimensional (2-D or 3-D) topologies (hcb, sql, kgm, fxt, kgd, or bex for 2-D; dia, ctn, bor, pts, lon, srs, ffc, or rra for 3-D) for atmospheric water harvesting, comprising a crystalline framework comprising a linkage selected from imine, amide, imide, hydrazone, azine, imidazole, benzoxazole, β-ketoenamine, and olefin, generated from a combination of at least two different linkers selected from: ditopic linkers, tritopic linkers, tetratopic linkers, hexatopic linkers, and octatopic linkers. See, e.g. FIG. 5-6; the topologies (3-letter symbols) are well-defined by in reticular chemistry.[24]

In embodiments:

the combination is tetratopic and tritopic linkers;

the linkage is imine (—CH═N—); and/or the composition is constructed from tetratopic 1,1,2,2-tetrakis(4-aminophenyl)ethene [ETTA, $C_{26}H_{16}(NH_2)_4$] and tritopic 1,3,5-triformylbenzene [TFB, $C_6H_3(CHO)_3$], termed COF-432 {$[(ETTA)_3(TFB)_4]_{imine}$}, which exhibits the mtf topology.

In an aspect the invention provides a device comprising a disclosed water sorption composition, such as an atmospheric water harvester, heat pump, dehumidifier, adsorption refrigerator and solar cooling system.

In an aspect the invention provides a disclosed composition comprising the step of condensing the different linkers to form the crystalline framework.

In an aspect the invention provides a disclosed composition comprising contacting the compositing with air under conditions wherein the composition adsorbs water from the air, preferably where in the air has a relative humidity of 20-40%.

Aspect 2. Robust Covalent Organic Frameworks for Capturing $CO_2$ and $H_2O$ from Air and Flue Gas The invention provides compositions comprising one or more chemically and thermally stable covalent organic framework (COF) materials configured and operative as solid adsorbents for capturing carbon dioxide, and optionally water, from gases like air or a post-combustion exhaust gas mixtures. In all variations, the backbone building unit composition, non-backbone functional groups, the linkage, and the topology, regardless of their synthetic processes, are provided. In most variations, the COF materials are provided to be suitable for PCC, or DAC, or both processes, but not limited to the two specific processes. The criteria (such as "robustness" for different scenarios) and characterization methods are provided as part of this disclosure. In some variations, the COF materials have high affinity to $H_2O$, such that in scenarios where the gas mixture contains $H_2O$ (such as ambient air), the $CO_2$ capture capacity of the COF material is increased, unchanged, or only slight decreased. In such variations, the COF materials are suitable for capturing $CO_2$ and harvesting water at the same time. This approach enables development of such materials as an energy- and cost-effective solution for capturing $CO_2$ from air and from post-combustion gas mixtures, and provides solutions for integrative capture of $CO_2$ and $H_2O$ at the same time where water is in substantial shortage as well.

In an aspect, the invention provides a composition comprising a chemically and thermally stable covalent organic framework (COF) material configured and operative as a solid adsorbent for capturing carbon dioxide from air or a post-combustion exhaust gas mixture, and comprising organic building blocks defined in FIG. 1, in which the substituents are defined in FIG. 2, with side chains defined in the same fashions in FIGS. 1 and 2, linked by the linkages defined in FIG. 4, and all possible topologies (the layered topologies of sql, hcb, hxl, kgm, bex, kgd, tth or mtf and 3D topologies of dia, lon, pcu, srs, pto, pts, tbo, bor, cnt or dia-w are examples of such topologies), such as shown in FIG. 5.

Excluded are COFs and linkages that are not chemically or thermally stable in conditions for $CO_2$ capture from air or a post-combustion exhaust gas mixture. Hence, our invention is limited to the confined range of COFs as defined in our claims, including being characterized as (1) chemically and thermally stable, as confirmed by characterization, and (2) operative and configured for $CO_2$ capture from air and post-combustion exhaust gas mixture.

In embodiments:

the composition is contained in a matrix configured as a sorption bed, fluidized bed, coated heat exchanger, or membrane, optionally, in a fluid flow path configured to pass the air or mixture over, around and/or through the matrix;

the composition comprises the air or post-combustion exhaust gas mixture, wherein water is present in the air or mixture, and the material is configured and is operative to harvest the water from the air or mixture, and provides facile collection of water as a second value-delivering function, wherein in this embodiment, the harvesting of water is a potential byproduct when water is present in the gas mixture the COF has a structure disclosed herein; and/or the COF is selected from COF-366-F-CoCOF-316, COF-316-$CONH_2$, COF-316-C(NOH)$NH_2$, and COF-701.

In an aspect the invention provides a system for capturing carbon dioxide from air or a post-combustion exhaust gas mixture comprising a matrix, such as a sorption bed containing a subject composition configured as a solid adsorbent for capturing the carbon dioxide, and optionally water, from the air or mixture.

In an aspect, the invention provides a method comprising using a subject composition as a solid adsorbent for capturing carbon dioxide, and optionally water, from air or a post-combustion exhaust gas mixture.

Aspect 3. Enhanced Water Harvesting by Charged Covalent Organic Frameworks

The invention provides methods, compositions and systems to increase the water uptake capacity of COFs under low and medium RH, while simultaneously increasing their water uptake rate. Unlike conventional COFs with charge neutral backbones, the disclosed COFs contain cationic or anionic backbones with counter ions locating inside the pore, which counter ion may be organic or metallic.

The subject COF materials can be utilized for water harvesting from air. The collected water can be used for human consumption and irrigation. In addition, these materials can be deployed in other water sorption based applications, such as in heat pumps, dehumidifiers, adsorption refrigerators, solar cooling systems, dryers, organic light emitting devices and secondary battery devices.

In an aspect, the invention provides a composition comprising charged, water-stable covalent organic framework (COF) material configured and operative for water sorption or harvesting from a gas, such as air or an exhaust, and comprising a cationic or anionic backbone forming pores, and organic or metallic counter ions inside the pores.

In embodiments:

the composition comprises a charged functional group of (herein, e.g. Table 1) a counter ion (herein, e.g. Table 2), an organic linkage (herein, e.g. Table 3), and an organic linker (herein, e.g. Table 4);

the composition is contained in a matrix configured as a sorption bed, fluidized bed, coated heat exchanger, or membrane;

the composition is contained in a matrix configured as a sorption bed, fluidized bed, coated heat exchanger, or membrane, in a fluid flow path configured to pass the air or exhaust over, around and/or through the matrix;

the composition comprises the air or exhaust, wherein water is present in the air or exhaust; and/or the COF comprises a structure particularly disclosed herein.

In an aspect, the invention provides a system for enhanced water harvesting or for capturing water from a gas, such as air or an exhaust, containing a subject composition, configured as a solid adsorbent for capturing the water from the gas, wherein the composition provides increased water uptake capacity under low and medium relative humidity levels, while simultaneously increasing water uptake rate.

In an aspect the invention provides a subject composition as a solid adsorbent for capturing water from a gas, such as air an exhaust, wherein the composition provides increased water uptake capacity under low and medium relative humidity levels, while simultaneously increasing water uptake rate.

The invention encompasses all combination of the particular aspects and embodiments recited herein, as if each combination had been laboriously recited.

BRIEF DESCRIPTION OF THE DRAWINGS

FIG. 37. Comparison of PXRD patterns, FT-IR spectra, and $N_2$ isotherms at 77 K of pristine, 6 M HCl and 6 M NaOH treated COF-316.

FIG. 38. $CO_2$ isotherm at 273 K compared to $CH_4$ and $N_2$ for COF-316 (JUC-505).

FIG. 39. Schematic representation of COF-701.

DESCRIPTION OF PARTICULAR EMBODIMENTS OF THE INVENTION

Figure 1A:
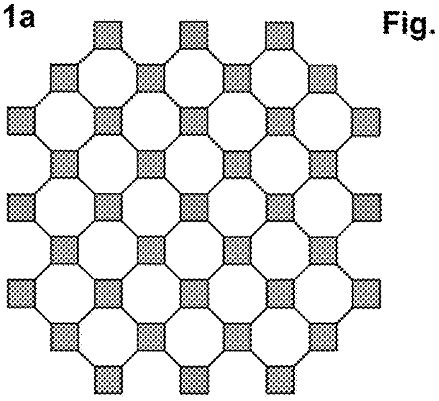
FIGS. 1*a*-1*b*. Juxtaposition of the 4-c uninodal sql net (a) and the (3,4,4)-c trinodal mtf net (b). The mtf net is conceptually constructed by removing ⅛ of the nodes (orange) from the sql net, and can be perceived as a voided sql net. The nodes in both nets are depicted as squares. Blue squares represent 4-c and yellow squares 3-c nodes.

Unless contraindicated or noted otherwise, in these descriptions and throughout this specification, the terms "a" and "an" mean one or more, the term "or" means and/or. The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Aspect 1. Porous Covalent Organic Frameworks for Atmospheric Water Harvesting Developing new materials for water harvesting from air is an important endeavor in addressing the global water crisis: Ideally, such materials should have: (i) high, hydrolytic stability and retention of capacity upon long-term water uptake and release cycling, (ii) an 'S'-shaped water sorption isotherm with a steep pore-filling step (IUPAC Type IV or V) at low relative humidity (<40% relative humidity, RH) with minimal to no hysteresis, and (iii) a low regeneration temperature to allow for use of low-grade heating to enable facile release of water molecules from the material.[2]

Reticular structures, that is metal-organic frameworks (MOFs) and covalent organic frameworks (COFs), are ideally suited to address the water shortage crisis because of their exceptional porosity, as well as the large diversity of chemical compositions and accessible topologies; aspects that allow to tune their water sorption properties in a great variety of ways.[2,3] Indeed, MOFs have been identified, studied, and practically employed for water harvesting from air.[2,4-9] COFs, however, remain largely unexplored for this application.[10] This could potentially be explained by the relatively lower crystallinity exhibited by COFs, in particular those constructed from hydrolytically robust linkages,[11] which precludes the formation of highly ordered molecular water networks within the porous framework—an important pre-requisite for obtaining 'S'-shaped water isotherm profiles.

Herein, we sought to explore COFs as water harvesting materials. In a detailed example we report a new, highly crystalline framework, constructed from the tetratopic 1,1,2,2-tetrakis(4-aminophenyl)ethene [ETTA, $C_{26}H_{16}(NH_2)_4$] and the tritopic 1,3,5-triformylbenzene [TFB, $C_6H_3(CHO)_3$], termed COF-432 $\{[(ETTA)_3(TFB)_4]_{imine}\}$, which exhibits the mtf topology—a net hitherto not reported in COF chemistry (FIG. 1).[11-13] This COF displays a water sorption isotherm without hysteretic behavior and with a steep pore-filling step at low relative humidity (<40% RH), exceptionally high water sorption cycling stability, and a low heat of adsorption. All these factors establish COF-432 as a long-term hydrolytically stable water harvesting material with a low regeneration energy barrier and relatively high working capacity within a small partial pressure range; with the latter enabling efficient use of a small temperature gradient for water uptake and release cycling.

Figure 2A:
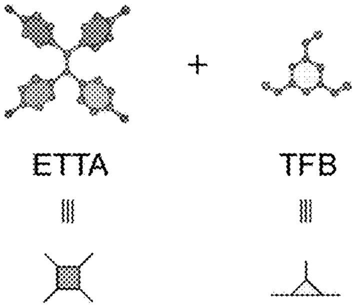
FIGS. 2*a*-2*c*. The reaction of 1,1,2,2-tetrakis(4-aminophenyl) ethene (ETTA) and 1,3,5-triformylbenzene (TFB) (a), which represent a 4-c and a 3-c node, respectively, yields COF-432 (c). This framework exhibits the (3,4,4)-c mtf topology, shown in its augmented form (b). Atom colors: C, gray; N, blue; O, red. H atoms are omitted for clarity. The second layer of the staggered structure of COF-432 is depicted in light orange.
Figure 2B:
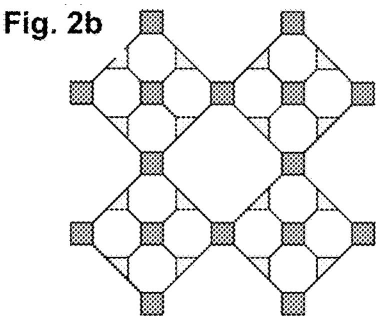

COF-432 was synthesized solvothermally through the condensation of ETTA and TFB in a mixture of chloroform, methanol, and aqueous acetic acid (FIG. 2, Supporting Information, SI, Section S2). The structure of COF-432 was determined by powder X-ray diffraction (PXRD) and supported by elemental analysis (EA), Fourier-transform infrared (FTIR) spectroscopy, $^{13}C$ cross-polarization magic angle spinning nuclear magnetic resonance (CP-MAS NMR) spectroscopy, thermogravimetric analysis (TGA) and $N_2$ sorption analysis. FTIR spectroscopy of COF-432 showed the absence of aldehyde ($\nu_{C=O}$=1692 $cm^{-1}$) and amine ($\nu_{N-H}$=3352 $cm^{-1}$) stretches, present in the starting materials ETTA and TFB. Also, the emergence of an imine ($\nu_{C=N}$ =1628 $cm^{-1}$) stretch indicated the formation of an extended imine-linked network (SI, Section S3). Formation of the imine linkage was further corroborated by $^{13}C$ CP-MAS NMR spectroscopy, in which a characteristic $^{13}C$ imine resonance was observed at 158 ppm (SI, Section S4).

Figure 1B:
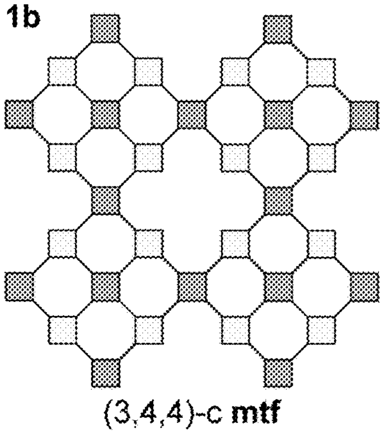

Due to the small crystal size (ca. 100×100×300 $nm^3$, SI, Section S5) of COF-432, its structure was determined by analysis of its PXRD pattern (SI, Section S6). Indexing of the PXRD pattern using TOPAS 4.2 software[14] identified the space group $14_1/a$ (No. 88). Next, a Charge Flipping method[15] was used to calculate the electron density map (EDM) of COF-432, generating a valid result in the respective space group. Finally, the structure of COF-432 was determined by locating the fragments of ETTA observed in the EDM (SI, Section S6) and linking those into an extended network. In this structure, the ETTA and TFB building units (FIG. 2*a*) are connected through imine bonds to form an extended two-dimensional (2D) framework of mtf topology with three kind of vertices and two kind of edges (FIG. 1, 2*b*, SI, Section S7). Interestingly, this 2D net topology deviates from a possibly expected 3D net[12] or recently reported 2D bex topology[16] for the combination of a triangular and a rectangular tetratopic linker, thus extending the scope of observed topologies in COF chemistry. The unit cell parameters of COF-432 were refined by the Le Bail method using wide-angle X-ray scattering (WAXS) data ($I4_1/a$; a=30.65 Å, c=12.85 Å) with residual factors of $R_p$=2.88% and $R_{wp}$=3.96% (FIG. 3; SI, Section 6).

Figure 2C:
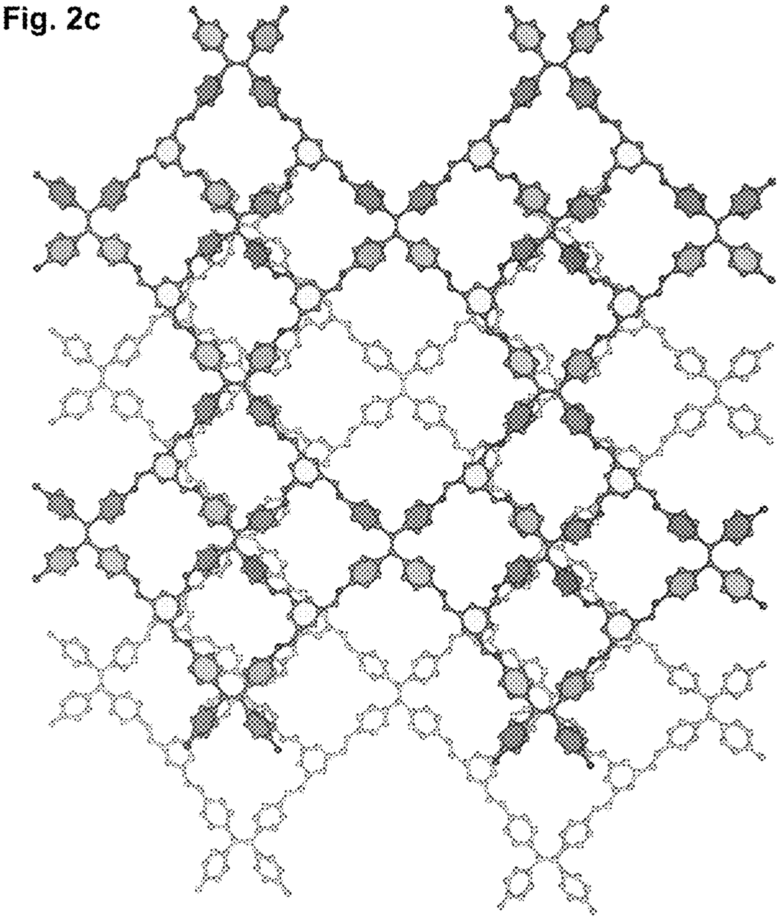

A single layer of COF-432 (FIG. 2*c*) has two kind of square pore apertures with diameters of ca. 10.0 Å and 21.0 Å (based on van der Waals radii). Adjacent 2D layers are staggered, thus creating a 1D cylindrical pore structure with a diameter of ca. 7.5 Å (FIG. 2*c*). COF-432 is permanently porous with a BET surface area of 895 $m^2$ $g^{-1}$. This is close to the theoretical value calculated from the structural model (900 $m^2$ $g^{-1}$), approximated by its molecularly accessible area using $N_2$ as the probe adsorbate (kinetic diameter=3.6 Å).[17] The pore volume of COF-432, determined from its $N_2$ sorption isotherm (0.43 $cm^3$ $g^{-1}$), is in good agreement with the pore volume predicted from its structural model using the Void Calculation function in PLATON (0.45 $cm^3$ $g^{-1}$). Additionally, the pore size distribution of COF-432 calculated from its $N_2$ sorption isotherm indicates a single pore with a diameter of 8.0 Å, which is in good agreement with the proposed crystal structure (SI, Section S8). The structural model is further confirmed by elemental analysis of COF-432, which matches well with the expected elemental ratio calculated for the framework (SI, Section S2).

The hydrolytic stability of COF-432 was initially investigated by immersing the activated COF in water. PXRD patterns of COF-432 before and after exposure demonstrated that the material retained its crystallinity for at least 20 d. Additionally, the material did not lose its surface area after extended soaking of the COF in water (90 h under stirring; SI, Section S10). This exceptional hydrolytic stability of the imine-based COF encouraged us to study its water sorption properties.

Figure 4A:
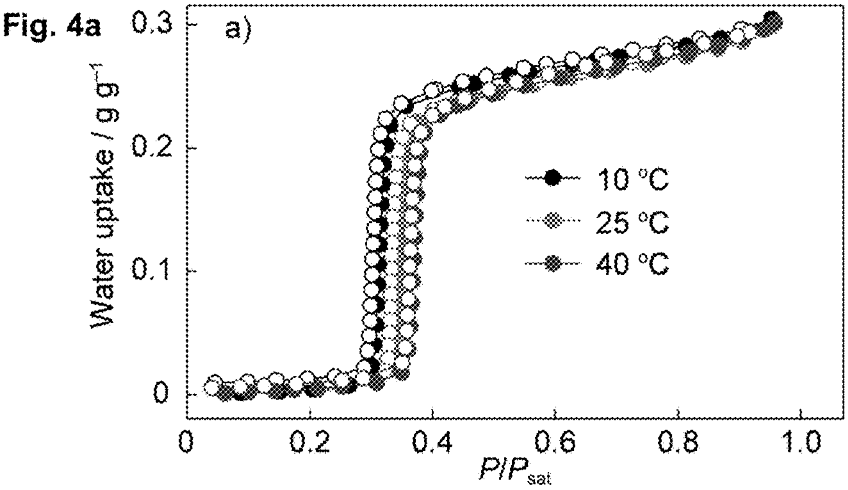
FIGS. 4*a*-4*b*. (a) Water sorption analysis on COF-432, measured at different temperatures (10, 25 and 40° C.). P: water vapor pressure. $P_{sat}$: saturation water vapor pressure at the given temperature. (b) Water cycling stability test for 300 adsorption-desorption cycles conducted on COF-432 at constant water vapor pressure (1.7 kPa). Adsorption and desorption are carried out at 30° C. (40% relative humidity, RH) and 35° C. (30% RH), respectively.

COF-432 exhibits an 'S'-shaped water sorption isotherm with a steep pore-filling step at 34% RH (at 25 ° C.; FIG. 4*a*). The maximal water uptake at $PIP_{sat}$=0.95 reaches 30 wt % (0.3 g $g_{COF}^{1}$) and the working capacity in the relative humidity range between 20 and 40% is 0.23 g $g_{COF}^{-1}$. We note that selected reported MOFs exhibit a higher water uptake capacity than COF-432,[2] nevertheless, we strongly believe that extending the scope of material classes suitable for atmospheric water harvesting will be of great benefit to this technology. Unlike other COFs, COF-432 does not exhibit hysteretic water sorption behavior. This is an attractive feature because it restricts the energy requirement for regeneration of this material. To further study the interaction of the water molecules with the COF, water sorption isotherms at different temperatures (10, 25, and 40° C.; FIG. 4*a*) were used to calculate the isosteric heat of adsorption ($Q_{st}$) of water in COF-432. It was estimated to account to ca. 48 kJ $mol^{-1}$ (SI, Section S11)—close to the evaporation enthalpy of water (44 kJ $mol^{-1}$ at 25° C.). This indicates that water-water interactions are predominant during the pore filling process.[2] Indeed, the pore surface of COF-432 is mostly non-polar and the pore-filling step at low relative humidity (<40% RH) is likely caused by the strong confinement effect in the small framework.

Figure 4B:
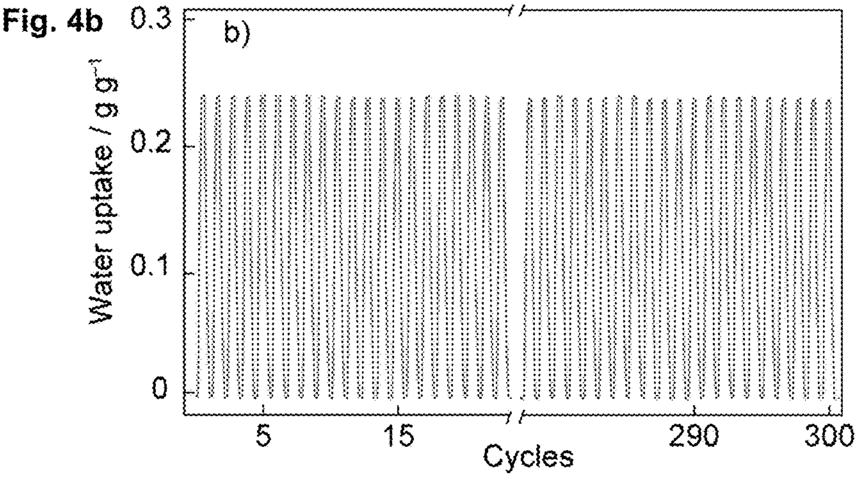

Importantly, COF-432 retained its crystallinity, BET surface area and water vapor capacity after 7 consecutive water sorption measurements (SI, Section S12)—an impressive feat considering that other COFs reported as promising water sorbents in the literature exhibit a decrease in surface area after water exposure and/or sorption.[20-23] These findings encouraged us to subject COF-432 to a long-term water adsorption-desorption cycling test: In a thermogravimetric analyzer, the framework was exposed to water vapor under isobaric conditions (1.7 kPa), and a temperature swing between 30 and 35° C. (corresponding to 40 and 30% RH, respectively) was applied to trigger water ad- and desorption. The steep pore-filling step allowed for a high working capacity of 0.23 g $g_{COF}^{-1}$ under employment of an ultra-low temperature gradient (5° C.). In total, 300 uptake and release cycles were conducted, and the working capacity remained unchanged during the experiment (FIG. 4*b*), indicating retention of porosity and thus exceptional water cycling stability.

We have synthesized new COF framework, such as COF-432, which exhibit attractive water sorption properties, including (i) exceptional long-term stability upon water uptake and release cycling, (ii) a hysteresis-free water sorption isotherm with a steep uptake step at low relative humidity, and (iii) low heat of adsorption, allowing for regeneration by low-grade energy sources, providing suitable materials for water harvesting from air, and in heat pump systems or in desiccant-based dehumidifiers.

REFERENCES

1. Wahlgren, R. V. Atmospheric water vapour processor designs for potable water production: A review. *Water Res.* 2001, 35, 1-22.

2. Kalmutzki, M. J.; Diercks, C. S.; Yaghi, O. M. Metal-organic frameworks for water harvesting from air. *Adv. Mater.* 2018, 30, 1704304.

3. Yaghi, O. M.; Kalmutzki, M. J.; Diercks, C. S. Introduction to Reticular Chemistry: Metal-organic frameworks and covalent organic frameworks, *Wiley-VCH, Weinheim,* 2019, 509.

4. Burtch, N. C.; Jasuja, H.; Walton, K. S. Water stability and adsorption in metal-organic frameworks. *Chem. Rev.* 2014, 114, 10575-10612.

5. Rieth, A. J.; Yang, S.; Wang, E. N.; Dincă, M. Record atmospheric fresh water capture and heat transfer with a material operating at the water uptake reversibility limit. *ACS Cent. Sci.* 2017, 3, 668-672.

6. Kim, H.; Yang, S.; Rao, S. R.; Narayanan, S.; Kapustin, E. A.; Furukawa, H.; Umans, A. S.; Yaghi, O. M.; Wang, E. N. Water harvesting from air with metal-organic frameworks powered by natural sunlight. *Science,* 2017, 356, 430-434.

7. Kim, H.; Rao, S. R.; Kapustin, E. A.; Zhao, L.; Yang, S.; Yaghi, O. M.; Wang, E. N. Adsorption-based atmospheric water harvesting device for arid climates. *Nat. Commun.* 2018, 9, 1191.

8. Fathieh, F.; Kalmutzki, M. J.; Kapustin, E. A.; Waller, P. J.; Yang, J.; Yaghi, O. M. Practical water production from desert Air. *Sci. Adv.,* 2018, 4, eaat3198.

9. Hanikel, N.; Prévot, M. S.; Fathieh, F.; Kapustin, E. A.; Lyu, H.; Wang, H.; Diercks, N. J.; Glover, T. G.; Yaghi, O. M. Rapid cycling and exceptional yield in a metal-organic frame-work water harvester. *ACS Cent. Sci.* 2019, 5, 1699-1706.

10. Byun, Y.; Je, S. H.; Talapaneni, S. N.; Coskun, A. Advances in porous organic polymers for efficient water capture. *Chem. Eur. J.* 2019, 25, 10262-10283.

11. Lohse, M. S.; Bein, T. Covalent organic frameworks: Structures, synthesis, and applications. *Adv. Funct. Mater.* 2018, 28, 1705553.

12. Lan, Y.; Han, X.; Tong, M.; Huang, H.; Yang, Q.; Liu, D.; Zhao, X.; Zhong, C. Materials genomics methods for high-throughput construction of COFs and targeted synthesis. *Nat. Commun.* 2018, 9, 5274.

13. Lyle, S. J.; Waller, P. J.; Yaghi, O. M. Covalent organic frameworks: Organic chemistry extended into two and three dimensions. *Trends Chem.* 2019, 1, 172-184.

14. Bruker AXS GmbH, TOPAS Manual: DOC-M88-EXX065 V4.2-01.2009.

15. Palatinus, L.; Chapuis, G. SUPERFLIP-A Computer program for the solution of crystal structures by charge flipping in arbitrary dimensions. *J. Appl. Crystallogr.* 2007, 40, 786-790.

16. Banerjee, T.; Haase, F.; Trenker, S.; Biswal, B. P.; Savasci, G.; Duppel, V.; Moudrakovski, I.; Ochsenfeld, C.; Lotsch, B. V. Sub-stoichiometric 2D covalent organic frameworks from tri- and tetratopic linkers. *Nat. Commun.* 2019, 10, 2689.

17. Duren, T.; et al, Calculating geometric surface areas as a characterization tool for metal-organic frameworks. *J. Phys. Chem. C* 2007, 111, 15350-15356.

18. Furukawa, H.; Gándara, F.; Zhang, Y. B.; Jiang, J.; Queen, W. L.; Hudson, M. R.; Yaghi, O. M. Water adsorption in porous metal-organic frameworks and related materials. *J. Am. Chem. Soc.* 2014, 136, 4369-4381.

19. Canivet, J.; et al. Structure—property relationships of water adsorption in metal-organic frameworks. *New J. Chem.* 2014, 38, 3102-3111.

20. Biswal, B. P.; et al. Pore surface engineering in porous, chemically stable covalent organic frameworks for water adsorption. *J. Mater. Chem. A* 2015, 3, 23664-23669.

21. Stegbauer, L.; Hahn, M. W.; Jentys, A.; Savasci, G.; Ochsenfeld, C.; Lercher, J. A.; Lotsch, B. V.; Tunable water and $CO_2$ absorption properties in isostructural azine-based covalent organic frameworks through polarity engineering. *Chem. Mater.* 2015, 27, 7874-7881.

22. Karak, S.; et al. Constructing ultraporous covalent organic frameworks in seconds via an organic terracotta process. *J. Am. Chem. Soc.* 2017, 139, 1856-1862.

23. Pérez-carvajal, J.; et al. The imine-based COF TpPa-1 as an efficient cooling adsorbent that can be regenerated by heat or light. *Adv. Energy Mater.* 2019, 1901535.

24. O'Keeffe, M.; Peskov, M. A.; Ramsden, S. J.; Yaghi, O. M. The reticular chemistry structure resource (RCSR) database of, and symbols for, crystal nets. *Acc. Chem. Res.* 2008, 41, 1782-1789.

Analytical techniques. Elemental microanalyses (EA) were performed by using a LECO CHNS-932 CHNS elemental analyzer (Section S2). Fourier-transform infrared (FTIR) spectra were collected using a Bruker ALPHA Platinum ATR-FTIR Spectrometer equipped with a single reflection diamond ATR module (Section S3). Solid-state nuclear magnetic resonance (NMR) spectra were collected using a 7.05 T magnet with a Tecmag Discovery spectrometer operating at 300.13 MHz for $^1H$ and 75.48 MHz for $^{13}C$ (Section S4). Scanning electron microscopy (SEM) images were recorded on a FEI Quanta 3D FEG scanning electron microscope with an accelerating voltage of 10 kV and a working distance of 10.0 mm (Section S5). Powder X-ray diffraction (PXRD) data was collected on a Bruker D8 Advance diffractometer (Bragg-Brentano geometry) employing Ni filtered Cu Kα (λ=1.54059 A) radiation (Section S6). Wide-angle X-ray scattering (WAXS) patterns were acquired on beamline 7.3.3 at the Advanced Light Source (ALS) with a Pilatus 2M detector (Section S6). $N_2$ sorption measurements were carried out on a Micromeritics 3Flex Surface Characterization Analyzer (Section S8) and ASAP 2420 System (Section 10). A liquid $N_2$ bath was used for measurements at 77 K. Thermogravimetric analysis (TGA) curves were recorded on a TA Q500 thermal analysis system under dry $N_2$ flow (Section S9).

Water sorption isotherms were measured on a BEL Japan BELSORP-aqua3 (Section 11). The water (analyte) was degassed through five freeze-pump-thaw cycles before the sorption experiment. The measurement temperature was controlled using a water circulator. The water adsorption-desorption cycling stability (Section 12) was probed with a TA Instruments SDT Q600 series thermal gravimetric analyzer (TGA). The primary gas inlet was connected to a dry nitrogen tank. The secondary gas inlet was used to supply humidified nitrogen, which was generated by passing dry nitrogen gas through a gas washing bottle (2 L) filled with water. The temperature and relative humidity (RH) were monitored using high-accuracy thermocouples and humidity sensors downstream the TGA chamber. The desired RH was achieved by adjusting the ratio of dry to humidified nitrogen gas flow, while maintaining the sum of both flows constant at 250 mL $min^{-1}$.

Synthesis of 1,1,2,2-Tetrakis(4-aminophenyl) ethene (ETTA). 1,1,2,2-Tetrakis(4-aminophenyl) ethene (ETTA) was synthesized according to a previously reported procedure.[1]

Synthesis and activation of COF-432. A Pyrex tube measuring 10×8 mm (o.d×i.d) was charged with ETTA (12 mg, 0.031 mmol), triformylbenzene (TFB) (7.3 mg, 0.046 mmol), and a mixture of chloroform/methanol (0.6:0.4 mL). The solution was then sonicated for 5 min before addition of aqueous acetic acid (0.2 mL, 6M). The tube was flash-frozen at 77 K under liquid $N_2$, evacuated to an internal pressure of 100 mTorr and flame-sealed to a length of ca. 15 cm. The reaction was heated to 120° C. for 3 d yielding a yellow solid, namely COF-432, that was isolated by filtration, washed 5 times with methanol, and solvent-exchanged with chloroform in a Soxhlet extractor for 24 h. COF-432 was then activated under dynamic vacuum at room temperature for 3 h followed by dynamic vacuum at 85° C. for 12 h. EA of COF-432: Calcd. for $C_{114}H_{72}N_{12}.6H_2O$: C, 79.70; H, 4.93; N, 9.78%. Found: C, 78.35; H, 4.94; N, 10.01%.

PXRD data collection. PXRD measurements were carried out using a Bruker D8 Advance diffractometer in reflectance Bragg-Brentano geometry employing Ni filtered Cu Kα focused radiation (1.54059 Å, 1.54439 Å) at 1600 W (40 kV, 40 mA) power, which was equipped with a LynxEye detector. The best counting statistics were achieved by collecting samples using a 0.02°2θ step scan from 3-50° with an exposure time of 10 s per step. The measurement was performed at room temperature and atmospheric pressure.

Structural elucidation of COF-432: Unit cell determination. The unit cell parameters were determined by indexing the PXRD pattern with TOPAS 4.2.[2] A body-centered tetragonal lattice with the space group $I4_1/a$ (No. 88) was found for COF-432. Whole pattern profile fitting and extraction of the integrated intensities was carried out using data from 2θ=5–50° . A background correction was performed using a 20-parameter Chebyschev polynomial function.

Electron density calculation. A charge flipping method executed via Superflip[3] was used to calculate the electron density maps of COF-432. The PXRD pattern were first indexed and a tetragonal crystal lattice was obtained which was then refined by a Pawley fit. The input parameters in Superflip allowed to calculate the electron density map in the P1 space group. The converged results were obtained with a success rate of 70% proposing the $I4_1/a$ space group.

Structural model. A structural model of COF-432 was generated by using the Materials Visualizer module within Materials Studio (Material Studio ver. 7.0, Accelrys Software Inc.) as follows: The ETTA linker was first located at the positions indicated by the electron density map. ETTA linkers were then linked by the TFB building units. Due to the symmetry of $I4_1/a$, one of the ETTA building units was disordered. Upon completion of the structural model, an energetic minimization was performed using a universal force field implemented in the Forcite module of Materials Studio. During this process, the unit cell parameters were also optimized until proper convergence was achieved (energy convergence criteria were set at $10^{-4}$ kcal $mol^{-1}$).

Structural model refinement. A full profile pattern fitting based on the Le Bail method from 2θ=2–45° was performed on the experimental WAXS pattern. The calculated PXRD pattern achieved satisfactory agreement with the experimental PXRD pattern, as demonstrated by the fitting that converged with low residual values ($R_{wp}$ =3.96%, $R_p$=2.88%) to yield the final unit cell parameters (a=30.65 Å, c=12.85 Å).

The fractional atomic coordinates and refined unit cell parameters for COF-432 can be found in Table S1. Further crystallographic information is provided in Table S2.

TABLE S1

Atomic coordinates and refined unit cell parameters of COF-432.

| | |
|---|---|
| Name | COF-432 |
| Space Group | $I4_1/a$ (No. 88) |
| a (Å) | 30.65 |
| c (Å) | 12.85 |
| Unit Cell Volume ($Å^3$) | 12075 |

| Atom Name | Occupancy | x | y | z |
|---|---|---|---|---|
| H1 | 1 | 0.3760 | 0.9299 | 0.5974 |
| H2 | 1 | 0.2126 | 1.0317 | 0.6280 |
| H3 | 1 | 0.2599 | 0.8984 | 0.5919 |
| H4 | 1 | 0.1549 | 0.9622 | 0.6199 |
| H5 | 1 | 0.3334 | 1.1720 | 0.7559 |
| H6 | 1 | 0.3850 | 1.2318 | 0.7836 |
| H7 | 1 | 0.4825 | 1.1624 | 0.6172 |
| H8 | 1 | 0.4339 | 1.0993 | 0.6095 |
| H9 | 1 | 0.1521 | 0.8160 | 0.4797 |
| H10 | 1 | 0.0881 | 0.7685 | 0.4654 |
| H11 | 1 | 0.0162 | 0.8608 | 0.6440 |
| H12 | 1 | 0.0776 | 0.9096 | 0.6475 |
| H13 | 1 | 0.2849 | 1.1056 | 0.6673 |
| H14 | 1 | 0.3542 | 1.0068 | 0.6198 |
| H15 | 1 | 0.4787 | 0.8270 | 0.5155 |
| H16 | 1 | 0.4241 | 0.8832 | 0.5223 |
| H17 | 1 | 0.3398 | 0.7964 | 0.6876 |
| H18 | 1 | 0.3986 | 0.7451 | 0.7058 |
| C1 | 1 | 0.3438 | 0.9161 | 0.6028 |
| C2 | 1 | 0.3065 | 0.9463 | 0.6100 |
| C3 | 1 | 0.2399 | 1.0068 | 0.6266 |
| C4 | 1 | 0.2660 | 0.9327 | 0.6030 |
| C5 | 1 | 0.2301 | 0.9609 | 0.6097 |
| C6 | 1 | 0.1809 | 0.9399 | 0.6016 |
| C7 | 1 | 0.3657 | 1.1686 | 0.7239 |
| C8 | 1 | 0.3968 | 1.2046 | 0.7390 |
| C9 | 1 | 0.4409 | 1.2069 | 0.6978 |
| C10 | 1 | 0.4509 | 1.1661 | 0.6500 |
| C11 | 1 | 0.4211 | 1.1290 | 0.6419 |
| C12 | 1 | 0.3763 | 1.1288 | 0.6723 |
| C13 | 1 | 0.1235 | 0.8690 | 0.5665 |
| C14 | 1 | 0.1226 | 0.8269 | 0.5166 |
| C15 | 1 | 0.0845 | 0.7978 | 0.5103 |
| C16 | 1 | 0.0430 | 0.8054 | 0.5592 |
| C17 | 1 | 0.0445 | 0.8486 | 0.6062 |
| C18 | 1 | 0.0817 | 0.8788 | 0.6084 |
| C19 | 1 | 0.3075 | 1.0767 | 0.6563 |
| C20 | 1 | 0.2860 | 1.0243 | 0.6429 |
| C21 | 1 | 0.3192 | 0.9949 | 0.6242 |
| C22 | 1 | 0.0024 | 0.7742 | 0.5500 |
| C24 | 1 | 0.4460 | 0.7820 | 0.6169 |
| C25 | 1 | 0.4505 | 0.8211 | 0.5613 |
| C26 | 1 | 0.4183 | 0.8532 | 0.5637 |
| C27 | 1 | 0.3779 | 0.8448 | 0.6105 |
| C28 | 1 | 0.3712 | 0.8045 | 0.6557 |
| C29 | 1 | 0.4053 | 0.7749 | 0.6647 |
| N1 | 1 | 0.3393 | 0.8744 | 0.6113 |
| N2 | 1 | 0.3471 | 1.0881 | 0.6554 |
| N3 | 1 | 0.1657 | 0.8969 | 0.5758 |
| C30 | 0.5 | 0.4977 | 0.7727 | 0.6120 |

TABLE S2

Important crystallographic information for COF-432.

| Parameters | COF-432 |
|---|---|
| Empirical formula | $C_{114}H_{72}N_{12}$ |
| Calculated density (g $cm^{-3}$) | 0.875 |
| Symmetry | Tetragonal |
| Space group | $I4_1/a$ |
| a (Å) | 30.65 |
| c (Å) | 12.85 |

TABLE S2-continued

| Important crystallographic information for COF-432. | |
|---|---|
| Parameters | COF-432 |
| Unit Cell Volume (Å$^3$) | 12075 |
| $R_p$ factor (%) | 2.88 |
| $R_{wp}$ factor (%) | 3.96 |
| Wavelength (Å) | 1.2389 |
| Temperature (K) | 298 |
| Angular range 2θ (°) | 2-45 |
| Refining method | Le Bail |
| Refined background model | Chebyschev polynomial of degree 20 |
| Profile shape function | Pearson VII |
| Correction | Zero-shift |

Study of the effect of guest molecules on the PXRD pattern. COF-432 was immersed in methanol and water for 2 days each. The wet samples were then used to collect the WAXS patterns.

Topological Analysis. The topology of COF-432 was determined by the ToposPro software.[4] TFB and ETTA were interpreted as 3-c and 4-c nodes, respectively, which are linked to generate the 2-dimensional (2-D) mtf network. This net has three kind of vertices and two kind of edges, and the vertices are linked into 4- and 8-membered rings.

$N_2$ Sorption Analysis. Permanent porosity of activated COF-432 was shown by $N_2$ sorption analysis at 77 K.

Thermogravimetric Analysis (TGA). Thermal stability of COF-432 was examined by thermogravimetric analysis. COF-432 (4 mg) was heated under nitrogen flow (60 mL $min^{-1}$) from 30 to 800° C. with a gradient of 5° C. $min^{-1}$.

Hydrolytic Stability Tests. Activated COF-432 was soaked in water at room temperature. PXRD analyses were conducted at different time intervals (3, 6, 10 and 20 days). Comparison of the respective PXRD patterns indicates that COF-432 maintains its crystallinity in water for at least 20 d.

References (1) Lu, J.; Zhang, J. Facile synthesis of azo-linked porous organic frameworks via reductive homocoupling for selective $CO_2$ capture. *J. Mater. Chem. A,* 2014, 2, 13831-13834

(2) Bruker AXS GmbH, TOPAS Manual: DOC-M88-EXX065 V4.2-01.2009.

(3) Palatinus, L.; Chapuis, G SUPERFLIP-A Computer program for the solution of crystal structures by charge flipping in arbitrary dimensions. *J. Appl. Crystallogr.* 2007, 40, 786-790.

(4) Blatov, V. A.; Shevchenko, A. P.; Proserpio, D. M. Applied topological analysis of crystal structures with the program package ToposPro. *Cryst. Growth Des.* 2014, 14, 3576-3586.

Aspect 2. Robust Covalent Organic Frameworks for Capturing $CO_2$ and $H_2O$ from Air and Flue Gas The vast amount of anthropogenic emission of carbon dioxide ($CO_2$) has been an ever-increasing factor related to the rise of global climate crisis. It is thus emergent to mitigate the problem by capturing the emitted $CO_2$ with human efforts, generally referred to as carbon capture, given that essential industrial activities, such as energy generation, production, and transportation, are anticipated yet to remain heavily dependent on fossil fuels for an expected long time. Depending on the source of $CO_2$ mixture, the processes of carbon captures are divided into two major categories: (a) post-combustion capture (PCC) from fossil-fuel burning point sources, and (b) direct air capture (DAC) from the ambient atmosphere.

In both scenarios, major challenges exist in the aspects of (a) selective capture of $CO_2$ from gas mixture, (b) efficient capture with maximal sorption capacity and minimal energy penalty, and (c) long-term stable performance of capturing materials. Endowed by such composition and structure, we expect COFs to be among the most promising candidates of solving the above challenges as solid adsorbents, with (a) high affinity and selectivity of $CO_2$ by chemisorption and physisorption achieved by functionalization through organic chemistry; (b) high gravimetric uptake due to exceptionally high specific surface area and generally low density; (c) low energy consumption due to low heat capacity and ease of mass transfer resulting from open framework structures; (d) stability toward water and impurities established by strong, inert covalent bonds in the backbone of the materials. Such properties are hardly achievable at the same time in other classes of materials.

Description of Particular Embodiments of Aspect 2

The invention provides a generalized enabling methodology to achieve and tune $CO_2$ capture performance using chemically and thermally stable covalent organic framework materials (COFs) as solid adsorbent for capturing carbon dioxide from air and post-combustion exhaust gas mixture. The physical and chemical properties of such adsorbents allow for the achievement of high capacity, low energy penalty, and long-term cyclability, with or without moisture and gaseous impurities. In some variations where water is present in the feed gas mixture, the adsorbents are capable of providing harvesting of water from the gas mixture parallel to the process of $CO_2$ capture, such that the system provides facile collection of water as a second value-deliverable function.

The robust covalent organic frameworks are useful as an active and efficient solid adsorbent in carbon capturing processes for direct air capture, post-combustion capture, and for other scenarios, such as $CO_2$ removal from natural gas. Prototypical covalent organic frameworks are described in: (1) Zhang, B.; Wei, M.; Mao, H.; Pei, X.; Alshmimri, S. A.; Reimer, J. A.; Yaghi, O. M. Crystalline Dioxin-Linked Covalent Organic Frameworks from Irreversible Reactions. J. Am. Chem. Soc., 2018, 140, 12715-12719; and (2) Lyu, H.; Diercks, C. S.; Zhu, C.; Yaghi, O. M. Porous Crystalline Olefin-Linked Covalent Organic Frameworks. J. Am. Chem. Soc. 2019, 141, 6848-6852.

Designated Covalent Organic Frameworks

The covalent organic frameworks comprise organic building units linked with linkages into 2D or 3D extended structures. The infinite extension of the linking of variable building units and linkages are defined mathematically by the topologies.

The organic building units are defined, but not limited to, the categories by the number of points of extension in FIG. 1. In the range of definition each instance of organic building units comprises of an organic fragment $R^m$ and m points of extension $L_m$ or $L_b$. The superscript m in $R^m$ describes that fragment $R^m$ possesses m points of extension.

The points of extensions are defined as the covalent bonding between the two atoms in the immediate neighbor of the point of extension. In most variations, such atoms are one in the organic building unit and one in the linkage. In some other variations, the fragment ($R^2$) contains no atoms, and two atoms are both from the linkage. In some other variations, the linkage contains no atoms, and two atoms are both from the organic building units. The points of extensions are either monodentate connections (1 point of extension connects to 1 linkage through 1 covalent bond, labeled as $L_m$) or as bidentate connections (2 points of extension pair up to connect to 1 linkage through 2 covalent bonds in total, each labeled as $L_b$).

The invention encompasses all possible fragments are defined as iterative substitutions of the $R^m$ groups in FIG. 2.

In each instance, any $R^m$ present in the formula of fragment e are substituted to one of the fragments of Rn defined above. This process is iterated until no $R^m$ is present in the structural formula. In some variations, special iterations are executed such as empty R for ring closure, or empty $R^2$ for representation of direct linking of linkages. In some variations, counterions are left out for clearance of representation, but are considered as part of the covalent organic framework material. In some variations, metal compounds are present in the fragments, represented uniformly as M for metal ions, metal complexes (some ligands are only coordinatively bonded to the metal), and metal clusters.

Figure 3:
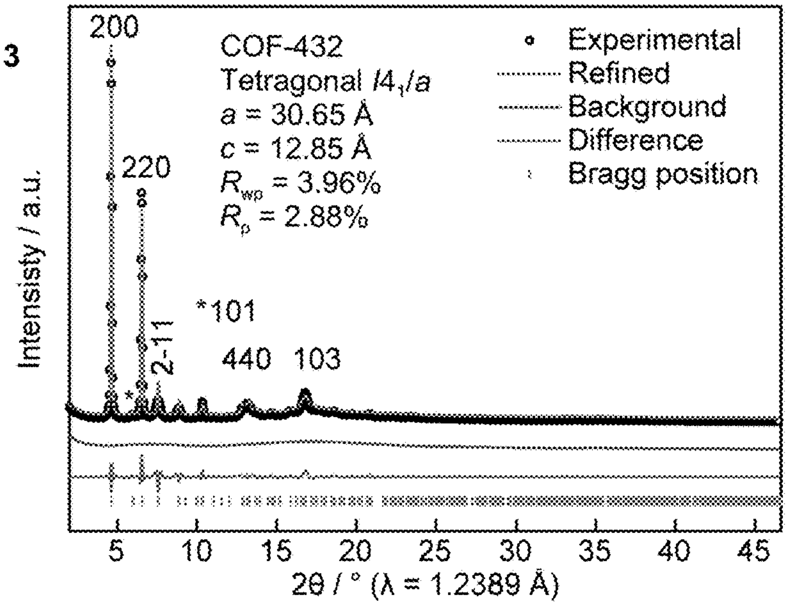
FIG. 3. Wide-angle X-ray scattering (WAXS) pattern and Le Bail analysis of COF-432. The experimental pattern (black), the refined Le Bail fitting (red), the difference plot (green), background (blue), and the Bragg positions (pink) are provided.

Some examples of suitable organic building units are provided in FIG. 3.

The linkages are defined, but not limited to, those specified in FIG. 4.

Figure 5:
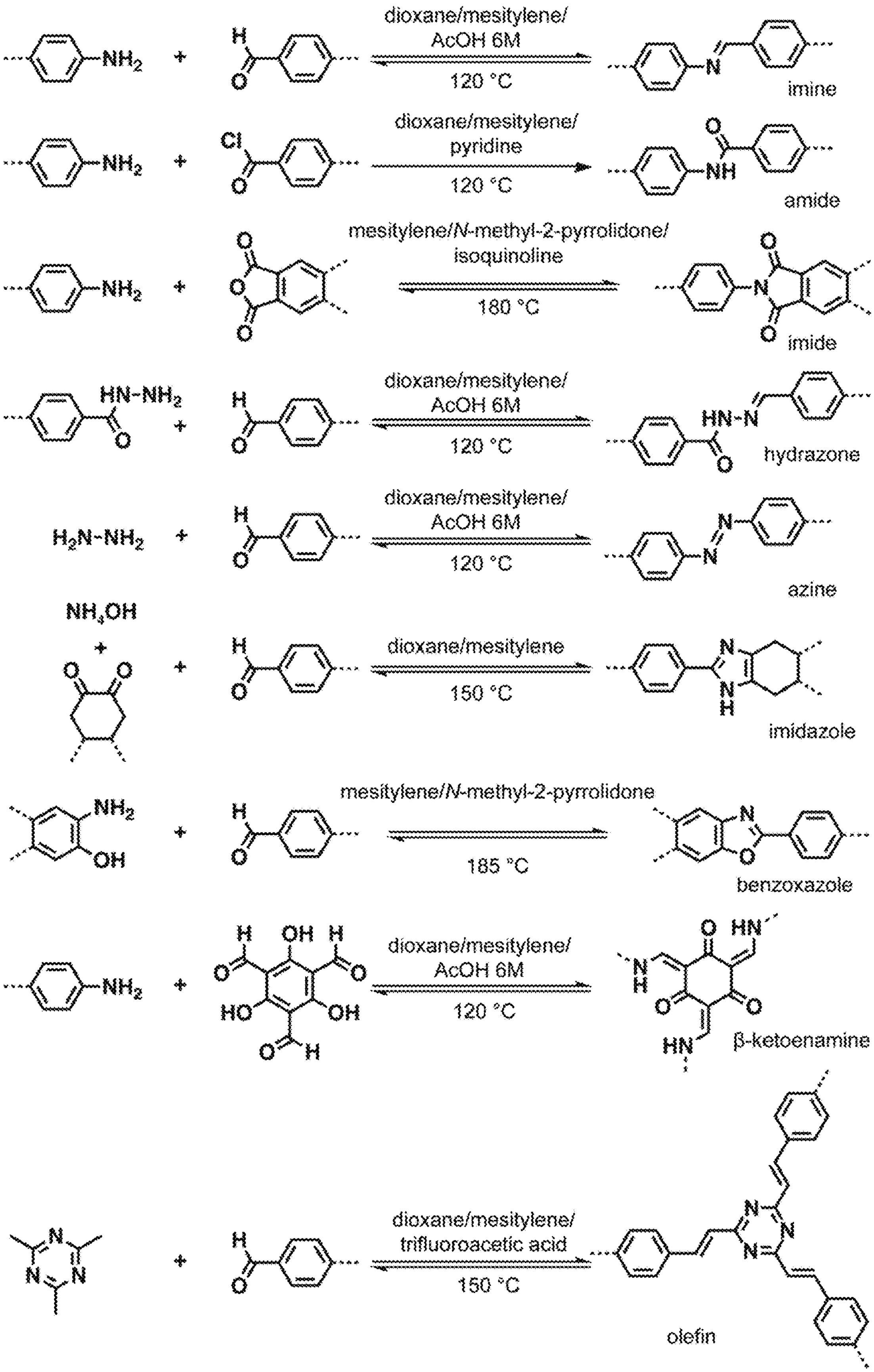
FIG. 5. Synthetic strategies and chemical structures for various linked-COFs including imine, amide, imide, hydrazine, azine, imidazole, benzoxazole, β-ketoenamine, and olefin.

The topology is the mathematical description of the infinite extension of the structure in 1D, 2D and 3D space as open frameworks through covalent bonding between organic building units and linkages. The full definition and description of framework topology is supplied in the Reticular Chemistry Structure Resource (RCSR) database, and the topologies are denoted by net symbols. FIG. 5 provides schematic representations of common examples of topologies in COFs, i.e. sql, hcb, hxl, kgm, kgd, bex, tth, mtf, srs, dia, Ion, bor, ctn, pts, tbo, pto, pcu, dia-w. The topologies of the COFs in this definition are not limited to the range of FIG. 5.

In some variations, the COF contains interpenetrated structures where there exist more than one fold of framework that intercatenate or interlace with other folds of the framework that have the same connectivity. In some variations the COF is comprised of such interpenetration of frameworks but not all folds have the same connectivity.

In some variations, the COFs crystallize in topologies that are derivatives of simple nets. In some of such cases, two (or more) linkers of the same connectivity alternatively occur at equivalent nodes of the topology, described as binary (or trinary, etc.) structures. In some variations, nodes in topologies are replaced with entangled threads, and the building units are therefore closed rings (interlocking structures) or infinitive threads (weaving structures).

In some variations, the COF contains only one kind of building units or linkage at the equivalent positions of nodes or edges in the topology. In other variations, the COF contains more than one kind of building units or linkage at the equivalent positions of nodes or edges in the topology in the same bulk material, but without apparent periodicity. Such COFs are still described with the same topology but termed as multivariate COFs.

In sum, the COFs used in this description are porous, crystalline materials that are comprised within the range of the above-described building blocks, linked through the above-described covalent linkages, and extended with the connectivity of the above-described topologies. Further criteria are described in following sections and defines the range of claim of COFs used in this disclosure.

Characterization of the defined COFs for Carbon Capture in this Disclosure

In all variations, one or the combination of more than one of the techniques including powder X-ray diffraction (PXRD), single-crystal X-ray diffraction (SXRD), wide-angle X-ray scattering (WAXS), small-angle X-ray scattering (SAXS), neutron scattering, electron diffraction (ED), high-resolution transmission electron microscopy (HR-TEM), scanning transmission electron microscopy (STEM), high-resolution scanning electron microscopy (HRSEM), and their technical variations such as grazing-incidence wide-angle X-ray scattering (GIWAXS), is used for confirming the crystallinity, i.e. the periodic structure of the defined composition. In all variations, Bragg diffraction or long-range continuous image of repetitive units should be observed and matched with proposed structural model of the COF.

In all variations, one or the combination of more than one of the techniques including Fourier transform infrared spectroscopy (FT-IR) Raman spectroscopy, UV/Vis spectroscopy, photoluminescence spectroscopy, circular dichroism spectroscopy (CD), and solid-state nuclear magnetic resonance (NMR) are used for confirmation of the chemical composition of the COF. Such spectroscopic signals should indicate the presence of chemical elements, atoms, groups, or structural features. In some variations, isotope-enriched samples of the COF are used in such characterization, and the resultant COF sample should exhibit correspondent isotope effects.

In all variations, one or the combination of more than one of the techniques including gas ($N_2$, $O_2$, Ar, $CO_2$, $H_2O$, other solvent vapor, etc.) sorption experiments and liquid-phase guest uptake experiments, are used to establish the permanent porosity and interior accessibility of the COF material. Isosteric heat ($Q_{st}$) is derived by mathematical fitting of isothermal sorption measurement results of the target gas at different temperatures.

In specific embodiments of COFs for $CO_2$ capture, $CO_2$ uptake at the operation temperature and $CO_2$ partial pressure should be large enough to achieve the desired capture capacity. In some variations where parallel water harvesting is performed, $H_2O$ uptake at the operation temperature and humidity should be large enough to achieve the desired capacity.

In specific embodiments of COFs for $CO_2$ capture with or without parallel water harvesting, thermal and chemical stability are both required for long-term usage as a solid adsorbent.

In all such variations, one or the combination of more than one of the techniques including thermalgravimetric analysis (TGA), TGA-GC, TGA-RGA, and TGA-MS, or other in-situ measurements are used to examine the behavior of the COF in the range of temperature of the operation condition. One or the combination of more than one of the techniques including NMR, FT-IR, GC, GC-MS, XRD, sorption experiments, etc., are used before and after the process to confirm no chemical decomposition, release of compounds (such as undesired guests from the pore), loss of crystallinity or porosity is present.

In all such variations, exposure of the COF to chemicals (such as $CO_2$, $O_2$, $H_2O$, $SO_2$, $SO_3$, NO, $NO_2$, base, acid, oxidants, reductants) used in the preparation, storage, transportation and working conditions, in gas, liquid, solution or solid form, is performed for short and long period to examine the chemical stability of the COF in the range of preparation and usage conditions. One or the combination of more than one of the techniques including NMR, FT-IR, GC, GC-MS, XRD, sorption experiments, etc., are used before and after the process to confirm no chemical decomposition, release of compounds (such as undesired guests from the pore), loss of crystallinity or porosity is present. In most variations, $CO_2$ and $H_2O$ stability are necessary for COFs for capturing $CO_2$ and $H_2O$ from gas mixtures containing $H_2O$. In other variations where $H_2O$ is not present in the preparation, storage, transportation and capturing processes, $H_2O$ stability is not necessarily confirmed.

Figure 6:
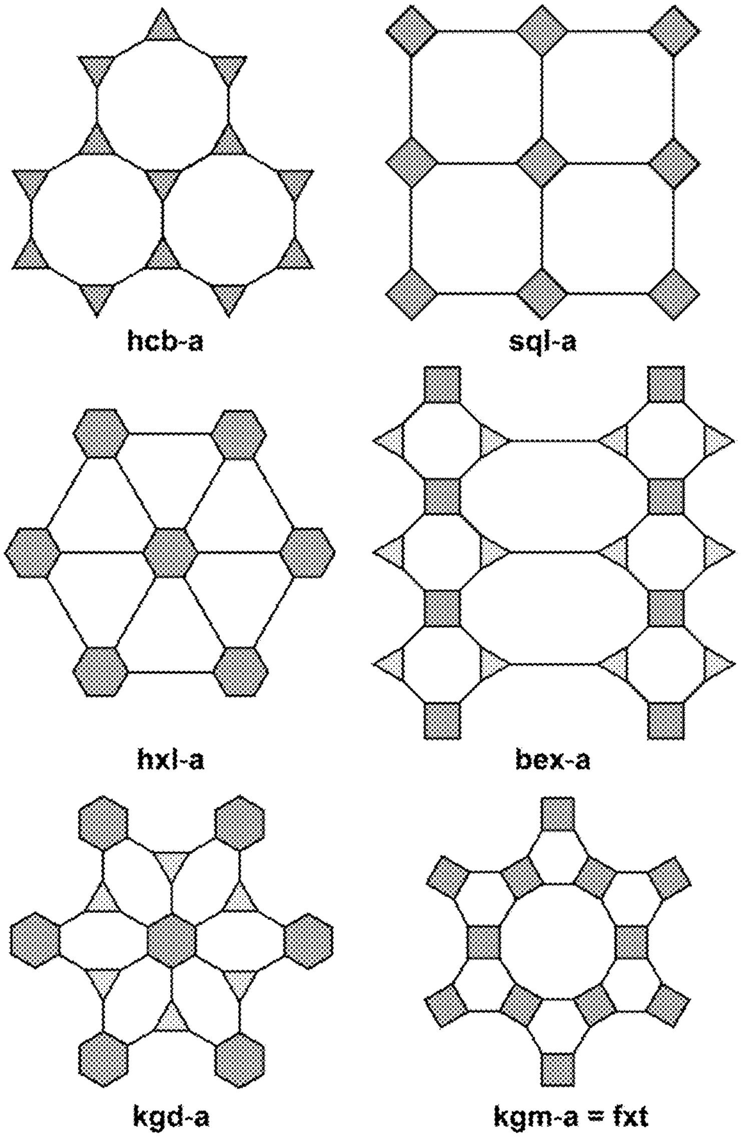
FIG. 6. 2-D topological structures of COFs.
Figure 7:
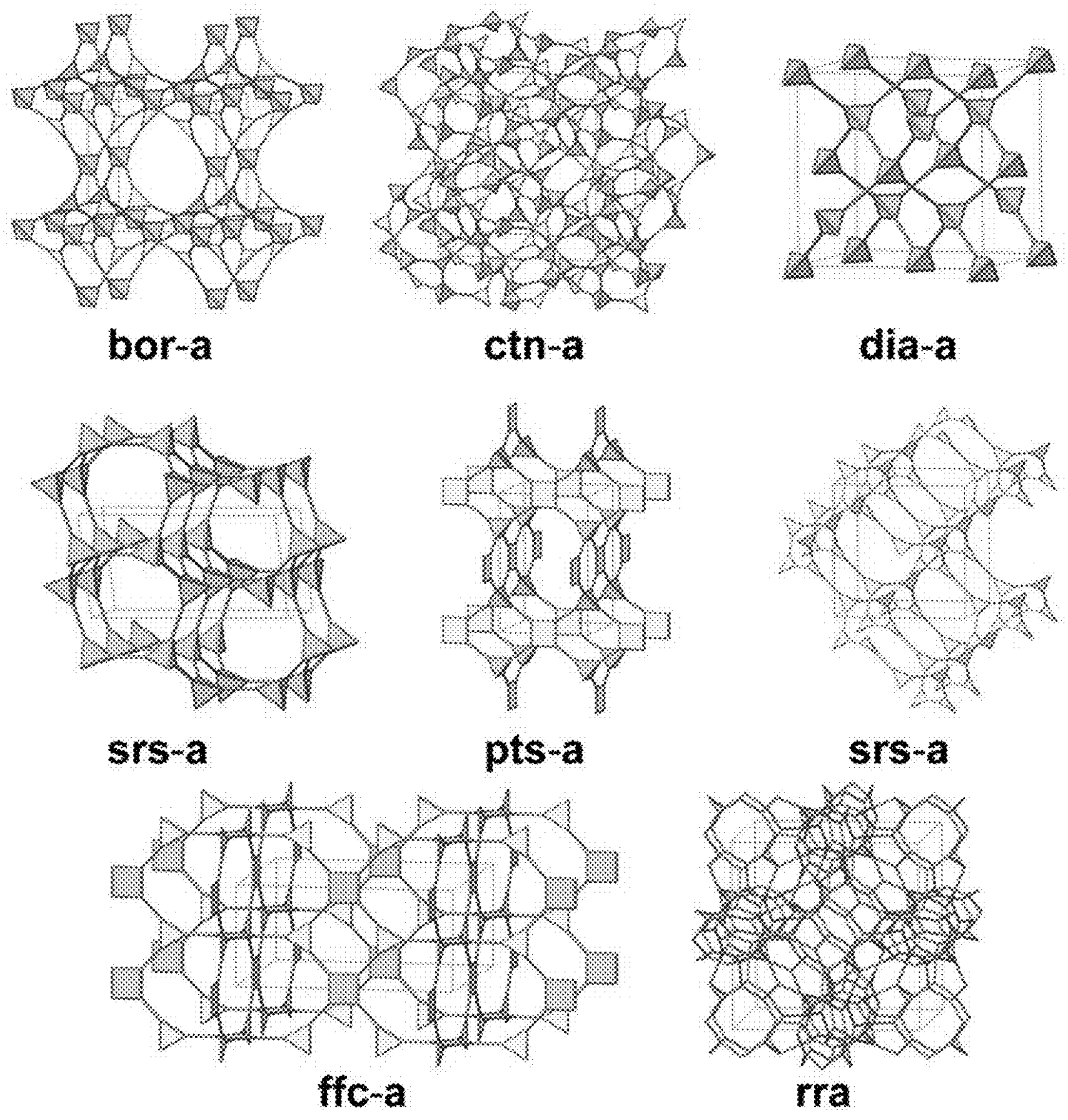
FIG. 7. 3-D topological structures of COFs.

In specific embodiments, the dynamic capture capacity is characterized by a breakthrough system Minimum requirement of such systems includes the simulation of working gas composition ($CO_2$, $H_2O$, $O_2$, etc.), gas flow, dynamic pressure and temperature in all steps of the dynamic capture with suitable accuracy and response time for the scale of application. The system should be equipped with gas analyzing system for tracing the gases involved in the process ($CO_2$, $H_2O$, $O_2$, etc.) with suitable accuracy and response time for the scale of application. An example is provided in the scheme of FIG. 6. In some variations where COFs are used as active adsorbents in membranes, membrane exchangers are used to replace the sorption bed in the breakthrough system, or instead tested in other continuous flow simulation system.

Utilization of COFs for Carbon Capture Process

Post-Combustion Capture (PCC)

In specific embodiments, COFs are used as solid adsorbent in the post-combustion capture of $CO_2$ from natural gas or coal flue gas. In most variations, the $CO_2$ concentration in the feed flue gas is between 4% and 16%, and the temperature of the feed flue gas is below 40 ° C.

In some variations, COFs are used in pure form, homogeneously mixed with other materials, or supported on other materials in the form factor of powders. In some variations, COFs are used in pure form, homogeneously mixed with other materials, or supported on other materials in the form factor of shape bodies. In these scenarios, the powder or shape bodies are used in sorption beds, fluidized beds, coated heat exchangers, or membranes, etc.

In these scenarios, removal of $CO_2$ from COFs involve heating, change of pressure, gas sweeping, washing, etc., or the combination of some or all of them.

In these scenarios, COFs exhibiting such properties are used:

High working capacity difference toward $CO_2$ from the combination of chemisorption (if present) and physisorption depending on the adsorption condition and regeneration condition.

For chemisorption, bearing reactive functional groups such as —$NH_2$, —NHR.

For physisorption, high surface area with polar functional groups such as —OH, —F.

For the dynamic capacity measurement of such COFs, breakthrough experiments are configured with feed gas mixture of 4%-16%, corresponding humidity and temperature.

Adequate affinity to $CO_2$ such that enough working capacity is retained in the presence of $H_2O$.

Robustness: chemical stability to $H_2O$, $O_2$, $CO_2$, and impurities in both adsorption condition and regeneration condition, including the retention of chemical composition, crystallinity, sorption capacities and porosity. Thermal stability toward the range of operation temperature.

Open framework structure with permanent porosity to ensure efficient mass transfer.

In some variations where heating is used for regeneration, low heat capacity.

In some variations where the COF is in shape body or supported by other materials, tight binding for mechanical stability.

In some variations, COFs are used in pure form, homogeneously mixed with other materials, or supported on other materials in the form factor of membranes. In these scenarios, the powder or shape bodies are used in membrane filtration, membrane exchanger, or cartridge exchanger, etc.

High, selective affinity toward $CO_2$ that increases the solubility of the membrane, through both chemisorption (if present) and physisorption at the separation condition.

For chemisorption, reactive functional groups such as —$NH_2$, —NHR, are part of the COF.

For physisorption, polar functional groups such as —OH, —F, are part of the COF.

For the dynamic capacity measurement of such COFs, breakthrough experiments or membrane-specific continuous tests are configured with feed gas mixture of 4%-16%, corresponding humidity and temperature.

Adequate affinity to $CO_2$ such that enough working capacity is retained in the presence of $H_2O$.

Robustness: chemical stability to $H_2O$, $O_2$, $CO_2$, and impurities in both adsorption condition and regeneration condition, including the retention of chemical composition, crystallinity, sorption capacities and porosity. Thermal stability toward the range of operation temperature.

In some variations where the COF is supported by other materials in the membrane, tight binding with the support for mechanical stability.

In some variations where heating is used for regeneration, low heat capacity.

Direct Air Capture (DAC)

In specific embodiments, COFs are used as solid adsorbent in the direct capture of $CO_2$ from ambient air. In most variations, the $CO_2$ concentration in the feed flue gas is atmospheric concentration (~400 ppm, 1 atm. In some variations, $CO_2$ concentration >400 ppm when compressed air is used) or slightly higher through compression or in a closed, non-ambient chamber, and the temperature of the feed gas is ambient temperature.

In some variations, COFs are used in pure form, homogeneously mixed with other materials, or supported on other materials in the form factor of powders. In some variations, COFs are used in pure form, homogeneously mixed with other materials, or supported on other materials in the form factor of shape bodies. In these scenarios, the powder or shape bodies are used in packed bed, cartridge exchanger, fluidized bed, etc.

In these scenarios, removal of $CO_2$ from COFs involve heating, change of pressure, gas sweeping, washing, etc., or the combination of some or all of them.

In these scenarios, COFs exhibiting such properties are used:

High working capacity difference toward $CO_2$ from chemisorption depending on the adsorption condition and regeneration condition.

For chemisorption, high gravimetric or volumetric density of reactive functional groups such as —$NH_2$, —NHR.

For physisorption, high surface area with polar functional groups such as —OH, —F, to enhance the affinity to $CO_2$.

For the dynamic capacity measurement of such COFs, breakthrough experiments are configured with feed gas mixture of ~400 ppm, corresponding humidity and temperature.

Adequate affinity to $CO_2$ such that enough working capacity is retained in the presence of $H_2O$.

Robustness: chemical stability to $H_2O$, $O_2$, $CO_2$, and impurities in both adsorption condition and regeneration condition, including the retention of chemical composition, crystallinity, sorption capacities and porosity. Thermal stability toward the range of operation temperature.

Open framework structure with permanent porosity to ensure efficient mass transfer.

In some variations where heating is used for regeneration, low heat capacity.

In some variations where the COF is in shape body or supported by other materials, tight binding for mechanical stability.

Parallel Water Harvesting

In some variations, the COF adsorbent exhibit high uptake of both $CO_2$ and $H_2O$ at the same time of PCC or DAC. The $CO_2$ and $H_2O$ can be therefore removed in the same step, or in different steps through different conditions. Through facile further purification, such COF adsorbent can produce high-purity water as a side-product of $CO_2$ capture from air or from flue gas. In these scenarios, COFs exhibiting such properties are used:

High working capacity difference toward $H_2O$ from physisorption depending on the adsorption condition and regeneration condition.

For the dynamic capacity measurement of such COFs, breakthrough experiments are configured with feed gas mixture at the desired humidity and temperature.

Adequate affinity to $H_2O$ such that enough working capacity is retained in the presence of $CO_2$.

Robustness: chemical stability to $H_2O$, $O_2$, $CO_2$, and impurities in both adsorption condition and regeneration condition, including the retention of chemical composition, crystallinity, sorption capacities and porosity. Thermal stability toward the range of operation temperature.

Open framework structure with permanent porosity to ensure efficient mass transfer.

In some variations where heating is used for regeneration, low heat capacity.

In some variations where the COF is in shape body or supported by other materials, tight binding for mechanical stability.

EXAMPLES

COF-366-F—Co

Figure 8:
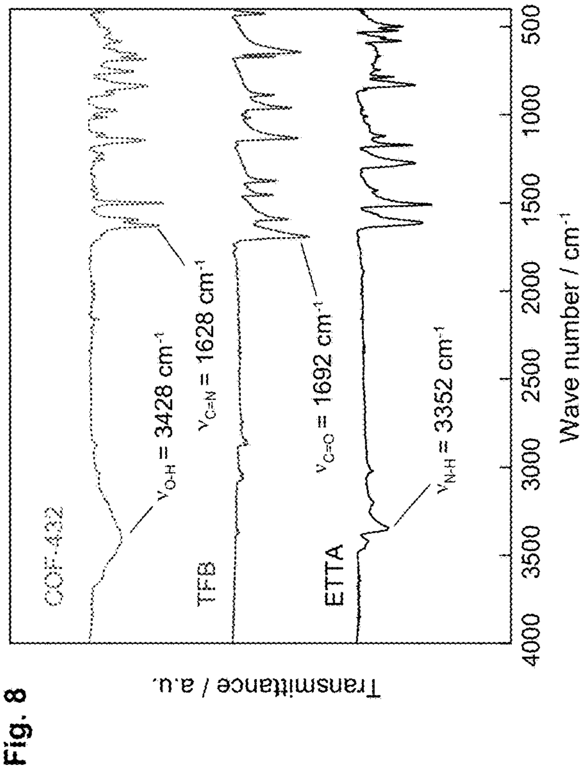
FIG. 8. FTIR spectrum of COF-432, TFB, and ETTA, colored in red, blue, and black, respectively.

COF-366-F—Co is an example of COF materials for explaining the definition of COFs in this disclosure and showcasing $CO_2$ capturing capacity exhibited in COF materials. The COF comprises of tetratopic building unit 5,10,15,20-tetraphenylporphinato]cobalt(II) and ditopic building unit 1,2,4,5-tetrafluorobenzene, linked by imine (—CH═N—) linkages. COF-366-F-Co is an extended structure with 2-dimensional sql topology. The crystallinity is established through PXRD and GIWAXS of COF-366-F—Co and thin film COF-366-F—Co on HOPG (FIG. 8).

Figure 9:
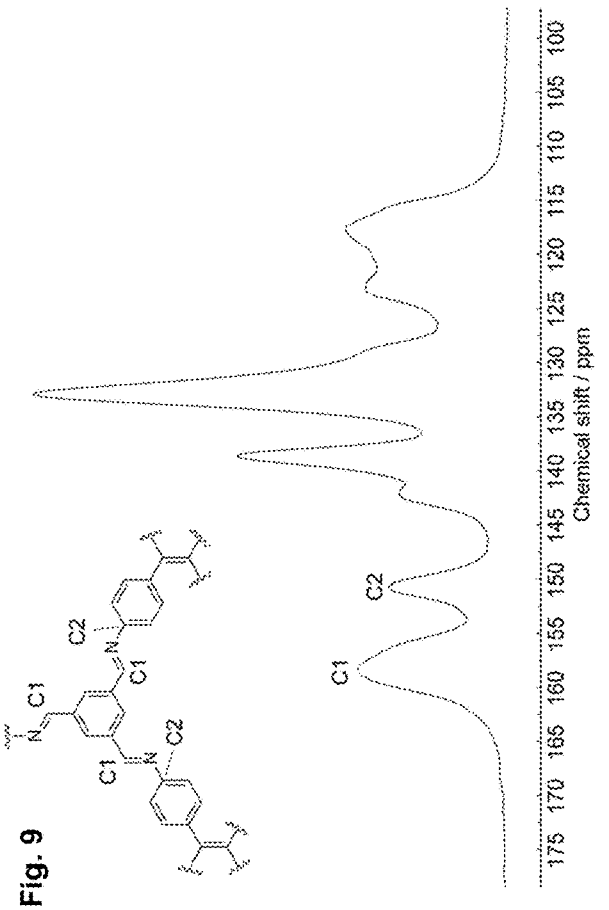
FIG. 9. Solid-state $^{13}C$ CP-MAS NMR spectrum of COF-432. The assignments of $^{13}C$ chemical shifts (in ppm) are indicated next to the respective atoms in the chemical structure.

The permanent porosity of COF-366-F—Co is established through $N_2$ isotherm experiment at 77 K, from which the BET surface area was obtained as 1901 $m^2/g$. $CO_2$ adsorption isotherm was measured at 273 K, 283 K, 298 K (FIG. 9), from which the $Q_{st}$ was derived to be 24.2 kJ/mol. Physisorption behavior is observed in the material for $CO_2$ sorption at 298 K. The sorption capacity is ~5 $cm^3/g$ at 15% $CO_2$ at 298 K, and is negligible at ~400 ppm at 298 K. The material is not suitable for DAC unless through other methods (electrochemical reaction), and has mild performance in PCC.

COF-316, COF-316-$CONH_2$ and COF-316-C(NOH)$NH_2$

Figure 10A:
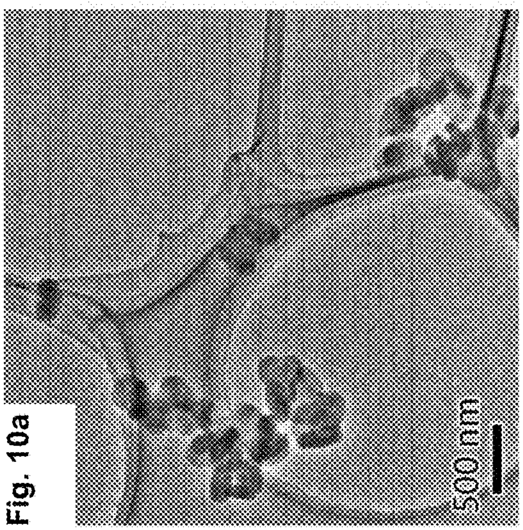
FIGS. 10*a*-10*b*. SEM image demonstrates phase-purity and uniform morphology (a) of COF-432. The crystal size of COF-432 is ca. 300 nm (b).
Figure 10B:
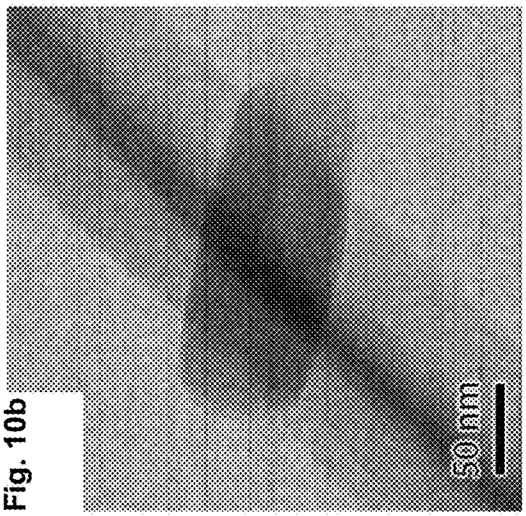

COF-316, COF-316-$CONH_2$, and COF-316-C(NOH)$NH_2$ are a series of examples that showcase the post-synthetic modification as approaches to access COFs with different functionalities, as well as showcasing the test of stability and $CO_2$ capturing capacity compared to other gases. COF-316 (also known as JUC-505) comprises of tritopic building unit triphenylene (6 bidentate extension) and ditopic building unit 1,4-dicyanobenzene (4 bidentate connections) linked by dioxin linkage. COF-316-$CONH_2$ and COF-316-C(NOH)$NH_2$ are synthesized by treating COF-316 with NaOH or $NH_2OH$, respectively. The crystallinity and chemical identity of these COFs are established through PXRD and solid-state NMR (FIG. 10).

Figure 11:
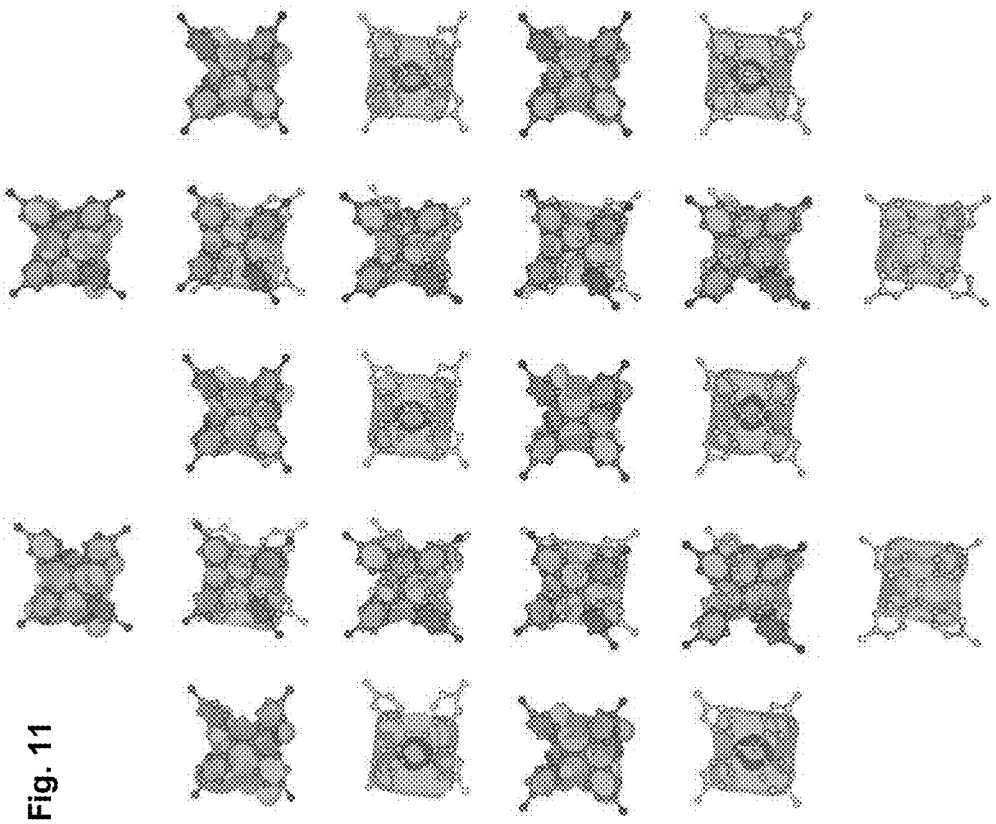
FIG. 11. COF-432 electron density map showing regions of high electron density which can be assigned to the ETTA fragments.

Chemical stability of COF-316 in inorganic acid and base conditions are examined by exposing COF-316 in aqueous solutions of 6 M HCl and 6 M NaOH. By comparison of PXRD, FT-IR and $N_2$ isotherm at 77 K before and after the treatment (FIG. 11). The results confirm that the crystallinity and porosity is largely retained for COF-316 in exposure to aqueous solutions of 6 M HCl and 6 M NaOH. FT-IR of the product after 6 M NaOH treatment shows the chemical instability of COF-316 which indicates the change of chemical identity, which is the same as in the synthesis of COF-316-$CONH_2$.

Figure 12:
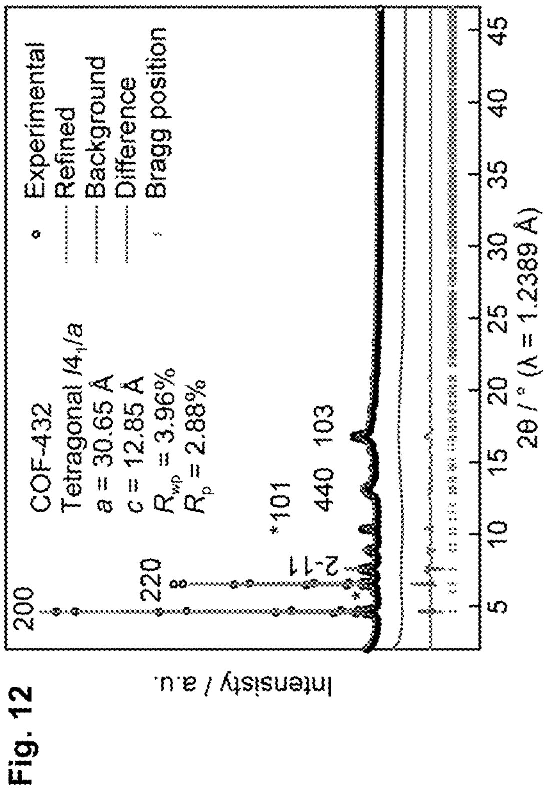
FIG. 12. Le Bail refinement of COF-432 against the experimental WAXS pattern displaying the experimental pattern (black) and the refined fit (red). The background (blue), difference plot (green), and Bragg positions (pink) are also provided.
Figure 13:
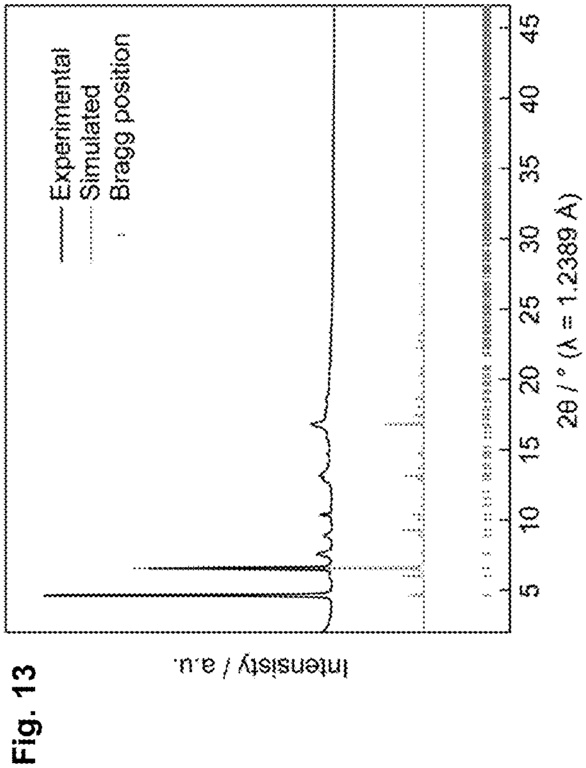
FIG. 13. WAXS patterns comparison of the simulated (orange) pattern with the experimental (black) pattern of COF-432. Bragg positions (pink) are also provided.

$CO_2$, $CH_4$ and $N_2$ isotherms are measured for COF-316 (JUC-505) at 273 K between 0 to 1 bar (FIG. 12). COF-316 (JUC-505) exhibits physisorptive behavior toward $CO_2$ at 273 K, and the uptake is significantly higher than at the same (and complementary) partial pressure of $CH_4$ and $N_2$ when $CO_2$ concentration is higher than 0.05 bar. This measurement indicates that COF-316 (JUC-505) exhibits possible separation performance of $CO_2$ from dry binary mixture of $CO_2/N_2$ and $CO_2/CH_4$ at 273 K. It is not indicative of PCC or DAC performances at ≥298 K and humid conditions.

COF-701

Figure 14:
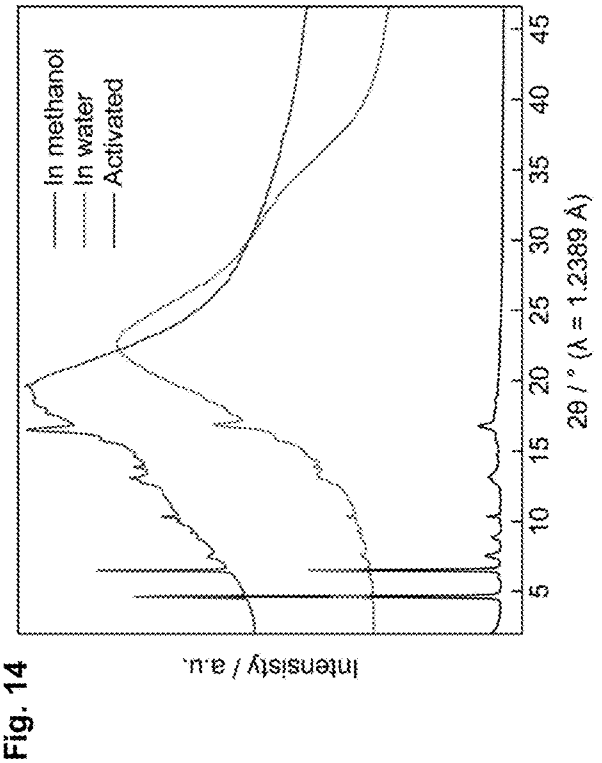
FIG. 14. Comparison of WASX patterns of activated COF-432, and COF-432 samples with methanol and water in its pores.
Figure 16:
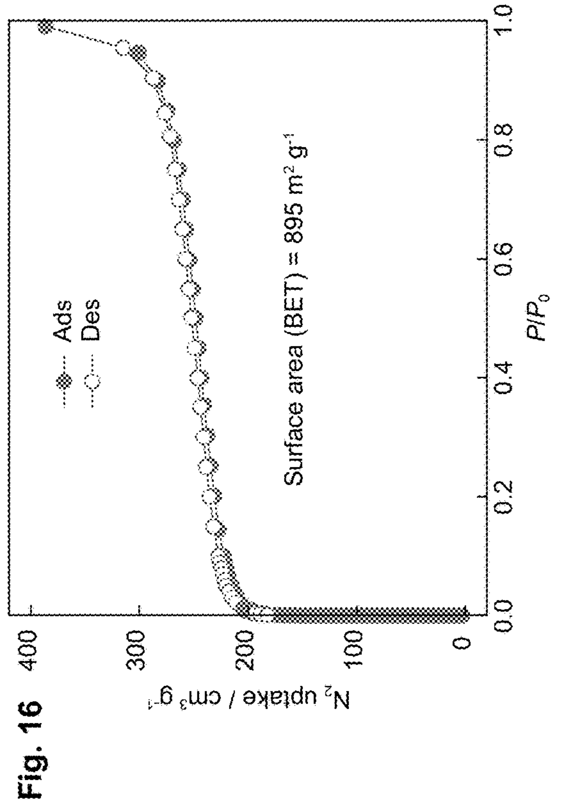
FIG. 16. $N_2$ sorption isotherm of activated COF-432 at 77 K. The filled and open circles represent the adsorption and desorption branch, respectively. The connecting line in the $N_2$ isotherm is provided as a guide for the eye.
Figure 20:
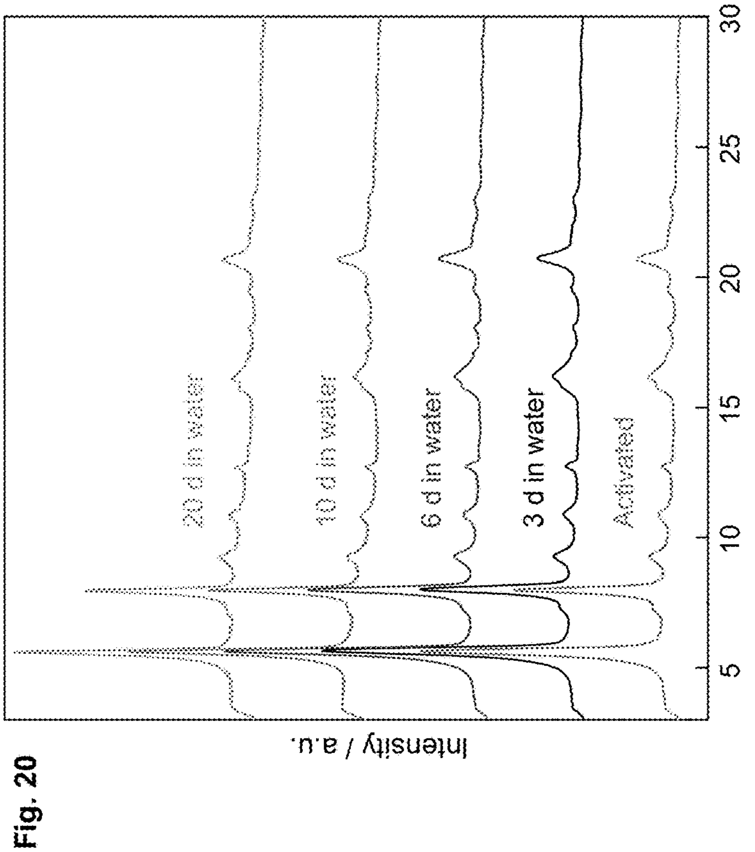
FIG. 20. PXRD analyses of COF-432 after immersing it in water for different amounts of time (3, 6, 10 and 20 days).
Figure 17:
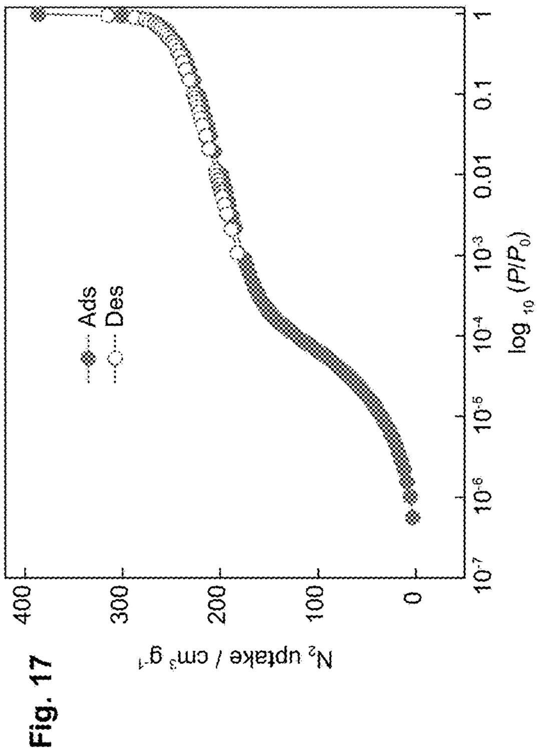
FIG. 17. $N_2$ sorption isotherm of activated COF-432 at 77 K. The filled and open circles represent the adsorption and desorption branch, respectively. The connecting line in the $N_2$ isotherm is provided as a guide for the eye.
Figure 18:
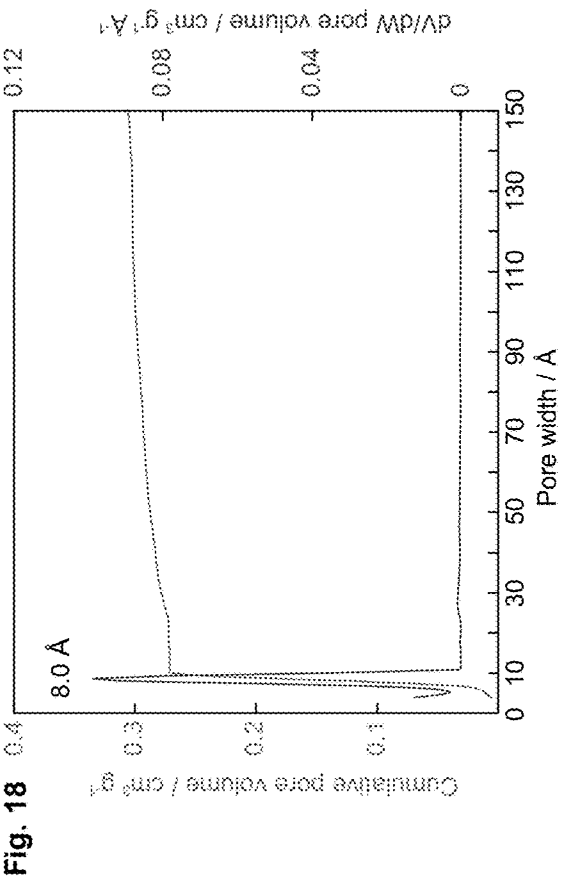
FIG. 18. Pore size determination for COF-432 based on the $N_2$-DFT fit indicates a pore width of 8.0 Å.
Figure 19:
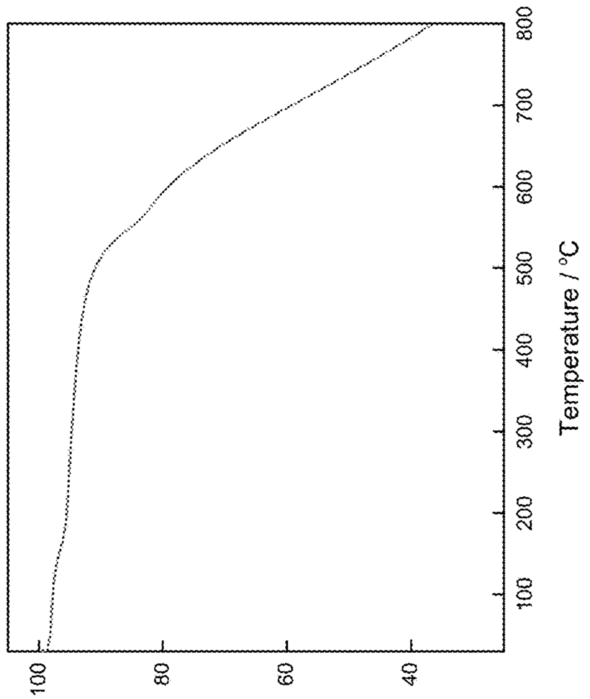
FIG. 19. Thermogravimetric analysis of COF-432 under nitrogen flow.
Figure 21:
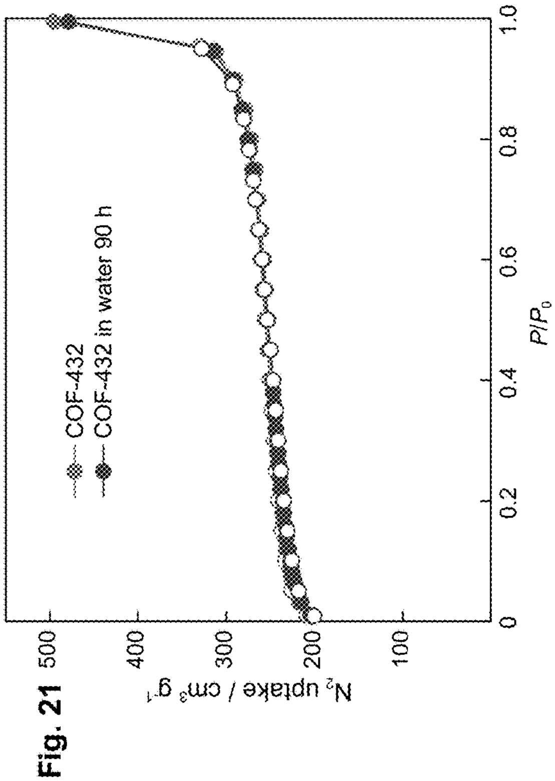
FIG. 21. $N_2$ sorption analysis at 77 K of activated COF-432 before and after immersion in water for 90 hours. The filled and open circles represent the adsorption and desorption branch, respectively. The connecting line is provided as a guide for the eye.
Figure 22:
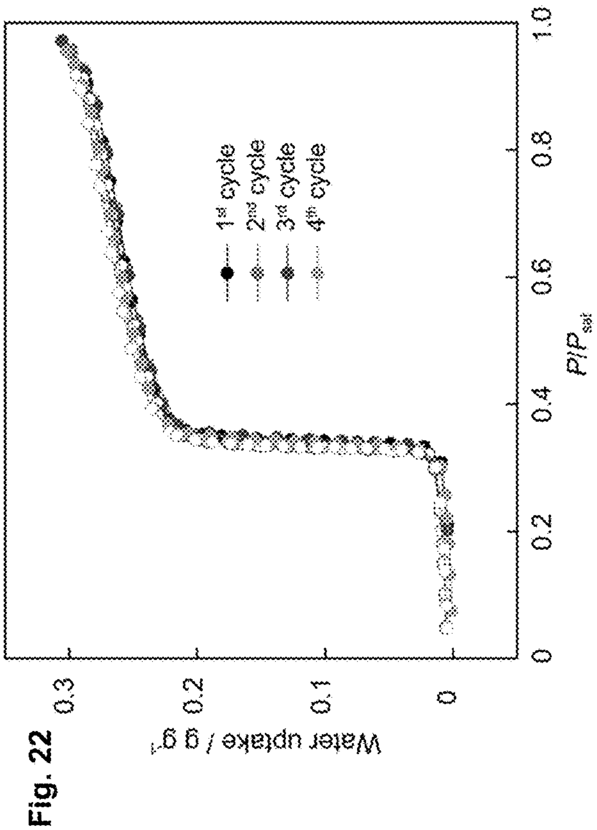
FIG. 22. Four consecutive water sorption measurements on COF-432 at 298 K. P: Partial water vapor pressure. $P_{sat}$: Saturation vapor pressure of water at 298 K.
Figure 23:
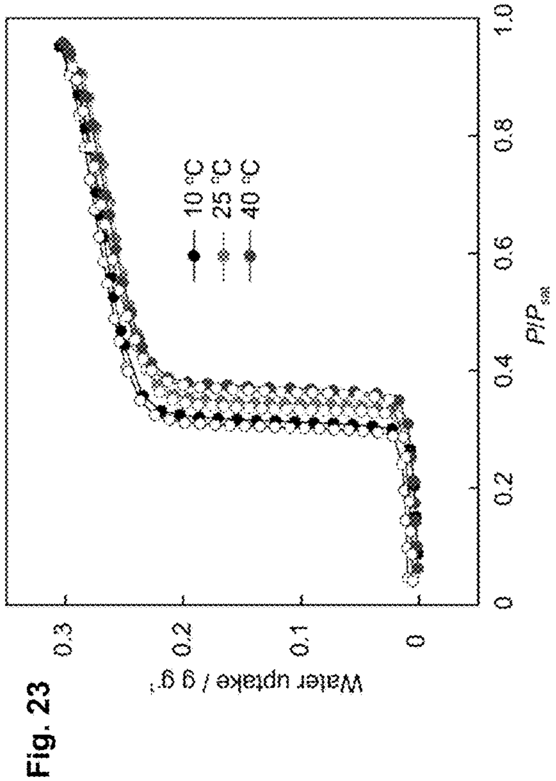
FIG. 23. Water sorption analysis on COF-432 at different temperatures (10, 25, 40° C.). P: Partial water vapor pressure. $P_{sat}$: Saturation vapor pressure of water at the respective temperature.
Figure 25:
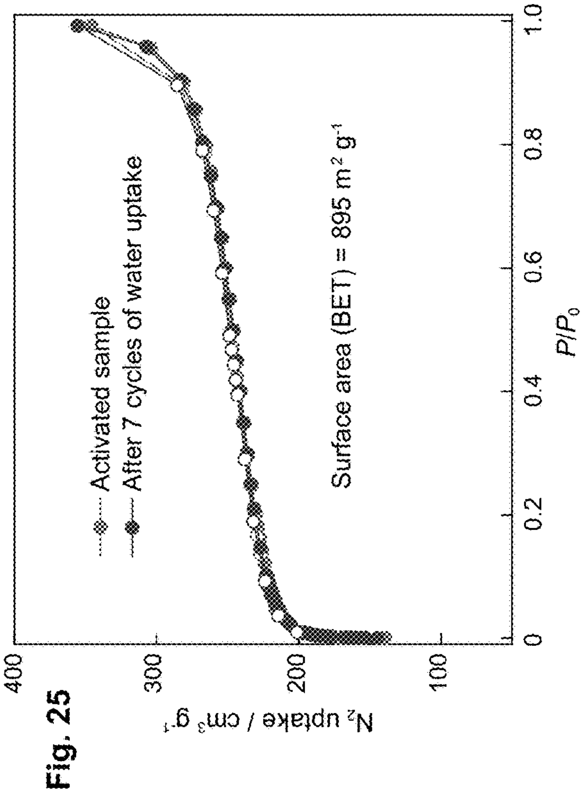
FIG. 25. $N_2$ sorption analysis at 77 K of activated COF-432 before and after 7 consecutive water sorption measurements. The filled and open circles represent the adsorption and desorption branch, respectively. The connecting line is provided as a guide for the eye.
Figure 24:
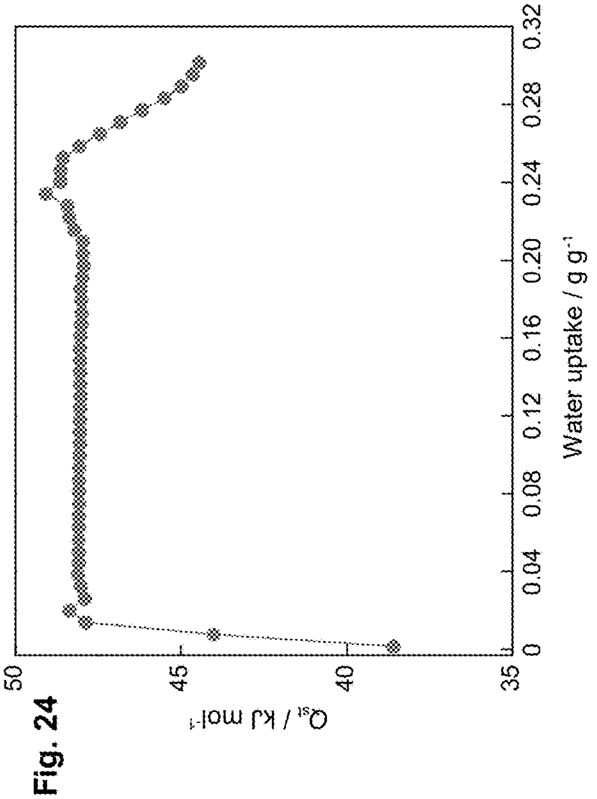
FIG. 24. Isosteric heat of adsorption of COF-432, as determined by the Clausius-Clapeyron relation applied to the water sorption isotherms measured at different temperatures (10, 25, 40° C.).
Figure 26:
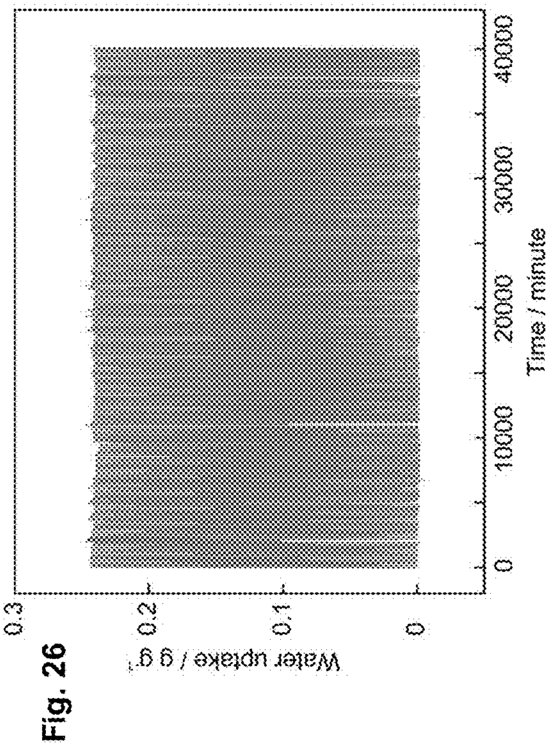
FIG. 26. Water cycling stability test for 300 adsorption-desorption cycles conducted on COF-432 at constant water vapor pressure (1.7 kPa). Adsorption and desorption are carried out at 30° C. (40% relative humidity, RH) and 35° C. (30% RH), respectively. P: water vapor pressure. $P_{sat}$: saturation water vapor pressure at the given temperature.
Figure 27:
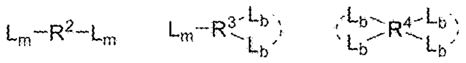
FIG. 27. Schematic representation of organic building blocks.
Figure 27:
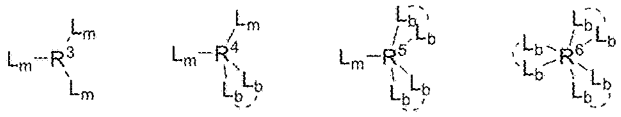
Figure 27:
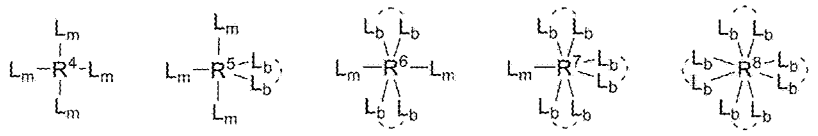
Figure 27:
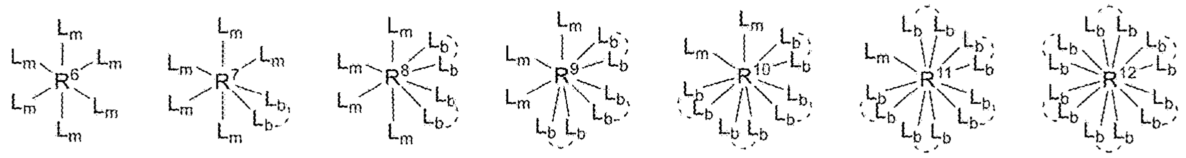
Figure 27:
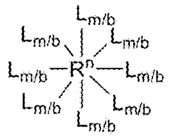
Figure 27:
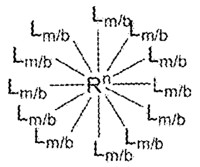
Figure 28A:
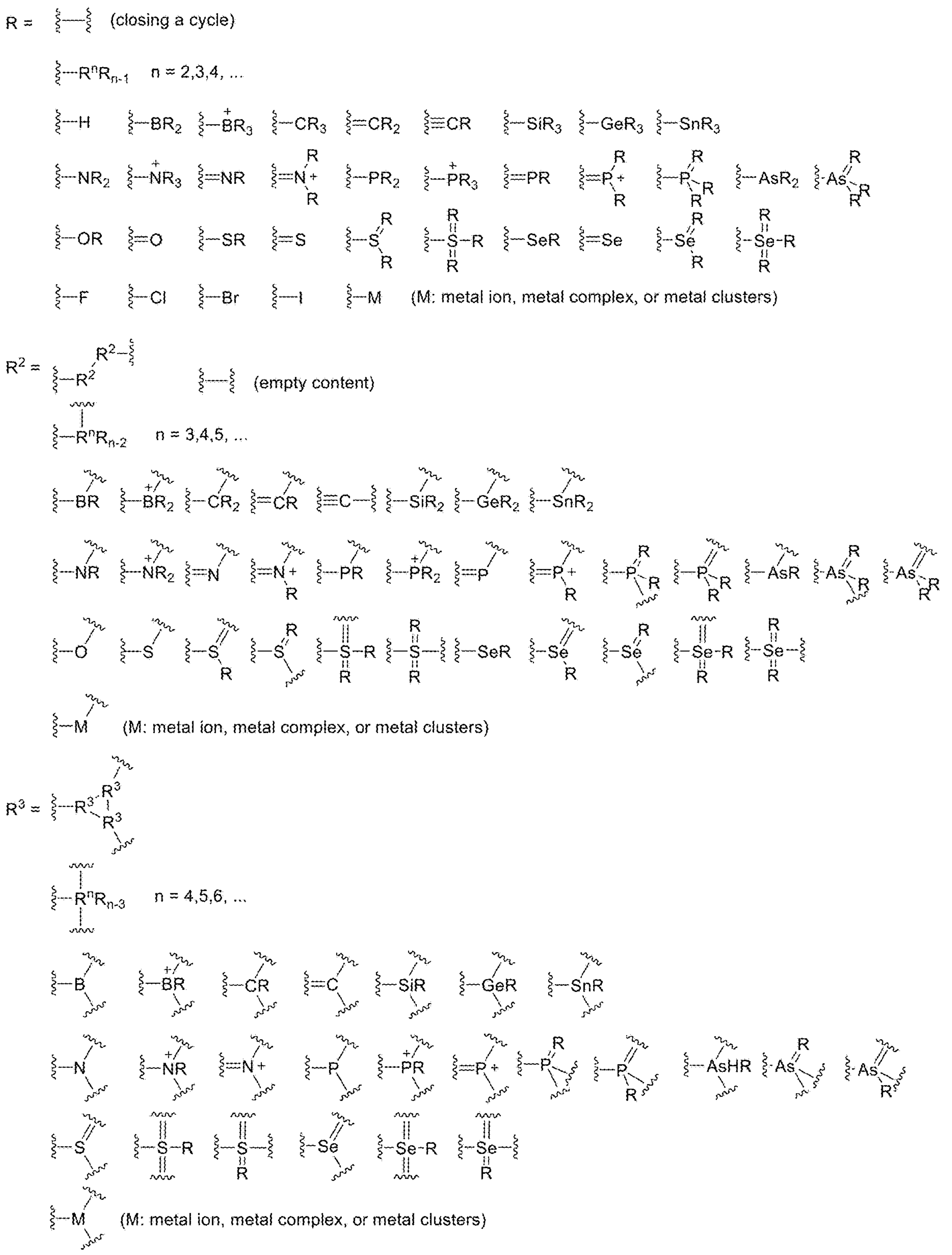
FIGS. 28*a*-28*b*. Schematic representation of organic fragments comprising organic building units in the range of definition in this disclosure.
Figure 28B:
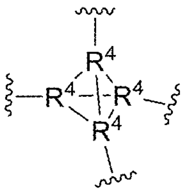
Figure 28B:
Figure 28B:
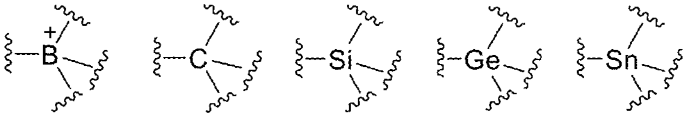
Figure 28B:
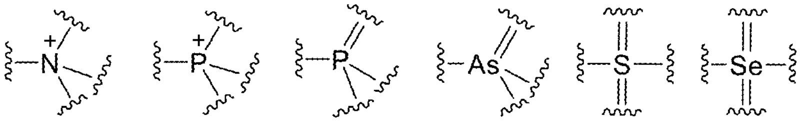
Figure 28B:
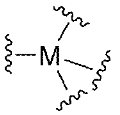
Figure 28B:
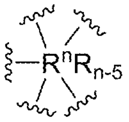
Figure 28B:
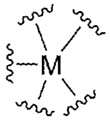
Figure 28B:
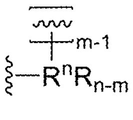
Figure 28B:
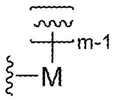
Figure 29:
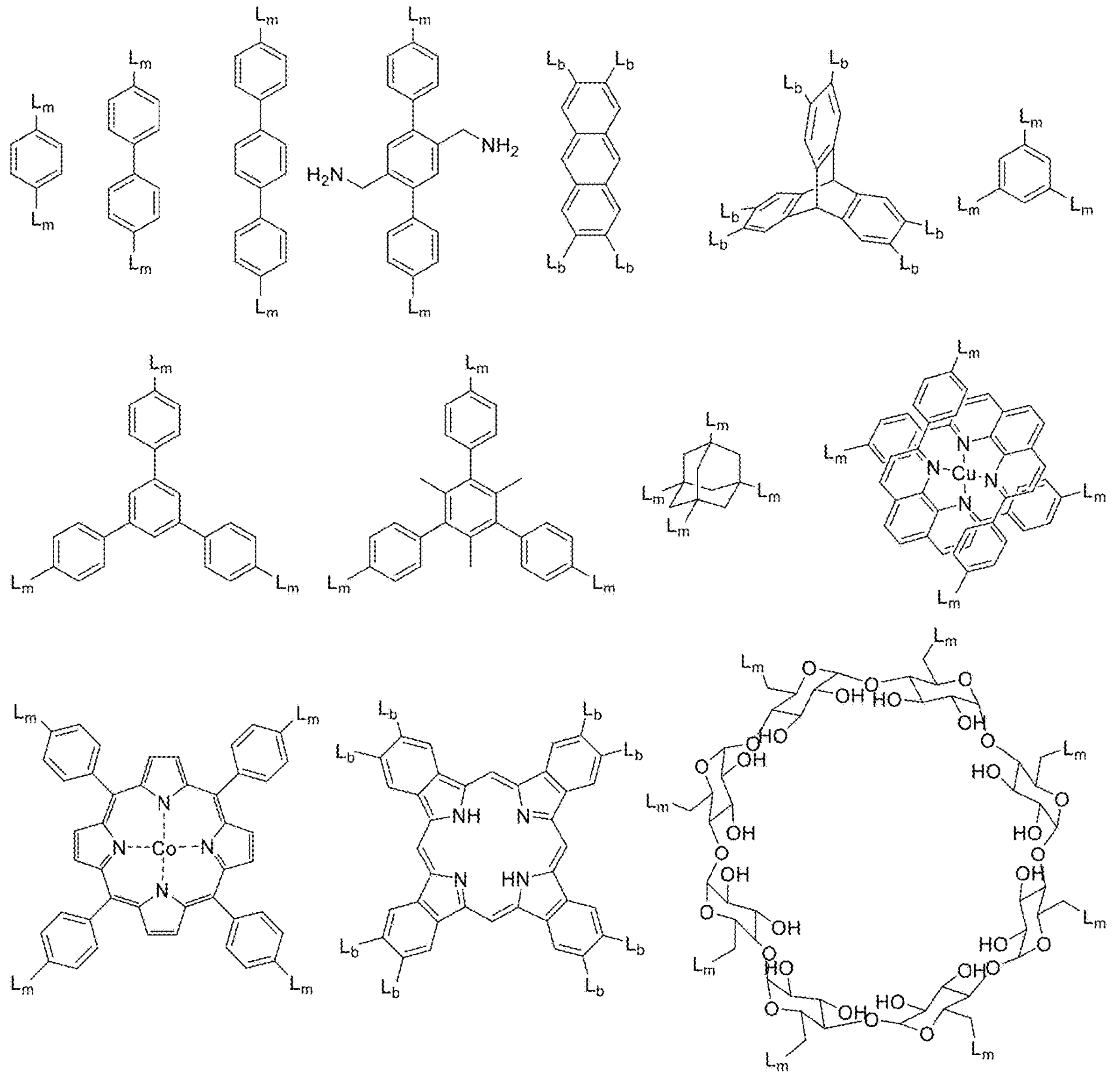
FIG. 29. Example structures of organic building units.
Figure 30:
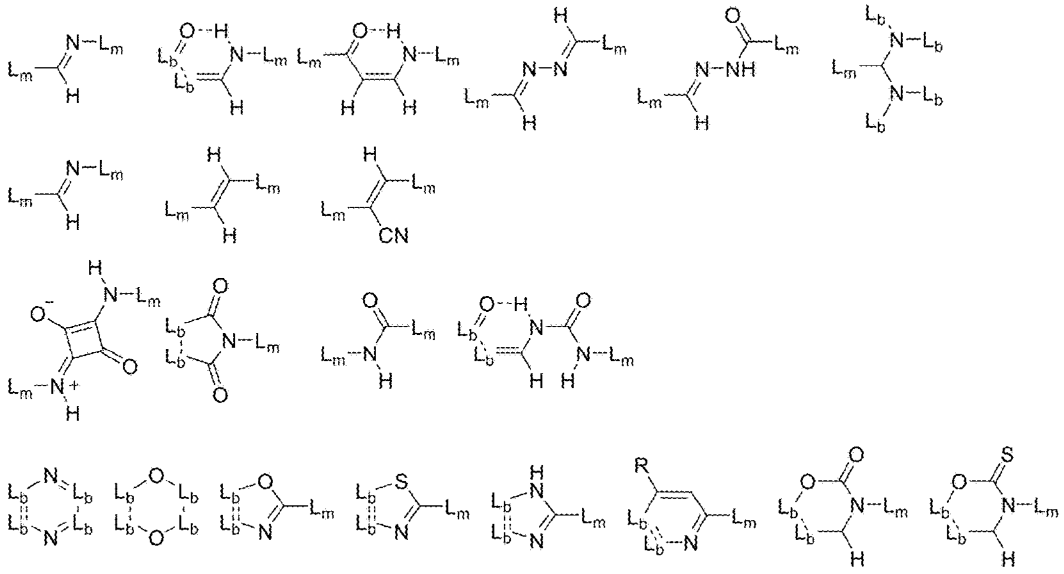
FIG. 30. Schematic representation of linkages in the range of definition of COFs in this disclosure.
Figure 30:
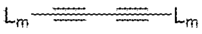
Figure 30:
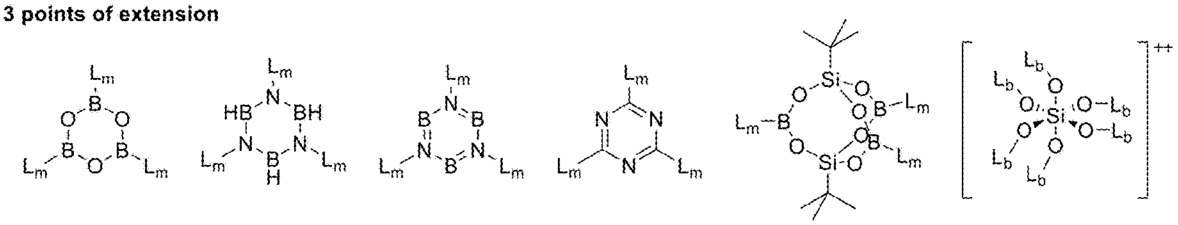
Figure 31:
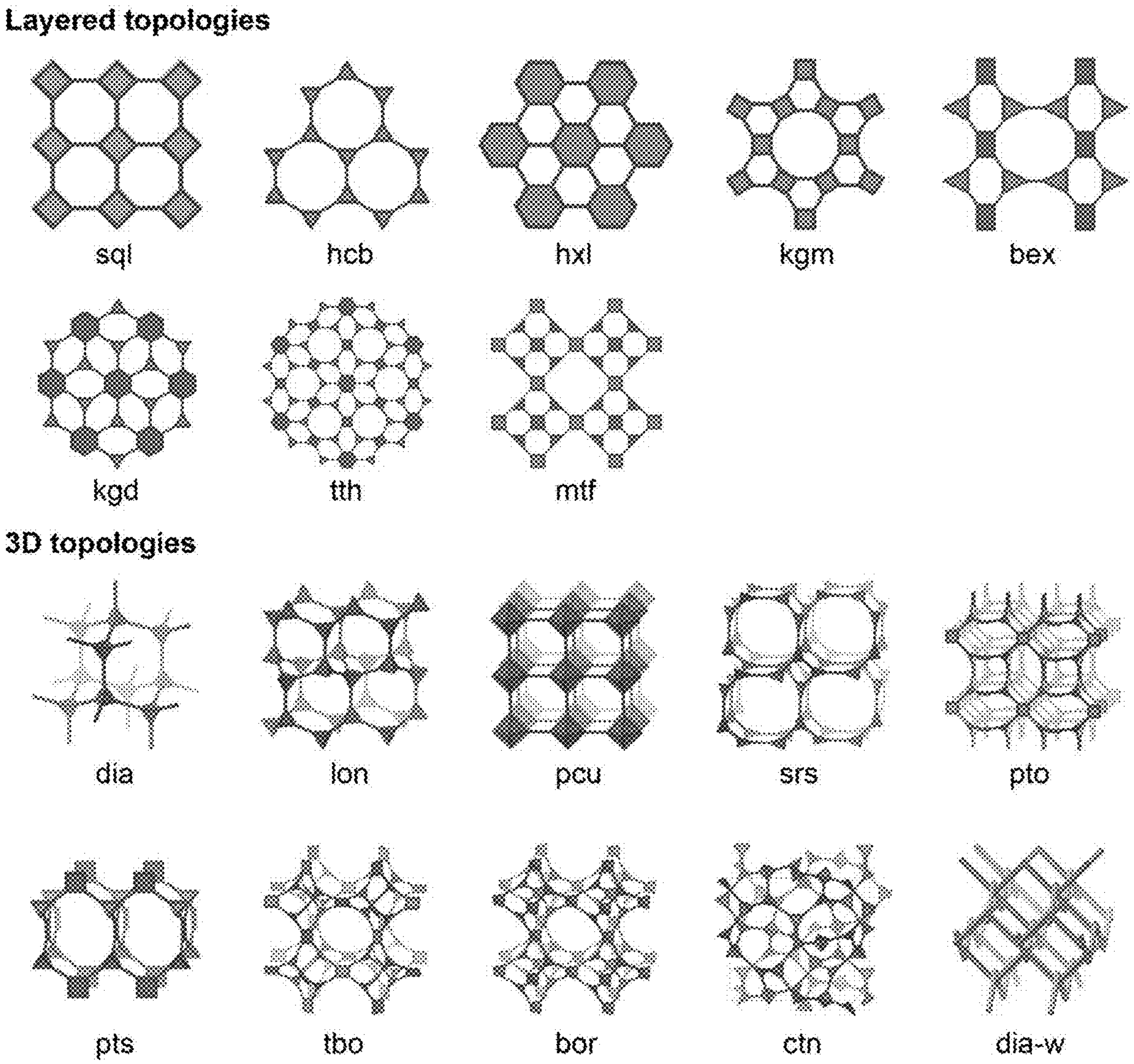
FIG. 31. Schematic representation of examples of COF topologies.
Figure 32:
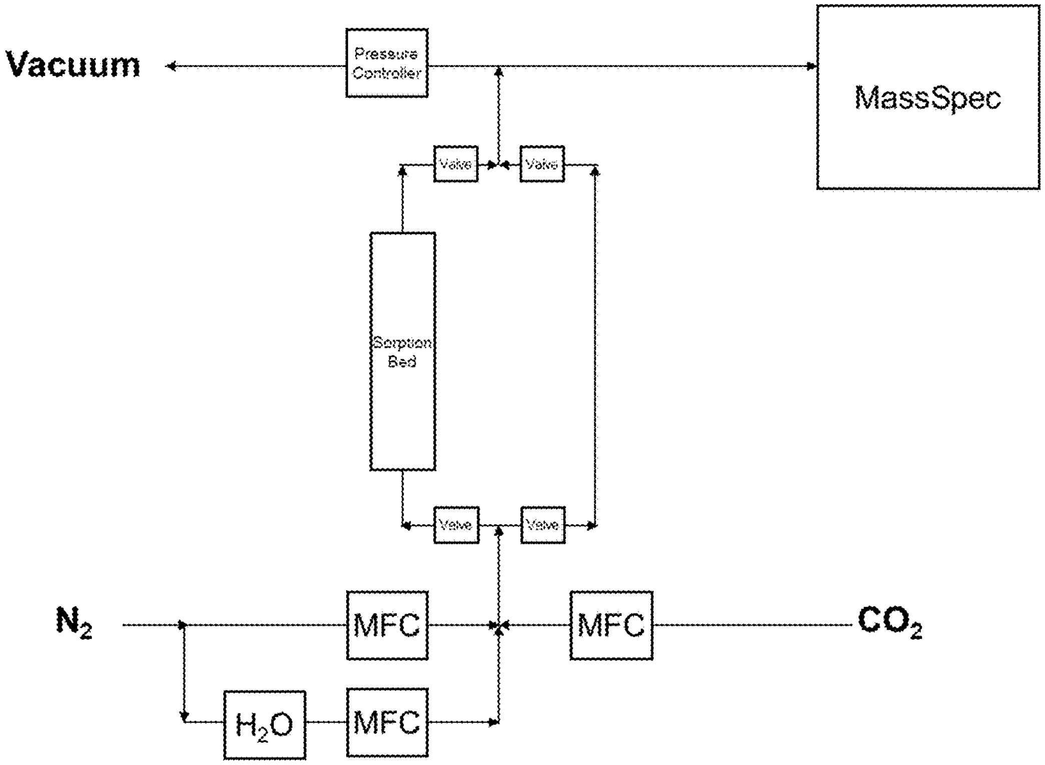
FIG. 32. Schematic representation of an example breakthrough system required for the embodiment of this disclosure.
Figure 33:
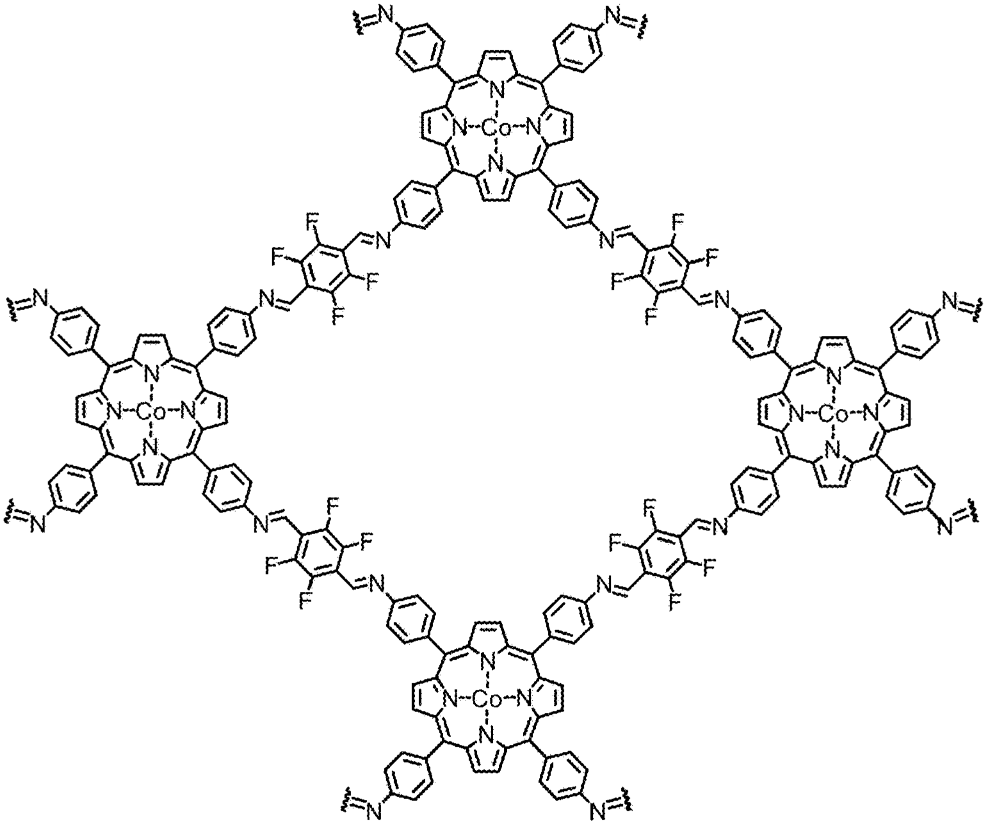
FIG. 33. Schematic representation of COF-366-Co—F.
Figure 34:
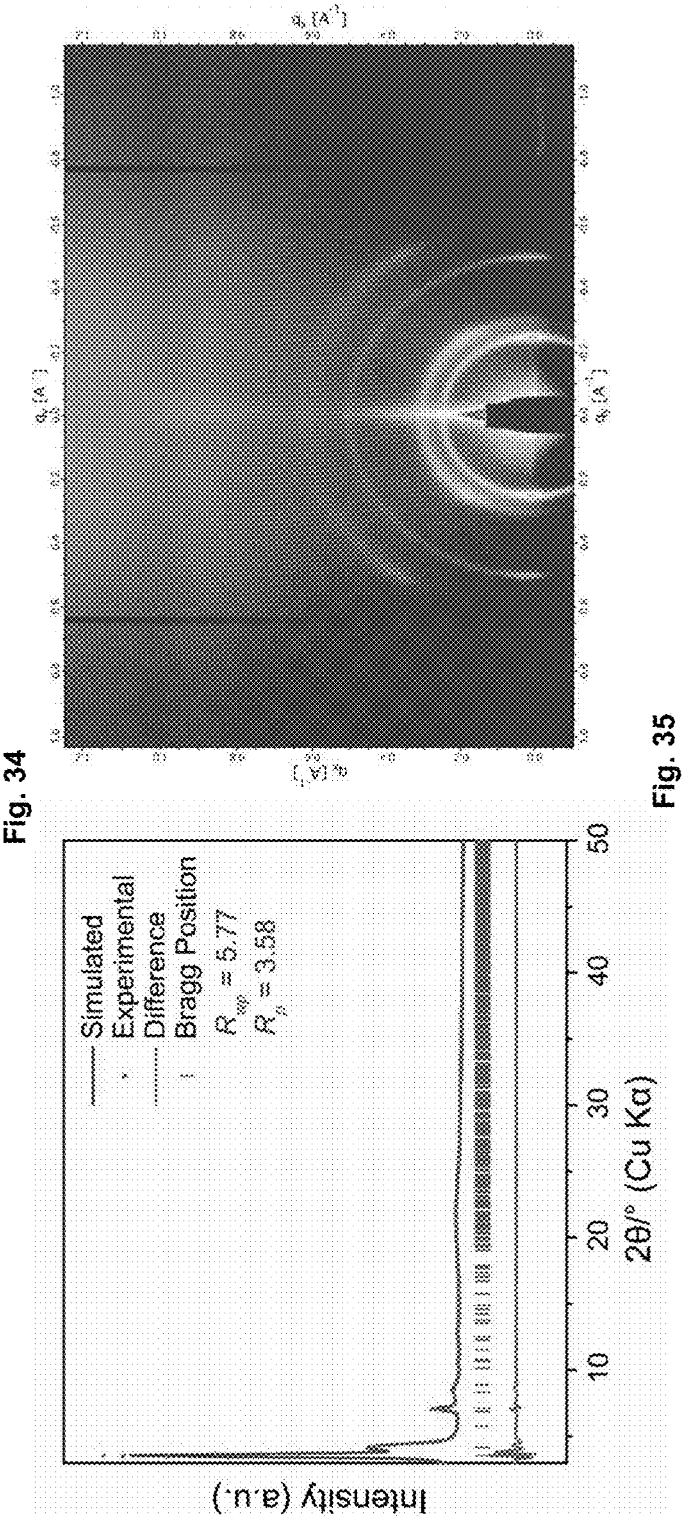
FIG. 34. Pawley fit of PXRD of a powder sample of COF-366-F—Co and GIWAXS results of a thin film COF-366-F—Co on HOPG.
Figure 35:
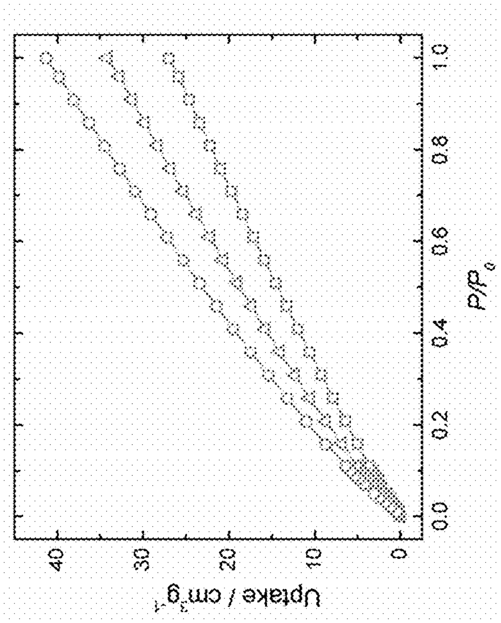
FIG. 35. $CO_2$ adsorption isotherm for COF-366-F-Co at 273 (circle), 283 (triangle), and 298 K (square).
Figures 36A, 36B, 36C, 36D, 36E:
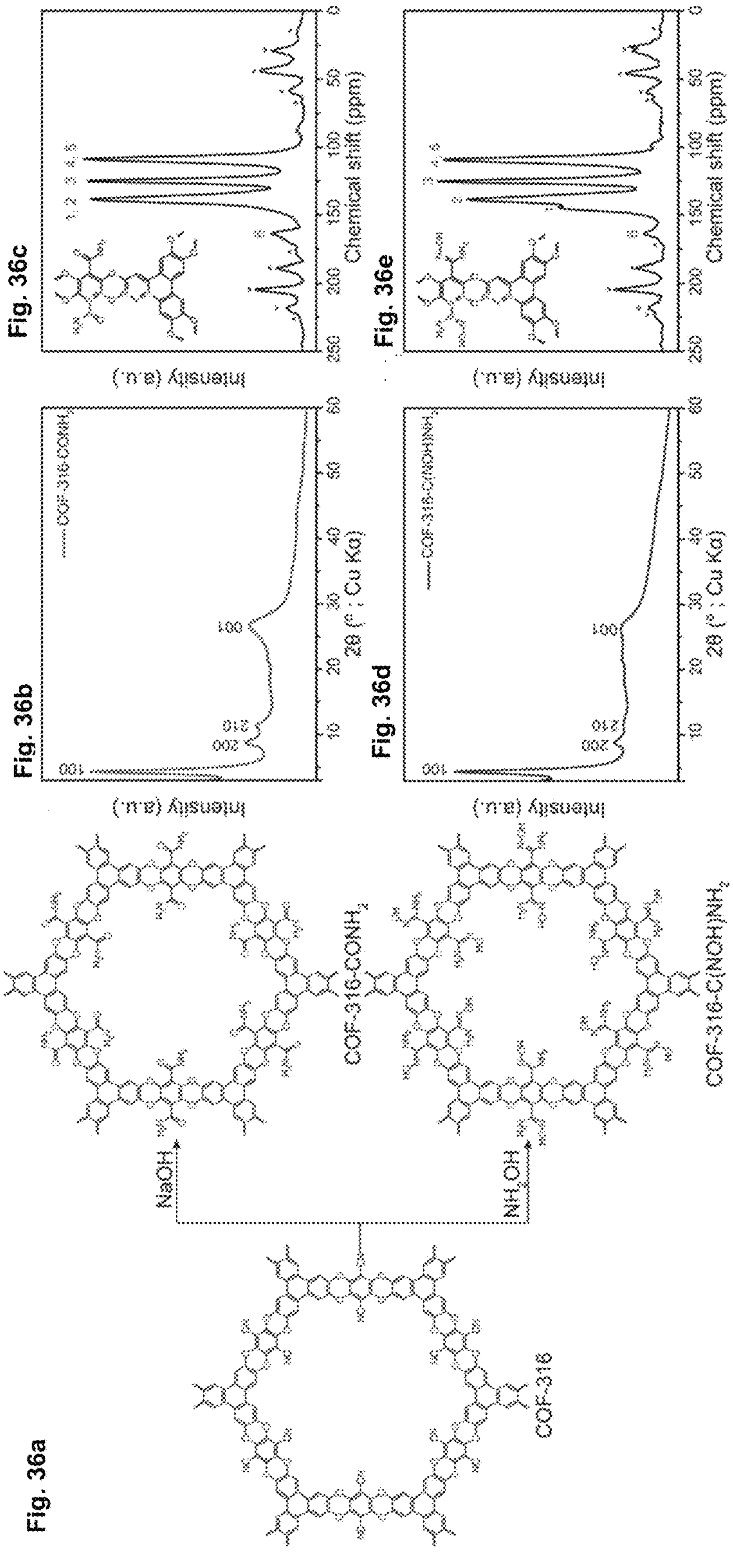
FIGS. 36*a*-36*e*. (a) Post-synthetic modification of COF-316. (b, d) PXRD patterns of COF-316—$CONH_2$ and —$C(NOH)NH_2$, indicating the retention of crystallinity and long-term stability in base. (c, e) Solid state $^{13}C$ CP-MAS NMR spectra of COF-316—$CONH_2$ and —$C(NOH)NH_2$, respectively. Asterisks denote the spinning sidebands.
Figure 40D:
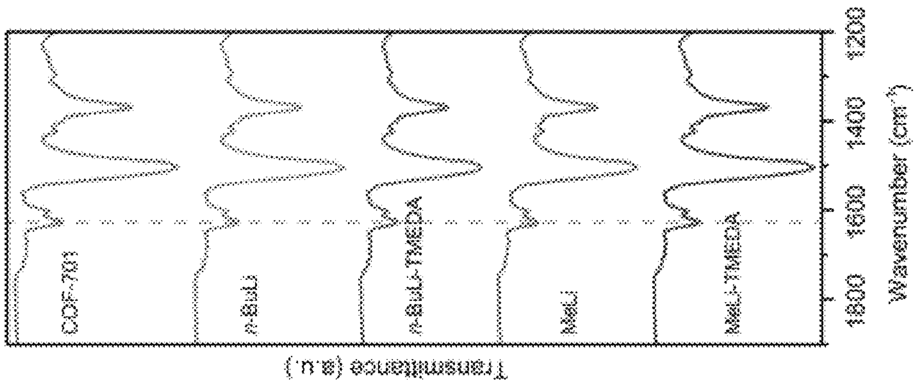
FIG. 40*a*-40*f*. Chemical stability test of COF-701 with Brønsted acid and base (a, b), organolithium reagents (c, d), and Lewis acid (e, f). WAXS patterns of treated materials with zoomed insets (a, c, e) and FT-IR spectra (b, d, 1900-1200 $cm^{-1}$; f, 1900-900 $cm^{-1}$) illustrate the retention of crystallinity and chemical composition of COF-701.
Figure 40C:
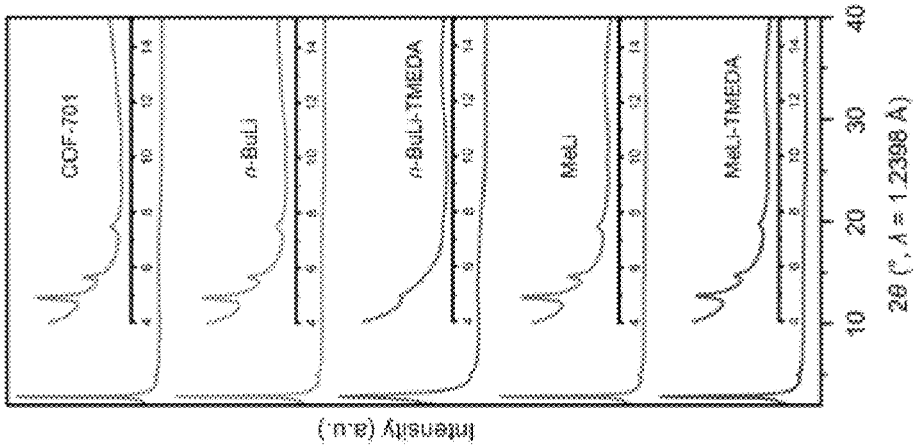
Figure 40B:
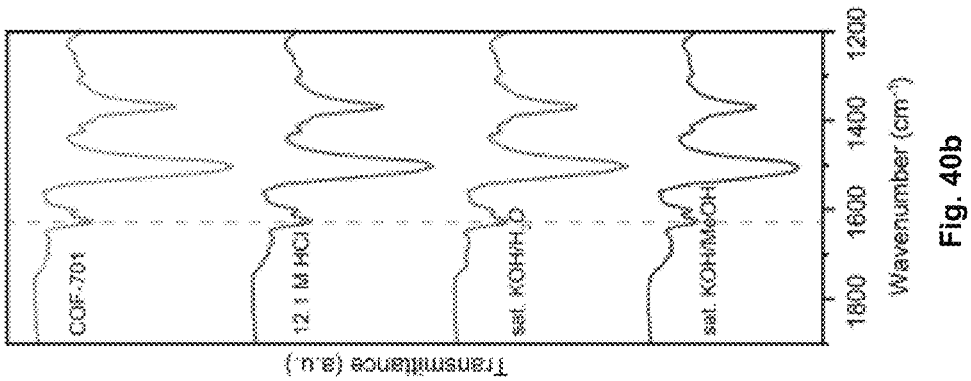
Figure 40A:
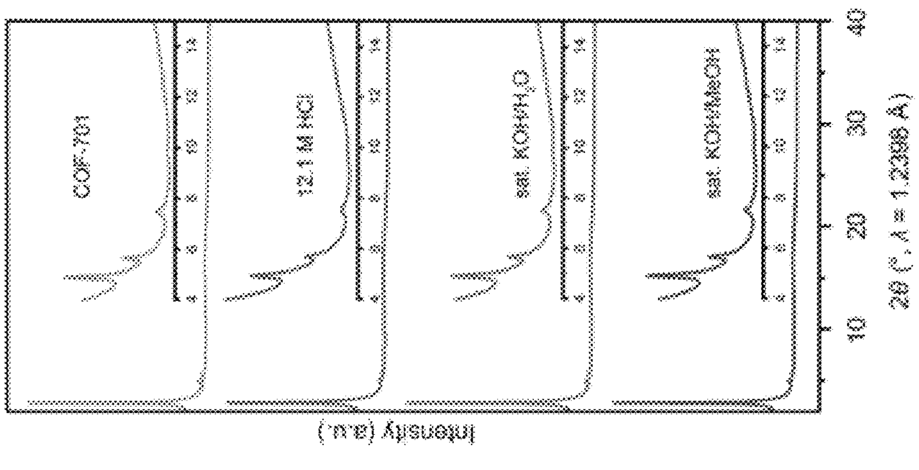
Figure 40E:
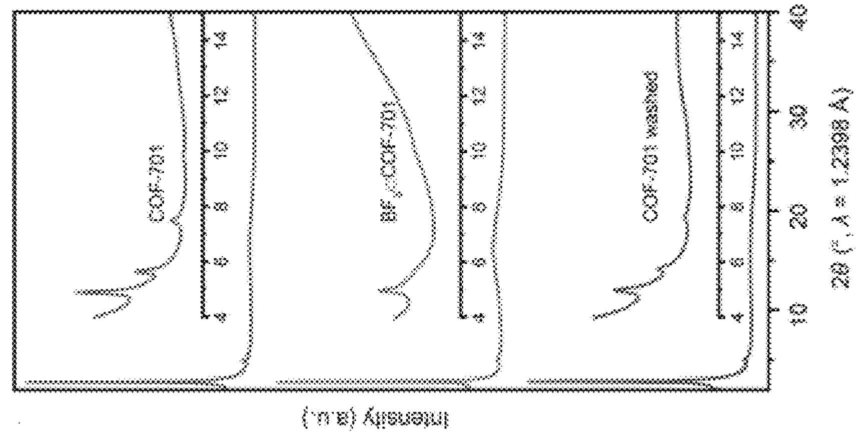
Figure 40F:
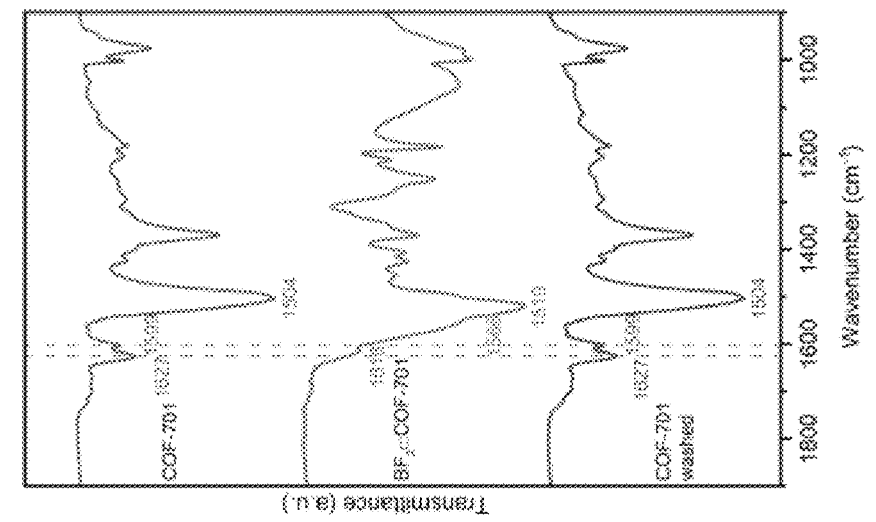
Figure 41:
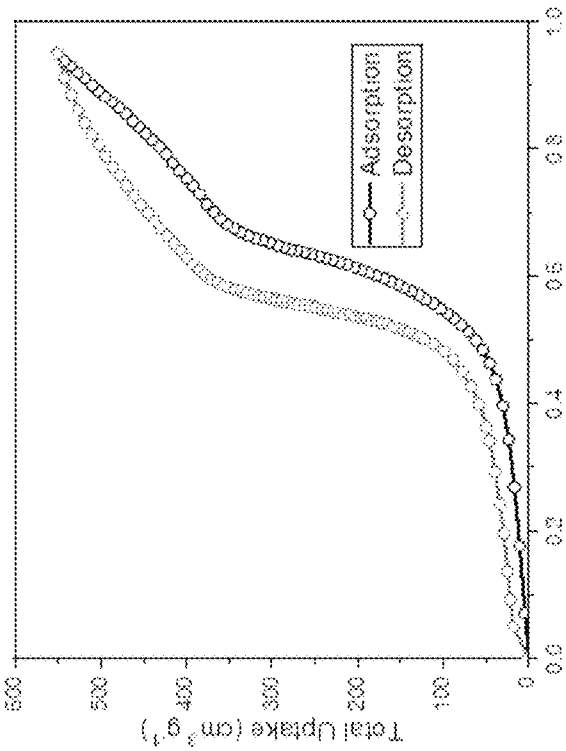
FIG. 41. $H_2O$ isotherm of COF-701 measured at 298 K.

COF-701 is provided as an example with chemically stable linkage and exhibits water harvesting performance at ambient temperature. COF-701 comprises of tritopic building blocks 1,3,5- triazine and ditopic building blocks biphenyl linked through unsubstituted olefin (—CH═CH—) linkage. COF-701 is shown to retain the crystallinity and chemical composition toward Brønsted acid and base, organolithium reagents, and Lewis acid, measured by WAXS and FT-IR before and after exposure to corresponding aqueous or organic solutions of chemicals (FIG. 14).

Figure 15:
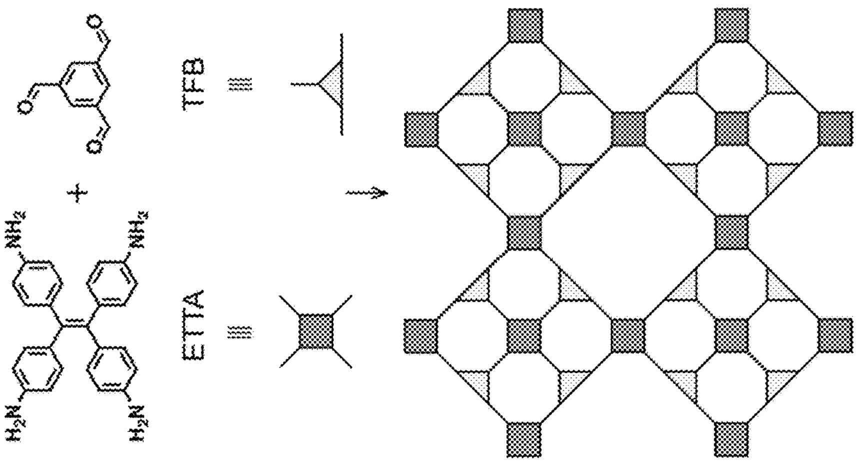
FIG. 15. The augmented mtf net of COF-432.

$H_2O$ vapor isotherm measurement is performed on COF-701 at 298 K (FIG. 15). The results indicate that at a relative humidity (RH) higher than 50%, COF-701 adsorbs $H_2O$ dependent on the value of RH. At 70% RH, COF-701 adsorbs 400 $cm^3/g$ (29.4 wt %) $H_2O$ vapor; at 100% RH (present in some coal or natural gas flue gas). COF-701 adsorbs 560 $cm^3/g$ (41.2 wt %) of $H_2O$. This result indicates a promising aspect for the material for capturing H2O from high-humidity gas mixtures, such as humid air or humid flue gas at 298 K.

References

Diercks, C. S.; Lin, S.; Kornienko, N.; Kapustin, E. A.; Nichols, E. M.; Zhu, C.; Zhao, Y.; Chang, C. J.; Yaghi, O. M. Reticular Electronic Tuning of Porphyrin Active Sites in Covalent Organic Frameworks for Electrocatalytic Carbon Dioxide Reduction. *J. Am. Chem. Soc.* 2018, 140, 1116-1122.

Zhang, B.; Wei, M.; Mao, H.; Pei, X.; Alshmimri, S. A.; Reimer, J. A.; Yaghi, O. M. Crystalline Dioxin-Linked Covalent Organic Frameworks from Irreversible Reactions. *J. Am. Chem. Soc.* 2018, 140, 12715-12719.

Guan, X.; Li, H.; Ma, Y.; Xue, M.; Fang, Q.; Yan, Y.; Valtchev, V.; Qiu, S. Chemically Stable Polyarylether-Based Covalent Organic Frameworks. *Nat. Chem.* 2019, 11, 587-594.

Lyu, H.; Diercks, C. S.; Zhu, C.; Yaghi, O. M. Porous Crystalline Olefin-Linked Covalent Organic Frameworks. *J. Am. Chem. Soc.* 2019, 141, 6848-6852.

Aspect 3. Enhanced Water Harvesting by Charged Covalent Organic Frameworks

Covalent organic frameworks (COFs) are crystalline, porous materials linked by strong covalent bonds. COFs can be used as water sorbents for water harvesting purposes. The large pore size of COFs provides high theoretical gravimetric water uptake capacity. However, the rather hydrophobic pore environment hinders the formation of water clusters inside the COF pore at low and medium relative humidity (RH) levels—a fundamental requirement for atmospheric water harvesting.

Description of Particular Embodiments

The subject COFs are constructed from only light atoms and provide the highest gravimetric water uptakes reported so far at low RH. In comparison to MOFs—sorbent materials currently utilized for atmospheric water harvesting; COFs do not rely on (heavy) metal usage during their synthesis. This not only avoids the additional associated cost but also potential toxicity associated with some of the metal cations.

Polar functional groups have been introduced to the backbone of COFs to increase the overall hydrophilicity of the pore. However, the attached functional groups cannot provide sufficient hydrophilicity for large-pore COFs which are particularly interesting due to large anticipated water uptakes. Our invention using charged frameworks substantially increases the water—framework interaction due to strong, wide-reaching polarization of the pore and consequently boost the sorbent performance.

Previous work incorporated salts in a porous neutral matrix material (such as silica gel). However, these materials suffer from salt leakage from the matrix and agglomeration in the pores. In our invention, the counter ions are immobilized through Coulombic interaction with the backbone. Thus, salt deliquescence and solution carryover are avoided. In the disclosed materials, the average distance between charges is much larger than in conventional desiccants where ions are closely packed. Such larger distance between the cations provides more space for water to cluster and prevents ions from crystallizing into a hydrated salt, which effectively accelerates water adsorption/desorption kinetics.

Description of Preferred Charged Framework Systems

Different strategies for generation of such charged frameworks are described below. The charged groups can be introduced into COFs during synthesize or through post synthetic modification. In general, both the charged backbone and the counter ions provide strong hydrogen bonding and ion-dipole interactions with water molecules to improve the water uptake ability of the COFs by rendering them more hydrophilic. The additional hydrophilicity and the generally large pores render the COF suitable for water uptake at low and medium RH, while exhibiting excellent kinetic water uptake properties.

An example of introducing charged groups during synthesis of the COF:

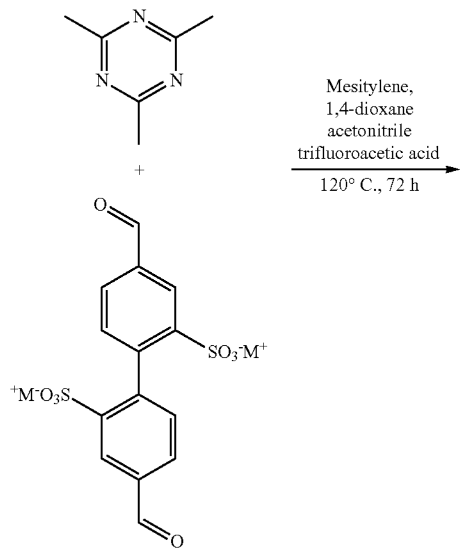

-continued
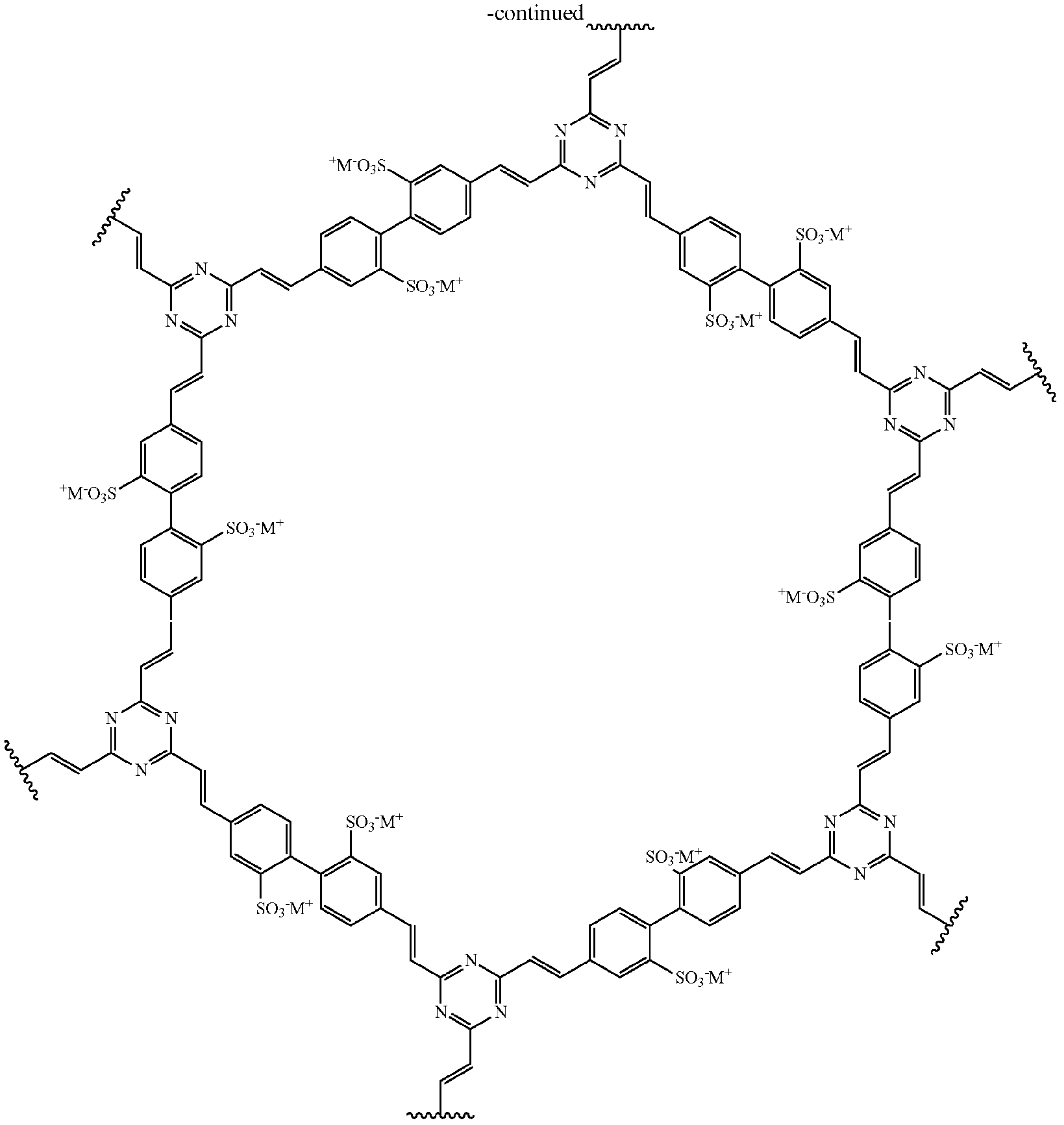
Examples of introducing charged groups through post synthetic modification of COFs:

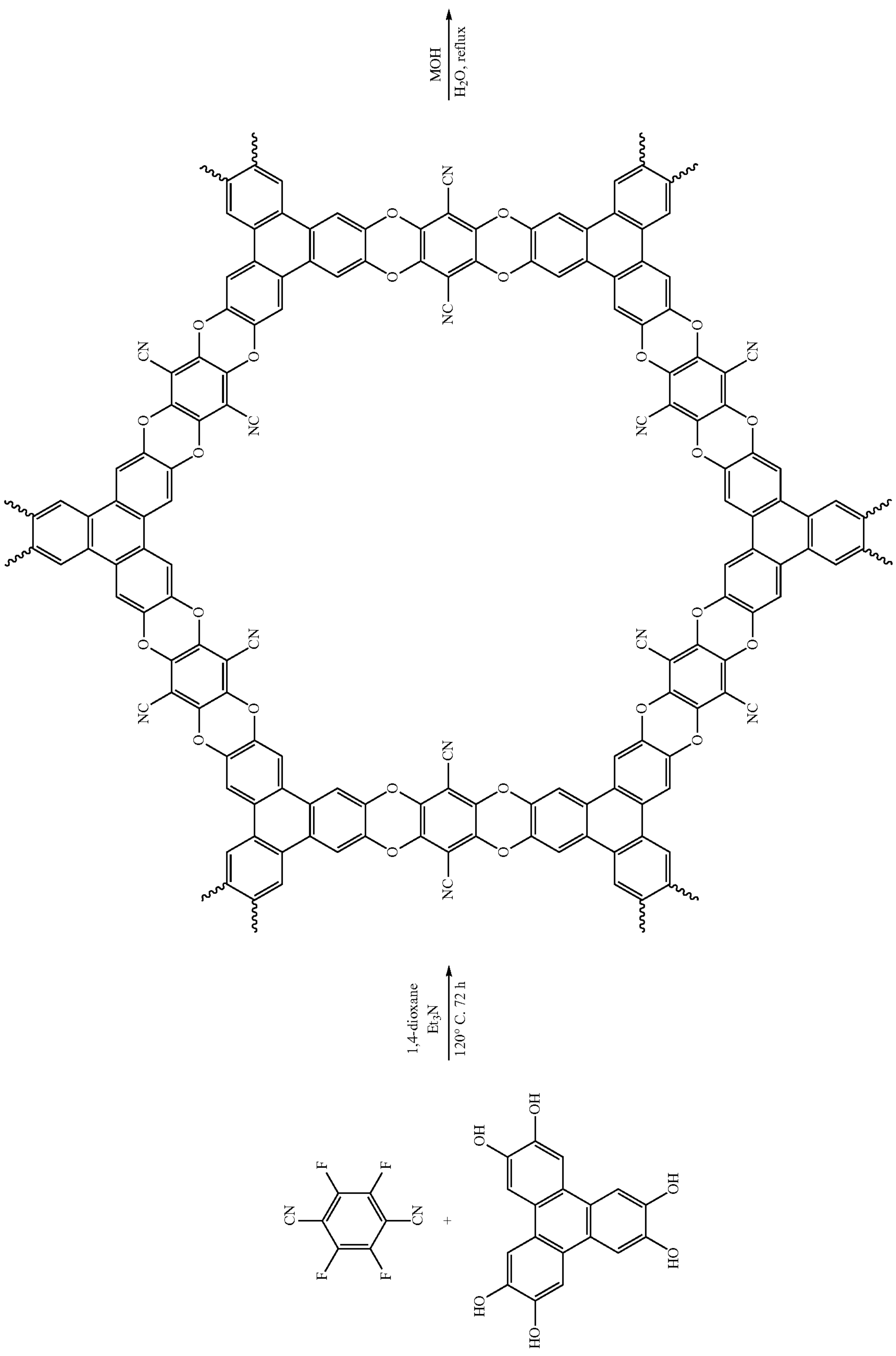
MOH
$H_2O$, reflux
1,4-dioxane
$Et_3N$
120° C. 72 h

-continued
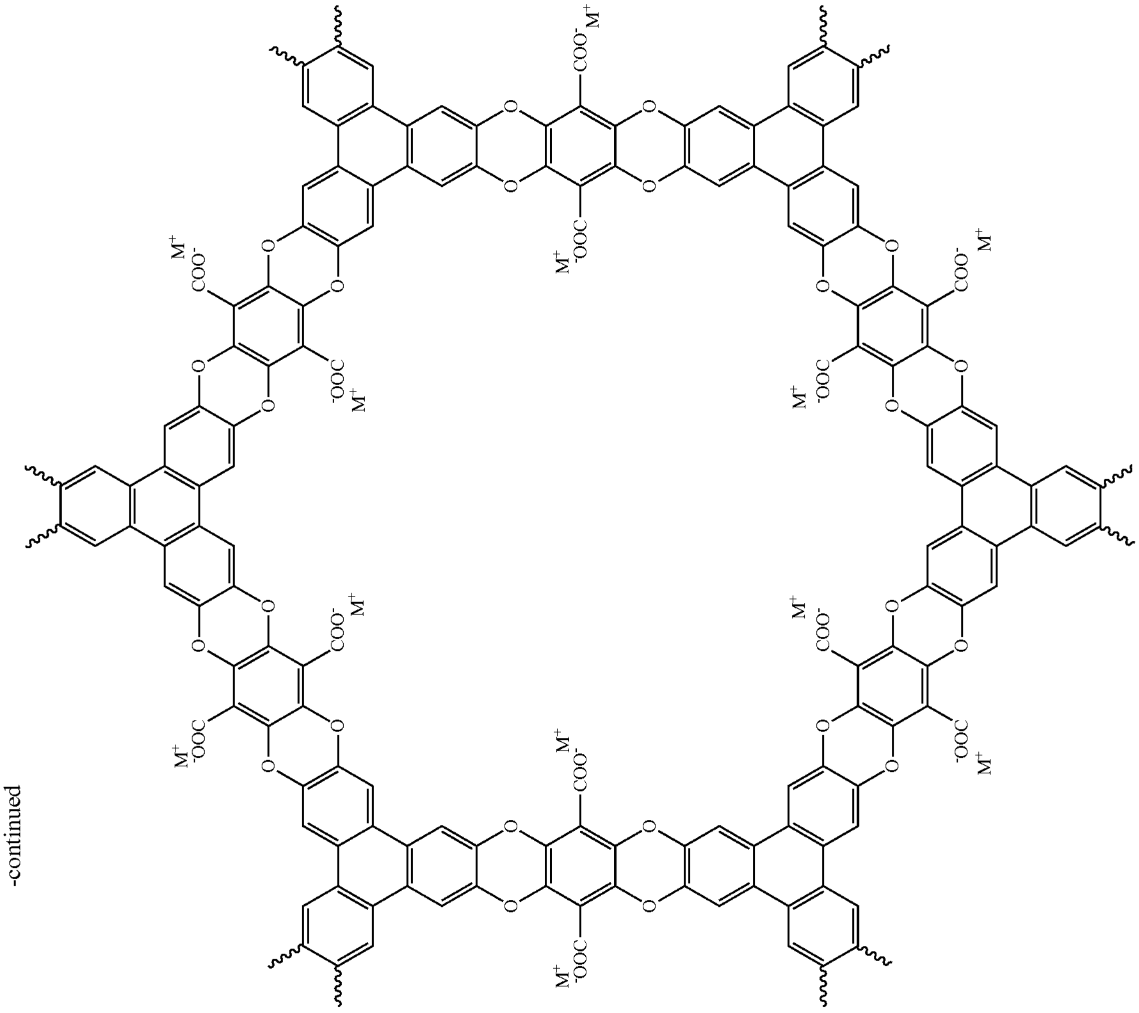

-continued
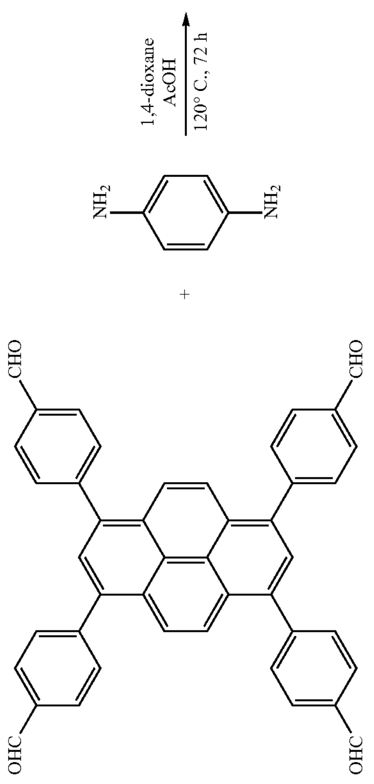

-continued
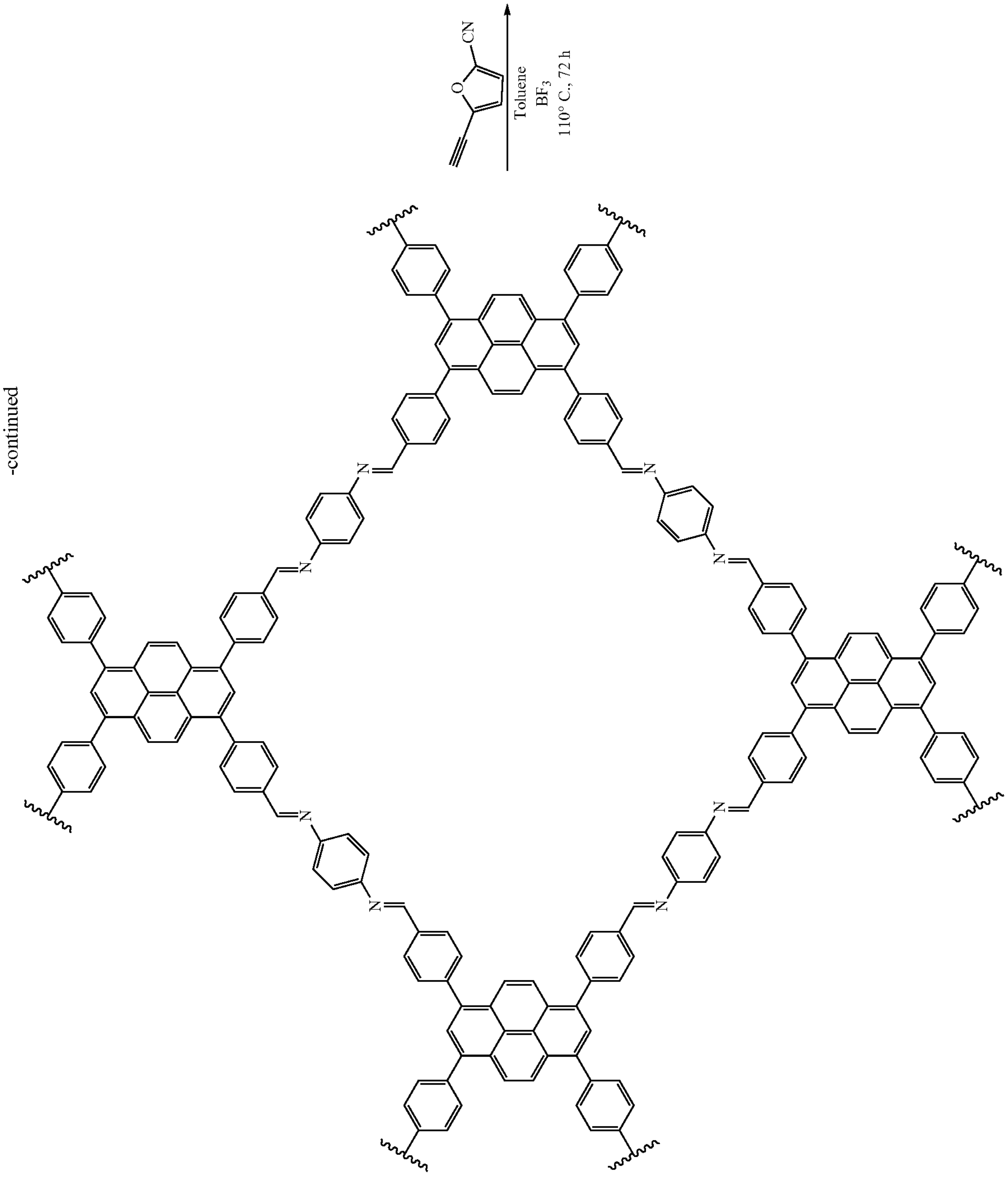

-continued
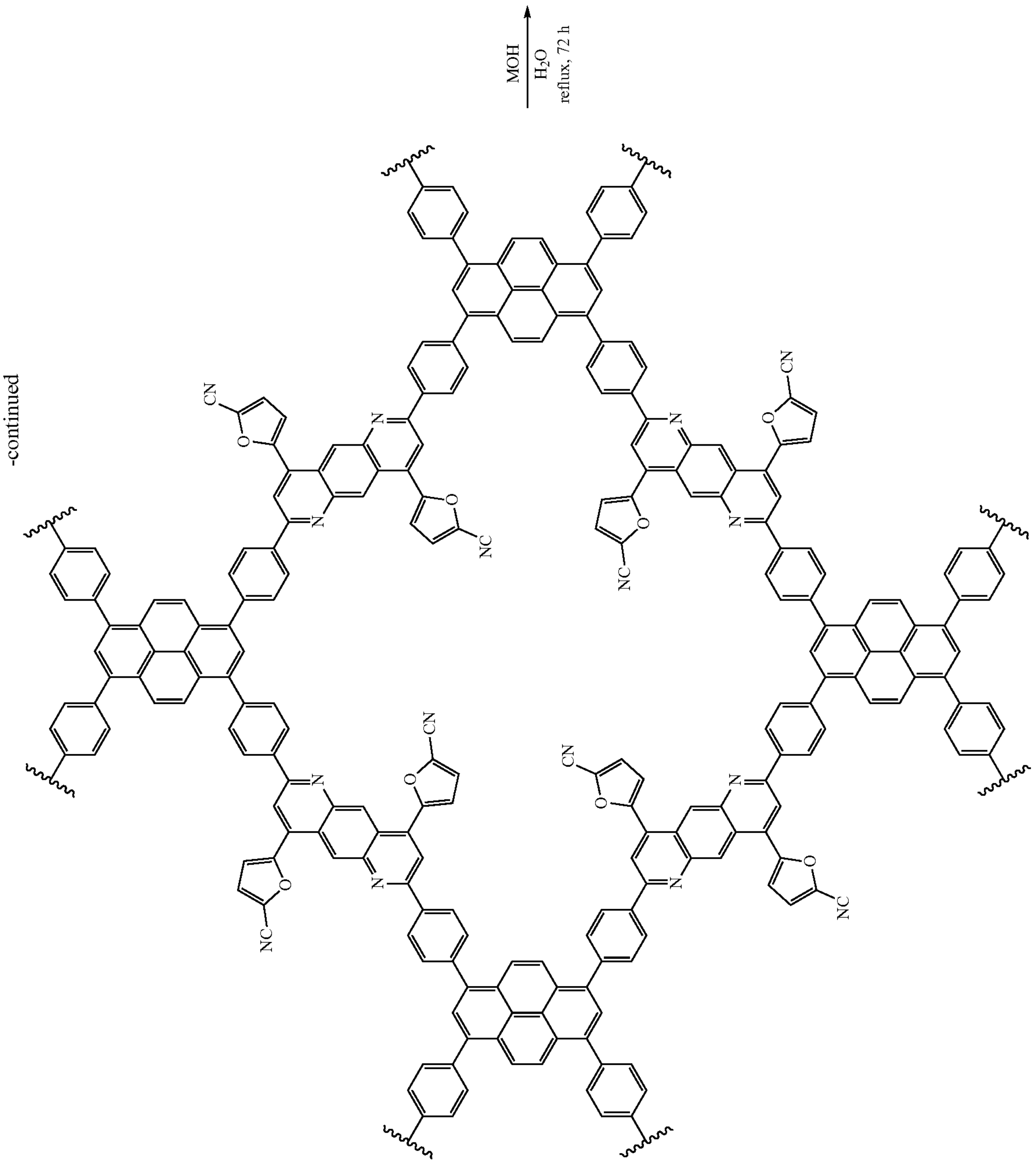

-continued
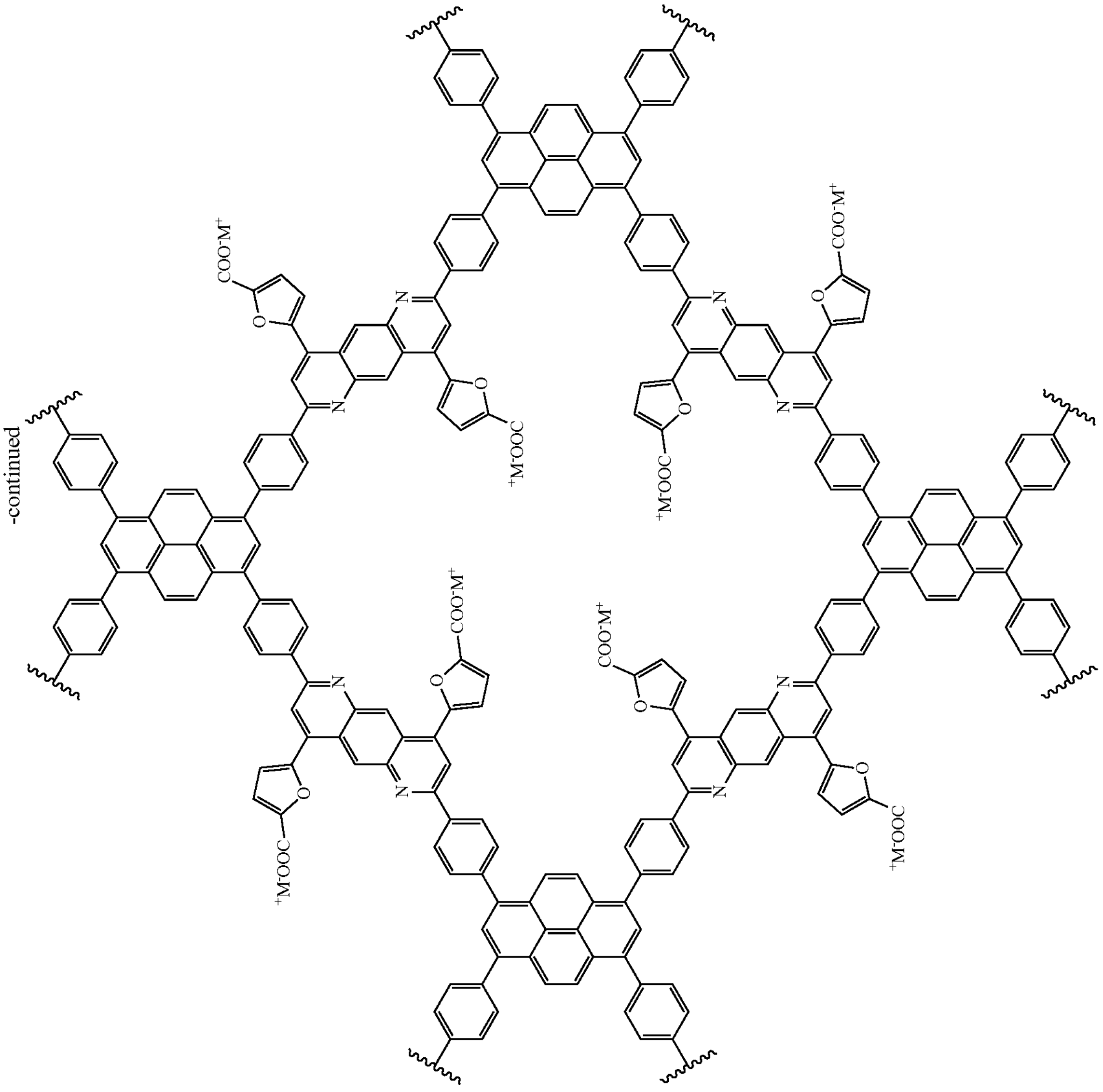

The subject covalent organic frameworks include charged functional groups that are attached to the backbone, such as Table 1:

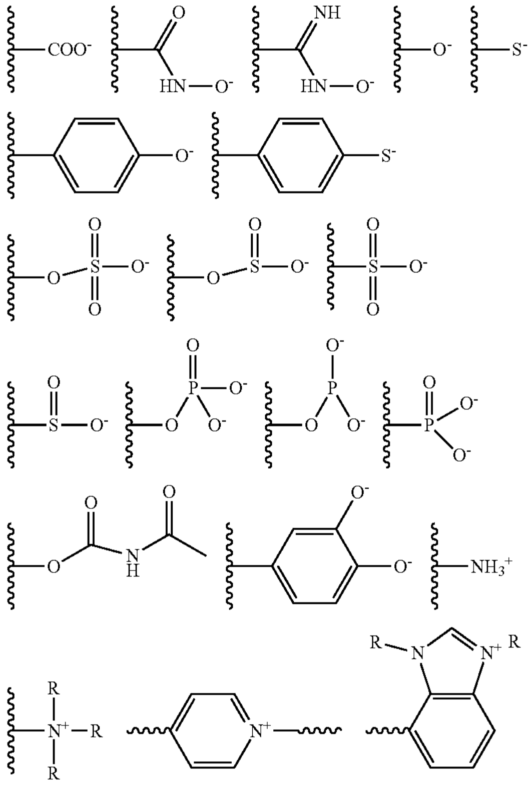

The subject covalent organic frameworks include counter ions, such as Table 2:

Inorganic counter ions:

$H^+$ $Li^+$ $Na^+$ $K^+$ $Rb^+$ $Cs^+$ $Mg^{2+}$ $Ca^{2+}$ $Sr^{2+}$ $Ba^{2+}$ $Al^{3+}$ $Sc^{3+}$ $Cr^{3+}$ $Mn^{2+}$ $Fe^{3+}$ $Fe^{2+}$ $Co^{3+}$ $Co^{2+}$ $Ni^{2+}$ $Cu^{2+}$ $Zn^{2+}$ $F^-$ $Cl^-$ $Br^-$ $I^-$ $NO_3^-$ $ClO_4^-$ $B(OH)_4^-$ $PF_6^-$ $CO_3^{2-}$ $SO_3^{2-}$ $SO_4^{2-}$ $PO_4^{3+}$ $P_nO_{3n+1}^{(n+2)-}$

Organic counter ions:

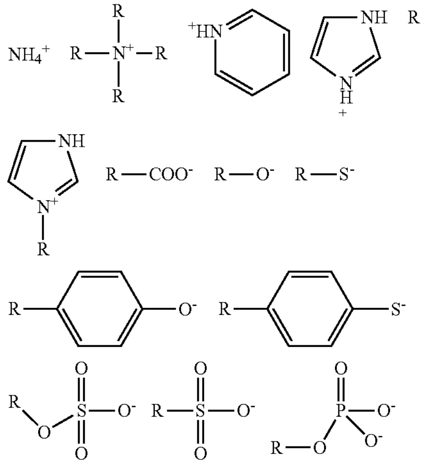

-continued

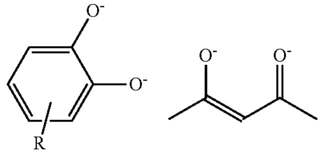

The subject covalent organic frameworks include organic linkages, such as Table 3:

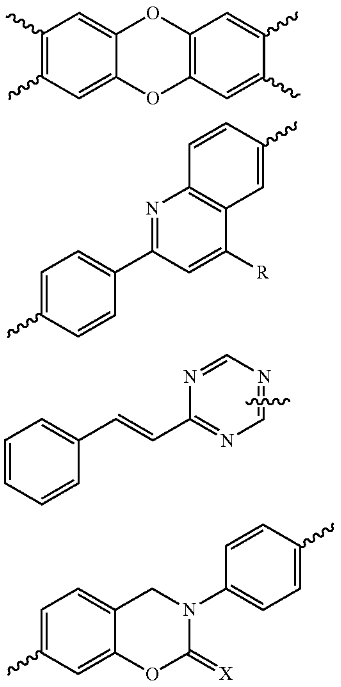

X = O, S

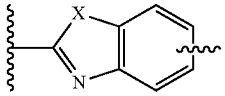

X = O, S, N

The subject covalent organic frameworks include organic linkers, such as Table 4:

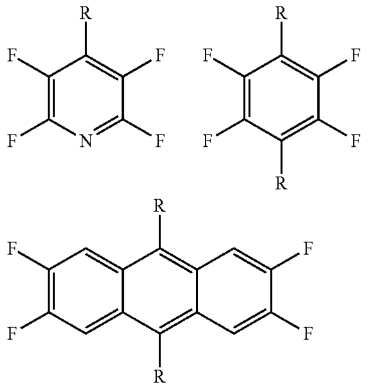

-continued
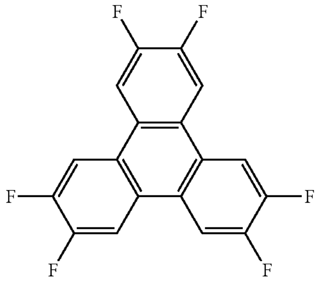
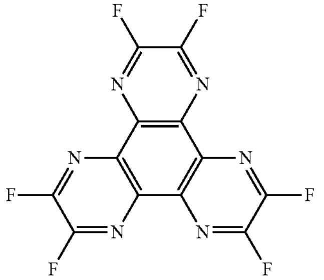
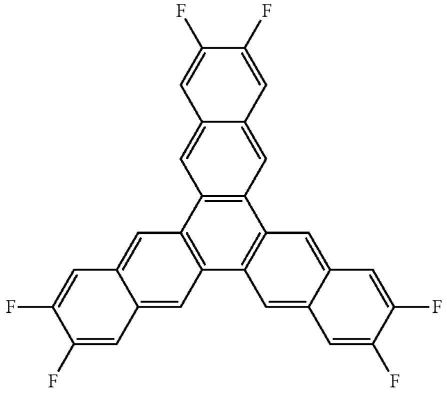
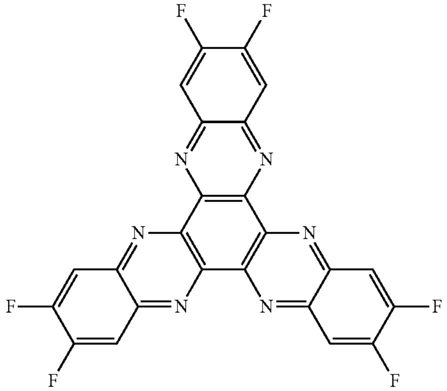
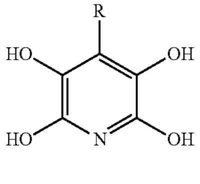
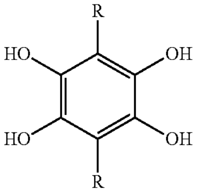
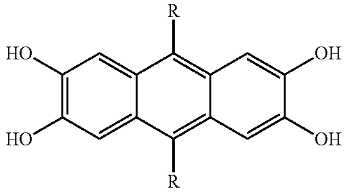
-continued
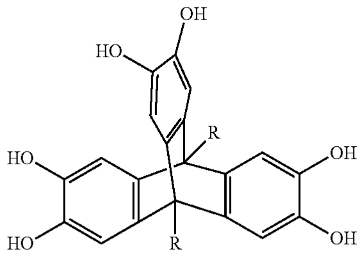
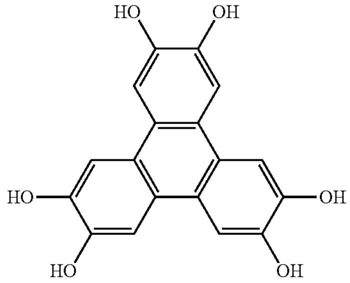
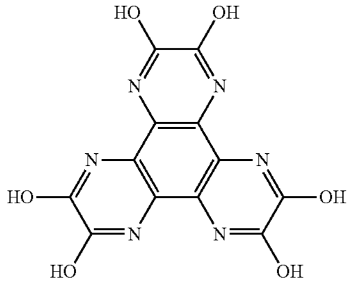
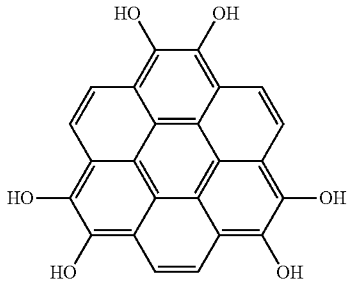
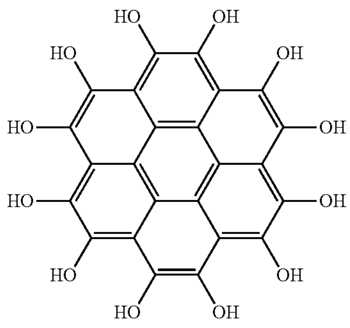

-continued
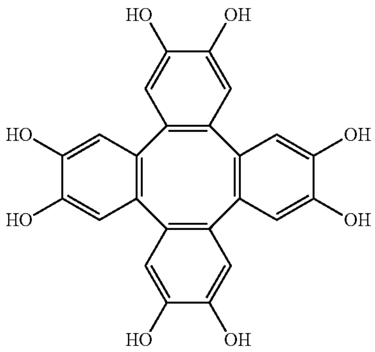
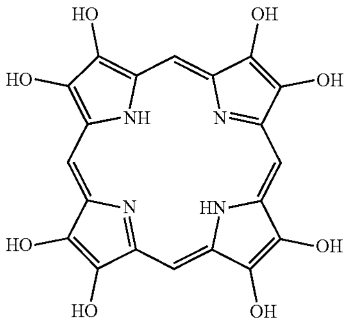
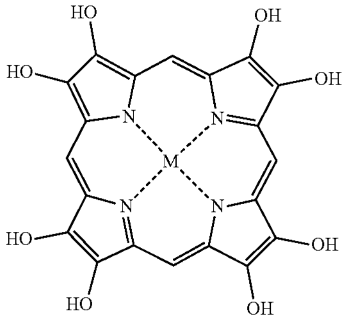
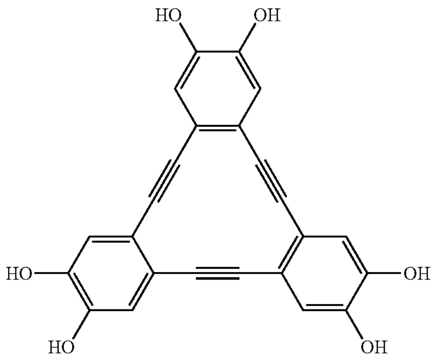
-continued
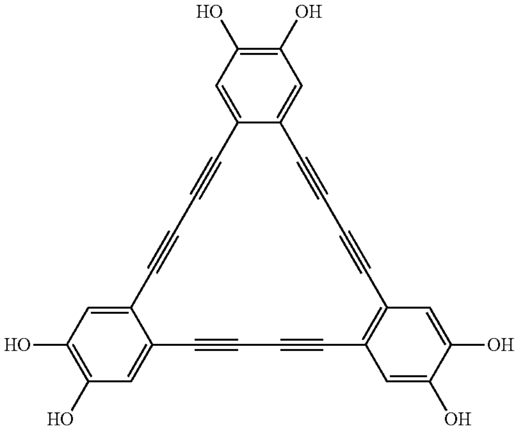
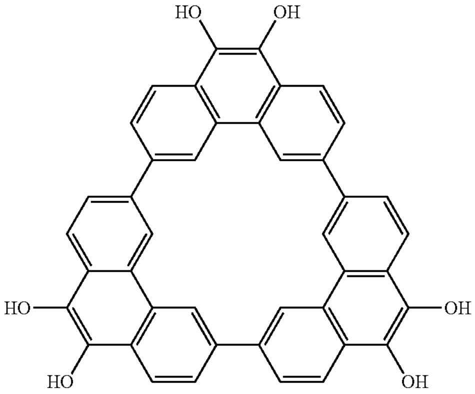
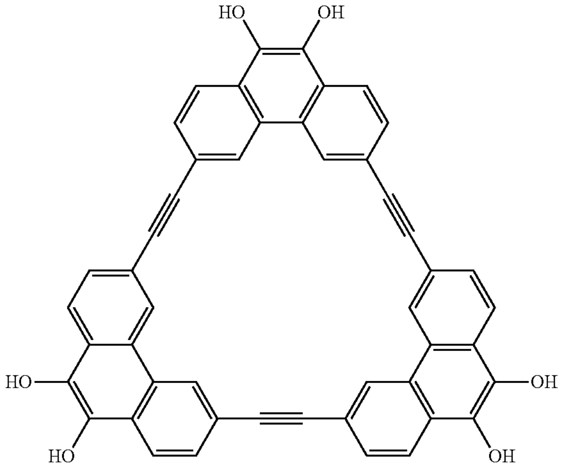
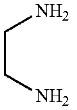
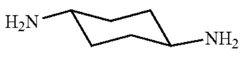
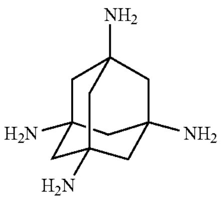
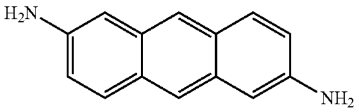

-continued
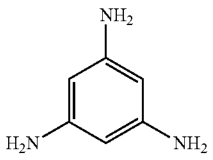
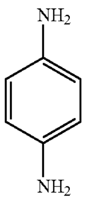
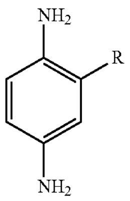
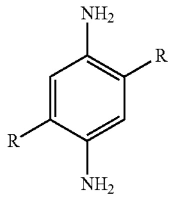
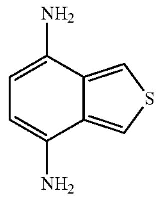
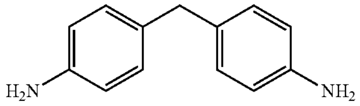
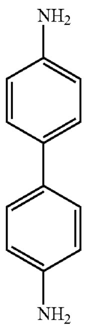
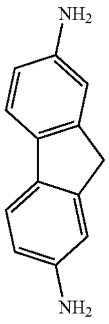
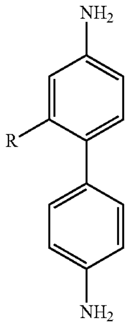
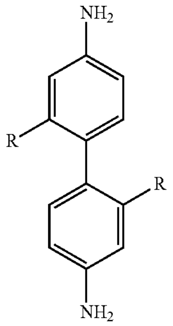
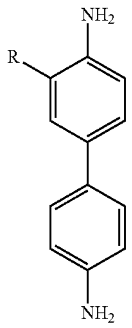
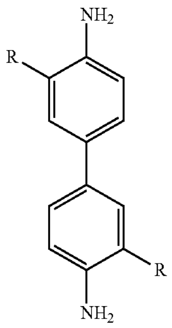
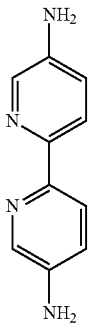
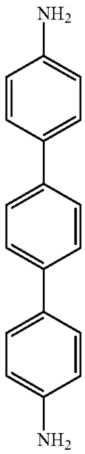
-continued
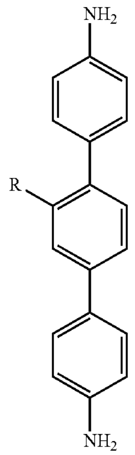
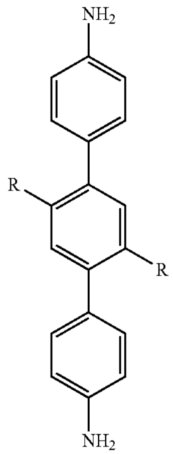
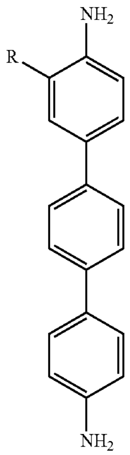
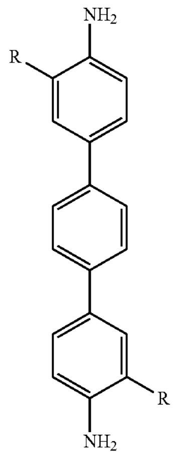
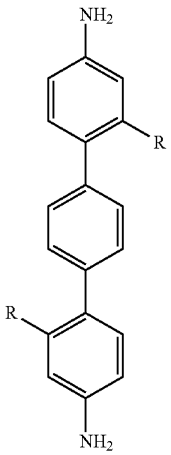
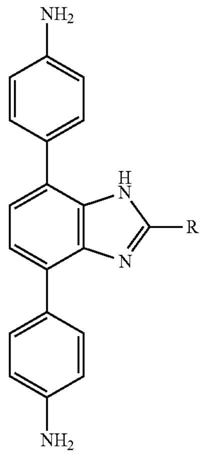
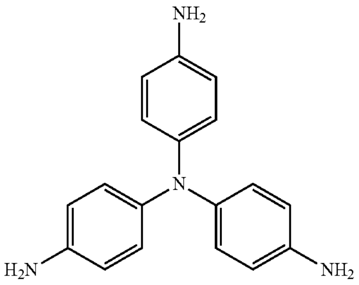

-continued
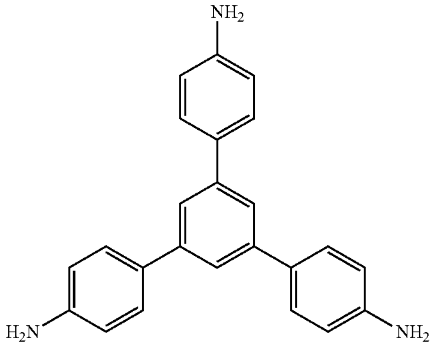
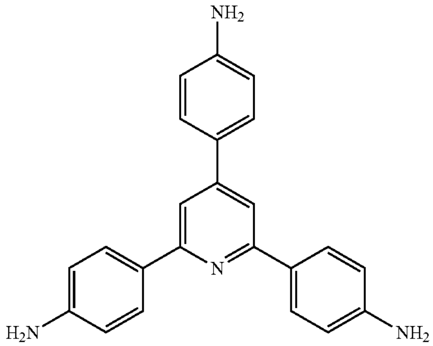
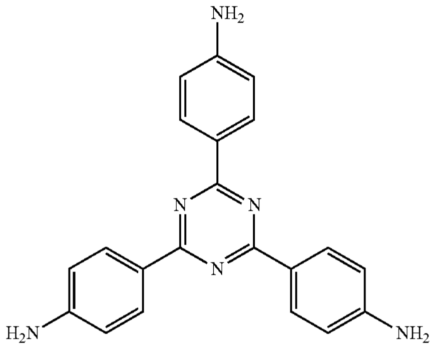
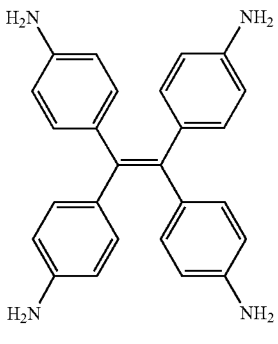
-continued
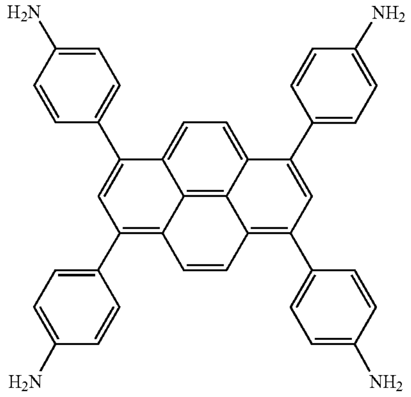
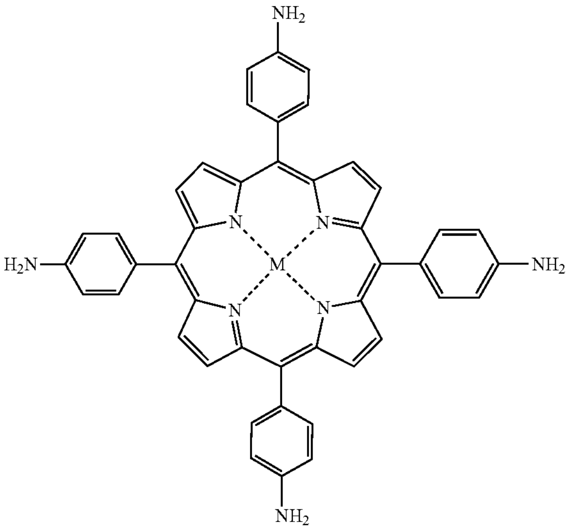
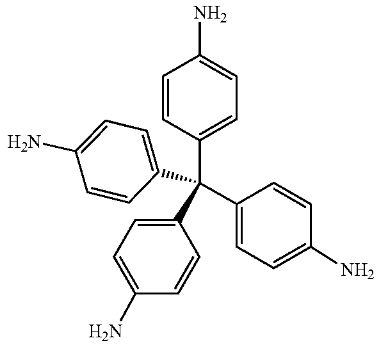
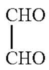
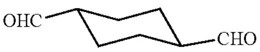
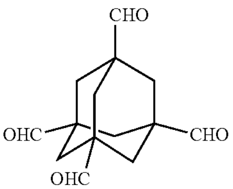
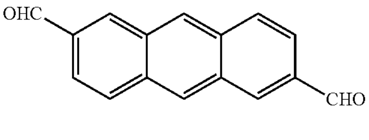

-continued
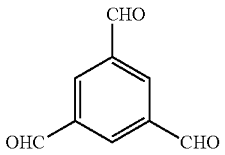
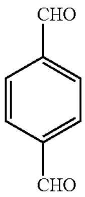
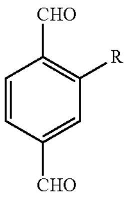
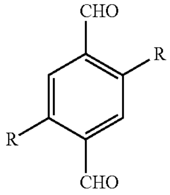
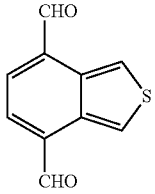
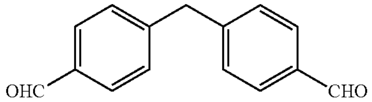
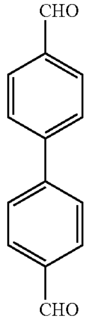
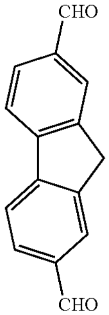
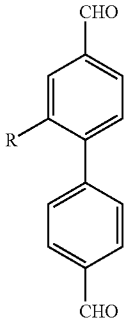
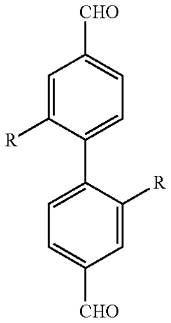
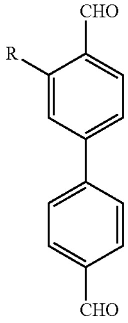
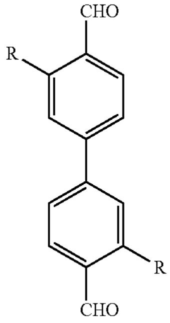
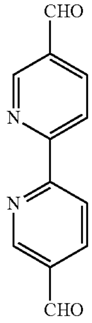
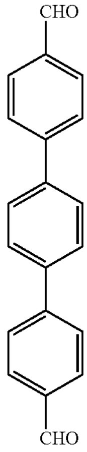
-continued
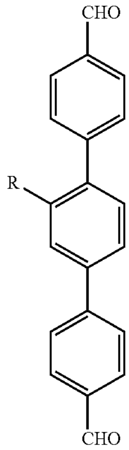
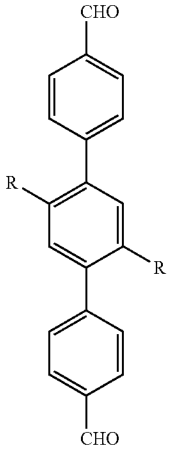
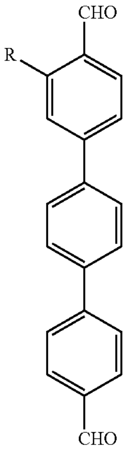
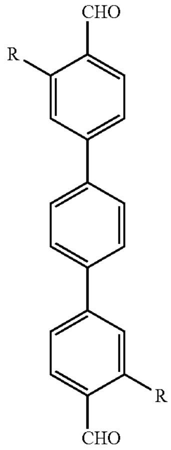
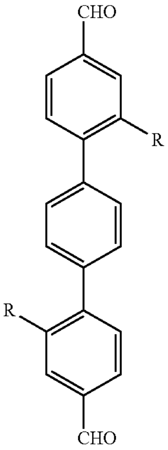
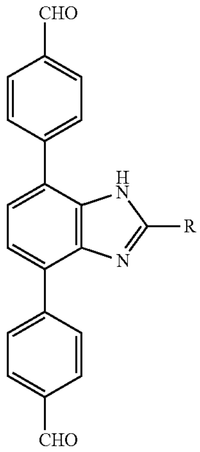
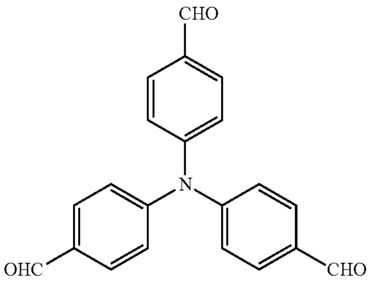

-continued
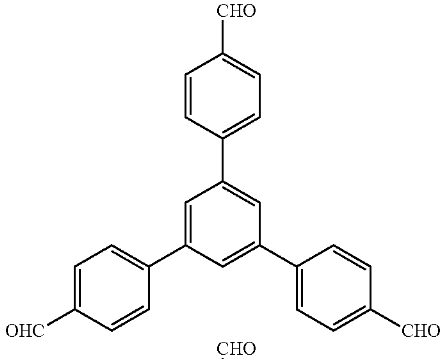
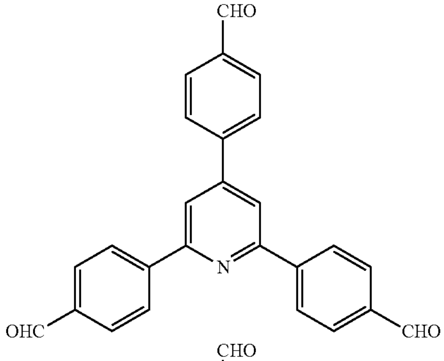
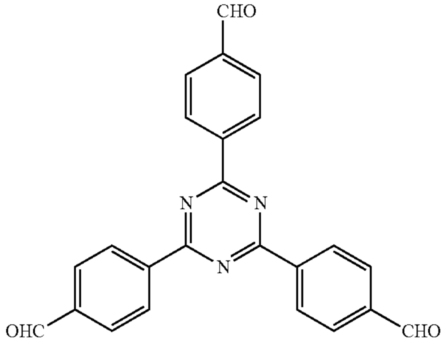
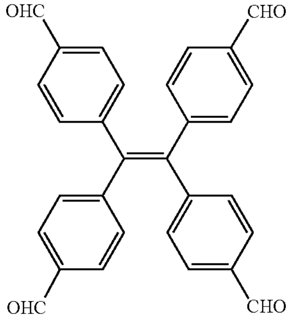
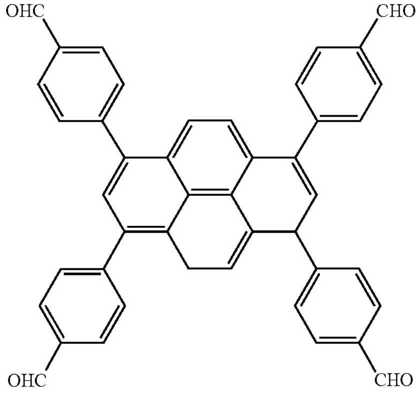
-continued
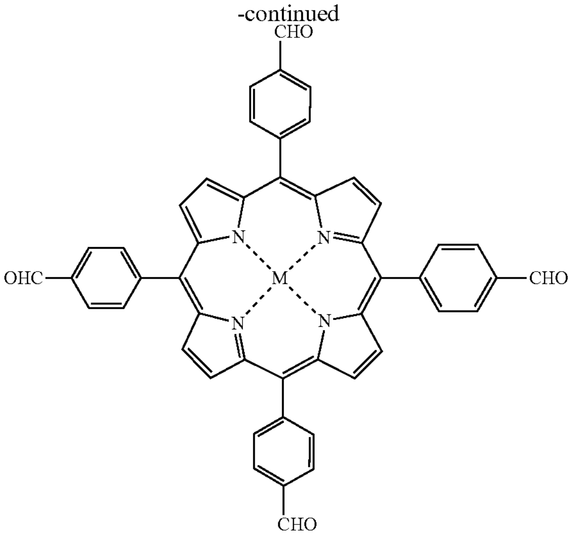
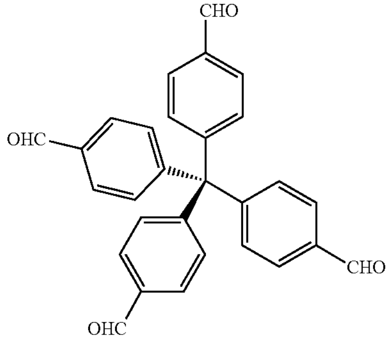
M = Mg, Ca, Mn, Fe, Co, Ni, Cu, Zn, Pt, Pd
R =
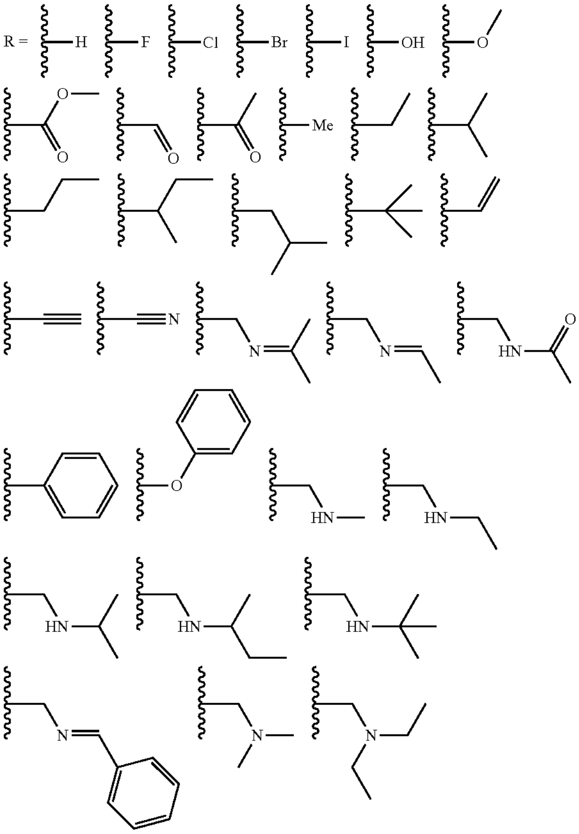

-continued

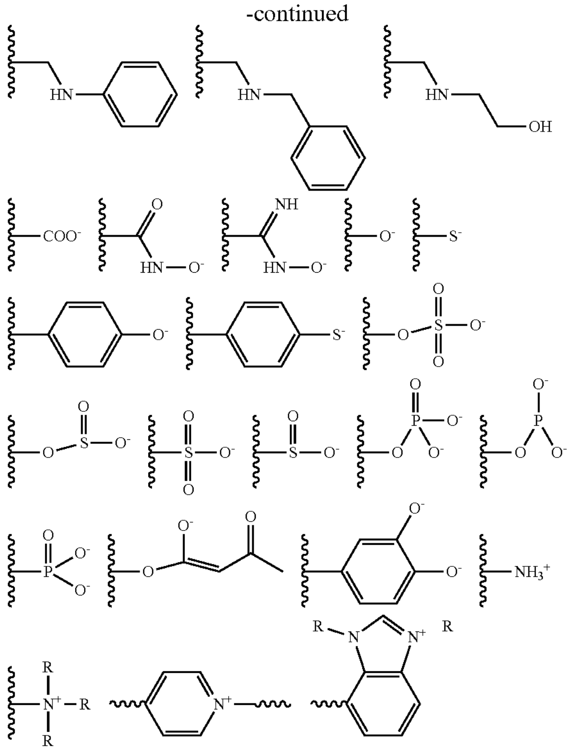

The invention claimed is:

1. A composition comprising a porous crystalline covalent organic framework (COF), constructed from a tetratopic linker 1,1,2,2,-tetrakis (4-aminophenyl) ethene [ETTA, $C_{26}H_{16}(NH_2)_4$] and a tritopic linker 1,3,5-triformylbenzene [TFB, $C_6H_3(CHO)_3$], termed COF-432 {$[ETTA)_3(TFB)_4]$ imine}, which exhibits a mtf topology.

2. The composition of claim 1 wherein the linkage is imine (—CH═N—).

3. A device comprising the composition of claim 1, selected from the group consisting of an atmospheric water harvester, a heat pump, a dehumidifier, an adsorption refrigerator, and a solar cooling system.

4. A method of making the composition of claim 1 comprising the step of condensing the linkers to form the crystalline framework.

5. A method of using the composition of claim 1 comprising contacting the composition with air under conditions wherein the composition adsorbs water from the air.

6. The method of claim 5, wherein the air has a relative humidity of 20-40%.

* * * * *